US008535687B2

US 8,535,687 B2

(12) United States Patent
Draghia-Akli et al.

(10) Patent No.: US 8,535,687 B2
(45) Date of Patent: Sep. 17, 2013

(54) SMALLPOX DNA VACCINE AND THE ANTIGENS THEREIN THAT ELICIT AN IMMUNE RESPONSE

(75) Inventors: Ruxandra Draghia-Akli, Brussels (BE); Jon Prigge, Spring, TX (US); Niranjan Y. Sardesai, North Wales, PA (US); David B. Weiner, Merion Station, PA (US); Lauren A. Hirao, Philadelphia, PA (US)

(73) Assignees: The Trustees of the University of Pennsylvania, Philadelphia, PA (US); Inovio Pharmaceuticals, Inc., Blue Bell, PA (US)

( * ) Notice: Subject to any disclaimer, the term of this patent is extended or adjusted under 35 U.S.C. 154(b) by 474 days.

(21) Appl. No.: 12/473,634

(22) Filed: May 28, 2009

(65) Prior Publication Data
US 2009/0304627 A1     Dec. 10, 2009

Related U.S. Application Data

(60) Provisional application No. 61/056,687, filed on May 28, 2008, provisional application No. 61/121,054, filed on Dec. 9, 2008.

(51) Int. Cl.
| | |
|---|---|
| *A61K 39/275* | (2006.01) |
| *A61K 39/12* | (2006.01) |
| *A61K 39/00* | (2006.01) |
| *C12Q 1/68* | (2006.01) |
| *C12N 15/00* | (2006.01) |

(52) U.S. Cl.
USPC ................. 424/232.1; 424/186.1; 424/204.1; 424/9.2; 435/6.1; 435/320.1

(58) Field of Classification Search
None
See application file for complete search history.

(56) References Cited

U.S. PATENT DOCUMENTS

| | | | |
|---|---|---|---|
| 5,593,972 | A | 1/1997 | Weiner et al. |
| 5,962,428 | A | 10/1999 | Carrano et al. |
| 7,238,522 | B2 | 7/2007 | Hebel et al. |
| 7,245,963 | B2 | 7/2007 | Draghia-Akli et al. |
| 2002/0176871 | A1 | 11/2002 | Hooper et al. |
| 2005/0052630 | A1 | 3/2005 | Smith et al. |
| 2006/0025368 | A1 | 2/2006 | Draghia-Akli et al. |

FOREIGN PATENT DOCUMENTS

| | | |
|---|---|---|
| WO | WO9324640 | 9/1993 |
| WO | WO9416737 | 8/1994 |
| WO | 2009009039 | 1/2009 |

OTHER PUBLICATIONS

Bartlett et al., Murine interferon lambdas (type III interferons) exhibit potent antiviral activity in vivo in a poxvirus infection model, 2005, Journal of General Virology, vol. 86, pp. 1589-1596.*
Hooper et al., Smallpox DNA vaccine delivered by novel skin electroporation device protects mice against intranasal poxvirus challenge, 2007, Vaccine, vol. 25, pp. 1814-1823.*
GenBank Accession AY243312, Vaccinia virus WR, complete genome, Mar. 14, 2006.*
Otero et al., Efficacy of novel plasmid DNA encoding vaccinia antigens in improving current smallpox vaccination strategy, 2006 (Online Aug. 18, 2005), Vaccine, vol. 24, pp. 4461-4470.*
Kumar et al., Immunogenicity Testing of a Novel Engineered HIV-1 Envelope Gp140 DNA Vaccine Construct, 2006, DNA and Cell Biology, vol. 25, No. 7, pp. 383-392.*
Boyer, J.D. et al., "SIV DNA vaccine co-administered with IL-12 expression plasmid enhances CD8 SIV cellular immune responses in cynomolgus macaques", J. Med. Primatol., 2005, 34:262-270.
Draghia-Akli, R. et al., "Innovative electroporation for therapeutic and vaccination applications", Gene Therapy & Molecular Biology, 2005, 9:329-38.
Laddy, D.J. et al., "Heterosubtypic protection against pathogenic human and avian influenza viruses via in vivo electroporation of synthetic consensus DNA antigen", PLoS ONE, 2008, 3:e2517.
Demkowicz et al., "Identification and characterization of vaccinia virus genes encoding proteins that are highly antigenic in animals and are immunodominant in vaccinated humans", J. Virol., 1992, 66:386-398.
Wilson, R.L. et al., "Commensal bacteria as a novel delivery system for subunit vaccines directed against agents of bioterrorism", Advanced Drug Delivery Reviews, 2005, 57:1392-1402.
Pulford, D.J. et al., "Differential efficacy of vaccinia virus envelope proteins administered by DNA immunisation in protection of BALB/c mice from a lethal intranasal poxvirus challenge", Vaccine, 2004, 22:3358-3366.
Yoder, Jennifer D. et al., "Pox proteomics: mass spectrometry analysis and identification of *Vaccinia virion* proteins", 2006, Virology Journal, 3:10, pp. 1-16.

* cited by examiner

*Primary Examiner* — Benjamin P Blumel
(74) *Attorney, Agent, or Firm* — Pepper Hamilton, LLP

(57) ABSTRACT

The present invention relates to DNA vaccines that are capable of generating a protective immune response in mammals against a pox virus, and comprises at least one DNA plasmid capable of expressing a plurality of VACV MV antigens, and at least one DNA plasmid capable of expressing a plurality of VACV EV antigens. Also, the present invention relates to methods of inducing a protective immune response in a mammal to pox virus, including a neutralizing antibody response, comprising: injecting into tissue of said mammal said DNA vaccine.

21 Claims, 41 Drawing Sheets

List of small pox plasmids manufactured under cGLP and a summary of their physical/chemical characteristics at product release

| Category | Plasmid | Lot# | Volume | Conc.* | Quantity | Purity | Osm** | Endotox*** |
|---|---|---|---|---|---|---|---|---|
| Small Pox | pGX40xx | | (mL) | (mg/mL) | (mg) | $A_{260/280}$ | mOsm/kg water | EU/mg |
| A4L | pGX4001 | pGX4001.PD07001 | 38.3 | 11.2 | 429 | 1.9 | 31 | 1.4 |
| A27L | pGX4002 | pGX4001.PD07001 | 18.5 | 7.4 | 137 | 1.9 | 17 | 2.6 |
| B5R | pGX4003 | pGX4001.PD07001 | 60 | 9.1 | 548 | 1.9 | 15 | 0.35 |
| A33R | pGX4004 | pGX4001.PD07001 | 27 | 13.6 | 367 | 1.9 | 22 | 0.373 |
| A56R | pGX4005 | pGX4001.PD07001 | 31 | 12.5 | 388 | 1.9 | 19 | 0.565 |
| F9L | pGX4006 | pGX4001.PD07001 | 30 | 10.2 | 306 | 2.0 | 20 | 0.692 |
| H3L | pGX4007 | pGX4001.PD07001 | 31 | 11.2 | 346 | 1.9 | 27 | 0.5 |
| L1R | pGX4008 | pGX4001.PD07001 | 26 | 10.4 | 270 | 1.9 | 27 | 0.5 |
| Average ± SEM | | | | 10.7 ± 0.68 | | | | |

* Concentration
** Osmolality
*** Endotoxin

pGX4002 - Plasmid expressing smallpox A27L antigen pGX4002
3363 bp

- pCMV
- Sac I (620)
- Kpn I (723)
- BamH I (750)
- A27L
- Xho I (1151)
- Xba I (1157)
- BGH pA
- Kanamycin
- pUC ori

| Elements | Base Pairs |
|---|---|
| CMV promoter | 137-722 |
| Optimized Coding Sequence | 723-1150 |
| Bovine GH PolyA | 1187-1417 |
| Kanamycin Resistance | 1590-2384 |
| Origin of Replication | 2684-3357 |

FIG. 3

FIG. 4 pGX4003 - Plasmid expressing smallpox B5R antigen pGX4003 3972 bp

Features: pCMV, SacI (620), HindIII (713), BamHI (738), PstI (1176), B5R, EcoRI (1502), XhoI (1760), XbaI (1766), BGH pA, Kanamycin, pUC ori

| Elements | Base Pairs |
|---|---|
| CMV promoter | 137-712 |
| Optimized Coding Sequence | 713-1759 |
| Bovine GH PolyA | 1796-2026 |
| Kanamycin Resistance | 2199-2993 |
| Origin of Replication | 3293-3966 | pGX4004 - Plasmid expressing smallpox A33R antigen pGX4006 - Plasmid expressing smallpox F9L antigen pGX4006 3731 bp

Features: pCMV, T7, HindIII (713), KpnI (723), EcoRI (754), F9L, NotI (1513), XhoI (1519), XbaI (1525), BGH pA, Kanamycin, pUC ori

| Elements | Base Pairs |
| --- | --- |
| CMV promoter | 137-724 |
| Optimized Coding Sequence | 754-1524 |
| Bovine GH PolyA | 1555-1785 |
| Kanamycin Resistance | 1958-2752 |
| Origin of Replication | 3052-3725 |

FIG. 7 pGX4008 - Plasmid expressing smallpox L1R antigen pGX4008 3827 bp

Features: pCMV, SacI (620), T7, HidIII (713), L1R, BamHI (1559), PstI (1591), NotI (1609), XhoI (1615), XbaI (1621), BGH pA, Kanamycin, pUC ori

| Elements | Base Pairs |
| --- | --- |
| CMV promoter | 137-712 |
| Optimized Coding Sequence | 713-1558 |
| Bovine GH PolyA | 1651-1881 |
| Kanamycin Resistance | 2054-2848 |
| Origin of Replication | 3148-3821 |

FIG. 9

Example 4: Pilot study in non-human primates – study timeline

Example 5: IM or ID vaccination schedule

New Zealand White rabbits were vaccinated with a combination of antigens: A27L, B5R, A4L, and H5HA from influenza virus (used as a positive control)

Different electroporation conditions, pulse patterns and injection volumes /dose were evaluated.

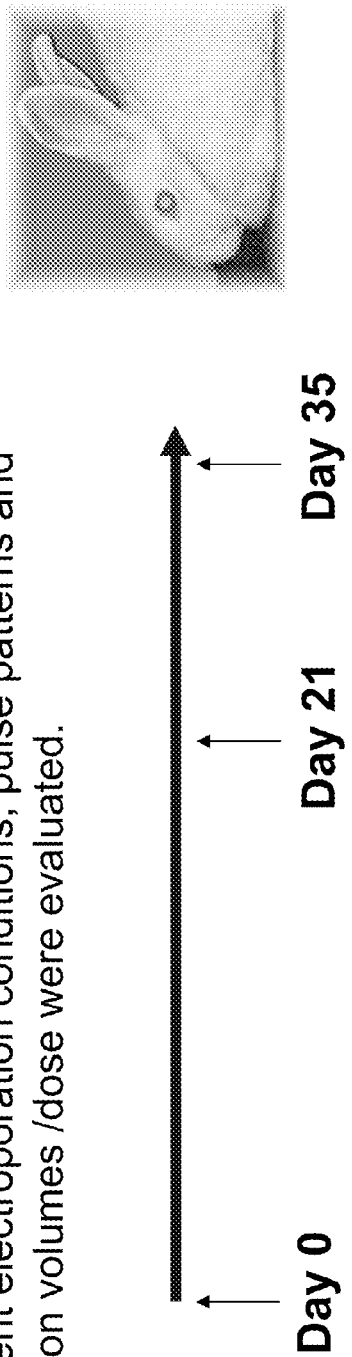

Day 0      Day 21      Day 35

- Day 0:    Pre-bleed, IM or ID vaccinations
- Day 21:    Bleed, IM or ID vaccinations
- Day 35:    Bleed and sacrificed

FIG. 17

IM or ID vaccinations

| GR. | NB | LAG | AMPS | PROG | PULSE NB. | IM/ID | PLASMID HA / SPOX(3) |
|---|---|---|---|---|---|---|---|
| A | 4 | 4 | 0.2 | 0010 | 2 | ID | 100µl – 0.25 mg x 4 |
| B | 4 | 4 | 0.2 | 0011 | 3 | ID | 100µl – 0.25 mg x 4 |
| C | 4 | 4 | 0.2 | 0010 | 2x2 | ID | 100µl – 0.25 mg x 4 |
| D | 4 | 4 | 0.2 | 0011 | 3x2 | ID | 100µl – 0.25 mg x 4 |
| E | 3 | NA | NA | NA | NA | ID | 100µl – 0.25 mg x 4 |
| F | 4 | 80 | 0.5 | 0005 | 3 | IM | 500µl – 0.25 mg x 4 |
| G | 4 | 4 | 0.5 | 0005 | 3 | IM | 500µl – 0.25 mg x 4 |
| H | 3 | 4 | 0.5 | 0005 | 3 | IM | 1000µl – 0.25 mg x 4 |
| I | 4 | 10-15 | 0.5 | 0005 | 3 | IM | 500µl – 0.25 mg x 4 |
| J | 3 | NA | NA | NA | NA | IM | 500µl – 0.25 mg x 4 |

Rabbits received a combination of plasmids encoding A4L, A27L, B5R, and flu HA as a positive control

Example 6: IM or ID vaccination schedule

- New Zealand White rabbits were vaccinated with the combination of plasmid DNA's:
  - B5R + 7 parts pVAX
  - A27L, B5R, H3L, L1R + 4 parts pVAX
  - A56R, A4L, A27L, A33R, B5R, F9L, H3L, L1R
  - Negative control – 8 parts pVAX

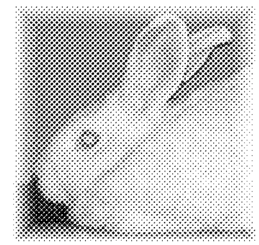

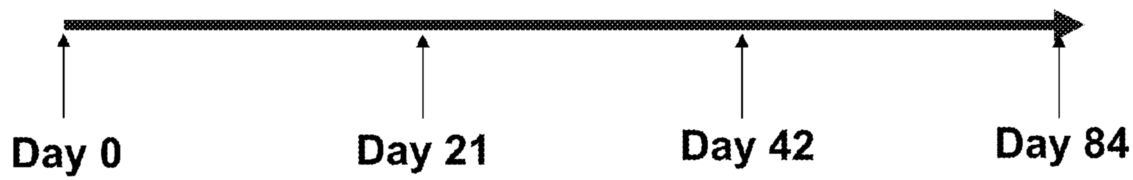

- Day 0: Pre-bleed, IM or ID vaccinations
- Day 21: Bleed, IM or ID vaccinations
- Day 42: Bleed
- Day 84: Bleed and sacrificed

FIG. 22

IM vs. ID vaccinations

| GR. | NB | LAG (s) | AMPS | PROG | PULSE NB. | IM/ID | PLASMID |
|---|---|---|---|---|---|---|---|
| A | 4 | 4 | 0.2 | 0010 | 2X2 | ID | 100μl – 0.125 mg x 8 |
| B | 4 | 4 | 0.2 | 0010 | 2X2 | ID | 100μl – 0.125 mg x 8 |
| C | 4 | 4 | 0.2 | 0010 | 2X2 | ID | 100μl – 0.125 mg x 8 |
| D | 4 | 4 | 0.2 | 0010 | 2X2 | ID | 100μl – 0.125 mg x 8 |
| E | 4 | NA | NA | NA | NA | ID | 100μl – 0.125 mg x 8 |
| F | 4 | 4 | 0.5 | 0005 | 3 | IM | 500μl – 0.125 mg x 8 |
| G | 4 | 4 | 0.5 | 0005 | 3 | IM | 500μl – 0.125 mg x 8 |
| H | 4 | 4 | 0.5 | 0005 | 3 | IM | 500μl – 0.125 mg x 8 |
| I | 4 | 4 | 0.5 | 0005 | 3 | IM | 500μl – 0.125 mg x 8 |
| J | 4 | NA | NA | NA | NA | IM | 500μl – 0.125 mg x 8 |

Groups:

A & F B5R + 7 parts pVAX
B & G A27L, B5R, H3L, L1R + 4 parts pVAX
C & H A56R, A4L, A27L, A33R, B5R, F9L, H3L, L1R
D & I Negative control – 8 parts pVAX
E & J A56R, A4L, A27L, A33R, B5R, F9L, H3L, L1R w/o EP

FIG. 35b1

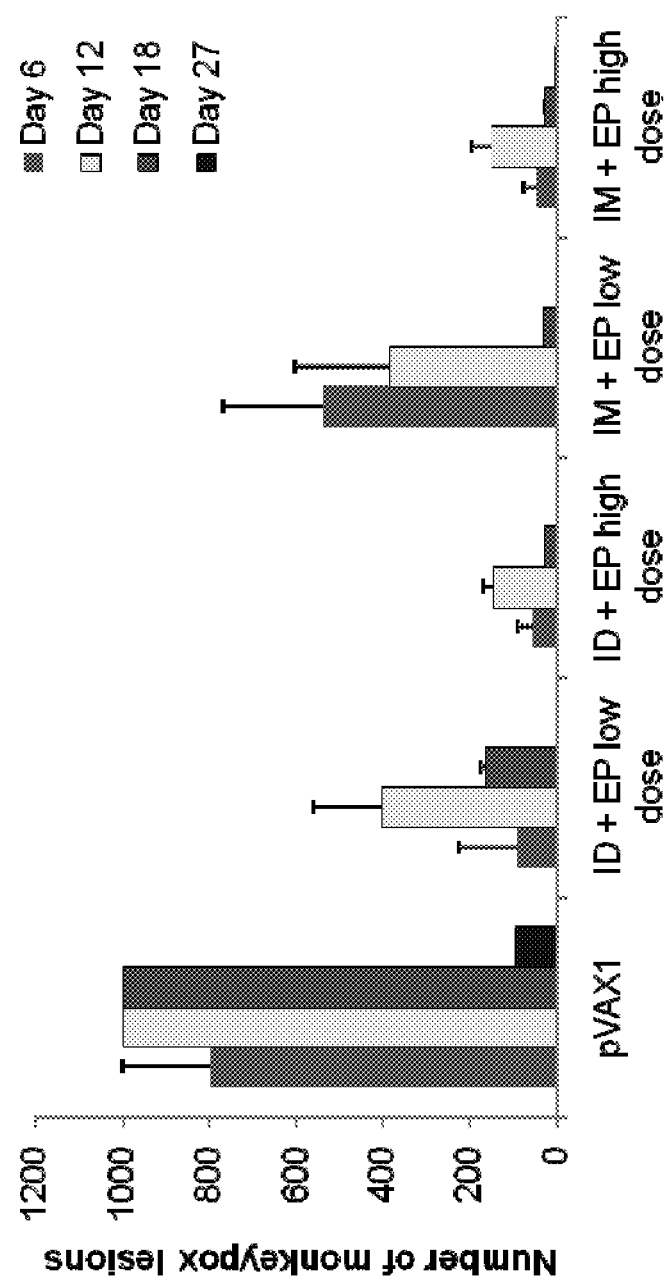
FIG. 35b2

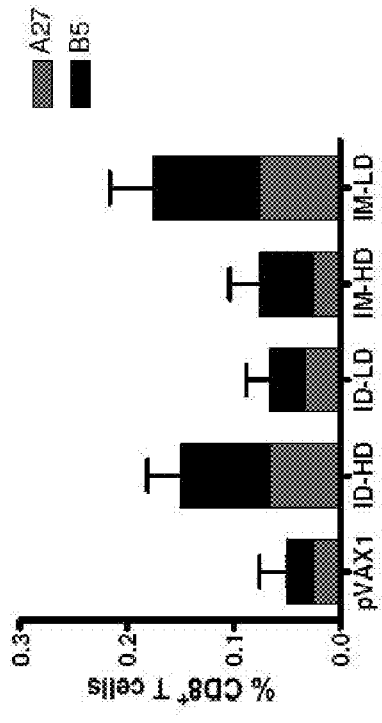
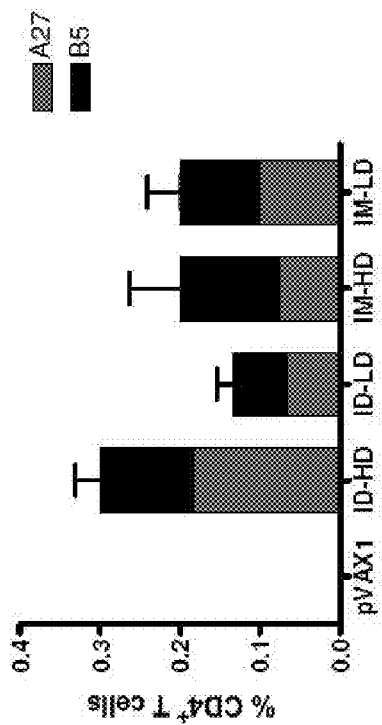
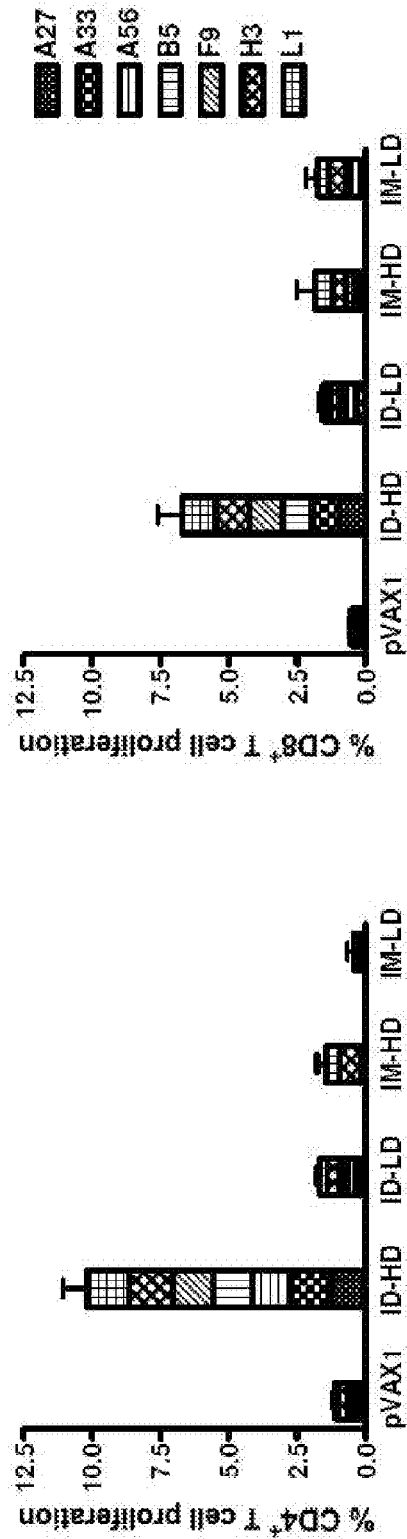

US 8,535,687 B2

SMALLPOX DNA VACCINE AND THE ANTIGENS THEREIN THAT ELICIT AN IMMUNE RESPONSE

CROSS-REFERENCE TO RELATED APPLICATIONS

This application claims the benefit of U.S. Provisional Application No. 61/056,687, filed May 28, 2008 and U.S. Provisional Application No. 61/121,054, filed Dec. 9, 2008, the contents of which is incorporated herein by reference in it's entirety.

STATEMENT REGARDING FEDERALLY FUNDED RESEARCH

The U.S. Government has a paid-up license in this invention and the right in limited circumstances to require the patent owner to license other on reasonable terms as provided for by the terms of contract number HDTRA 1-07-C-0104 awarded by the Department of Defense.

FIELD OF INVENTION

The present invention relates to consensus smallpox antigens, nucleic acid constructs encoding such antigens, and vaccines made therefrom for generating an immune response against smallpox virus, and methods for using these products to protect mammals against smallpox virus.

BACKGROUND

For the most part of the last quarter century, little public or scientific attention focused on issues relating to smallpox or smallpox vaccination but due to current concerns regarding bioterrorism, the potential threat from an outbreak of smallpox through deliberate release has become a real concern. There are several factors that make smallpox a terror weapon of choice. Smallpox can be produced in large quantities, is stable for storage and transportation and can be produced as an aerosol that has a 30% mortality rate in exposed non-vaccinated individuals. It is highly infectious, as 10-20 or more cases can be attributed to have originated from one infected individual. Accordingly, there are great concerns that if a terrorist attack releases smallpox, many U.S. populations will be at risk for infection, disease and death.

The commercially approved smallpox vaccines available for limited use are the established Dryvax vaccine and the Acambis vaccine. This Wyeth vaccine is a lyophilized preparation of live vaccinia virus (VACV) derived from calf lymph. Wyeth discontinued distribution of smallpox vaccine to civilians in 1983. The Acambis vaccine is a live tissue culture adapted vaccine stock that still is associated with severe adverse effects in humans. In the past there were concerns regarding the risks associated with Dryvax. These concerns are heightened by recent adverse events in clinical studies. An important concern is that there are a significant number of immunocompromised (HIV-infected individuals) and a much larger elderly population than was present in 1970. Furthermore pregnant women, intravenous drug users, transplant recipients, and individuals on immunosuppressive drugs living in North America are potential vaccine recipients and are all at increased risk from the original Dryvax or recent Acambis live vaccine strategies. In North America, a concern that an unacceptable number of people may be hospitalized due to serious complications is of major significance. Many people could die from the vaccine alone or, in the case of a bioterror attack using smallpox, there may be slow deployment or non-compliance due to vaccine-related health concerns. Although the recent smallpox vaccination programs are intended to protect against bioterror events, naturally occurring poxvirus diseases are also a growing concern because the number of persons with VACV-induced immunity has been in decline.

Cidofovir, a licensed drug for the treatment of cytomegalovirus retinitis in AIDS patients has broad-spectrum activity against virtually all DNA viruses. Recently, cidofovir demonstrated in vitro and in vivo activity in mice against a number of poxviruses including *variola* and monkeypox (MPXV). A single dose of cidofovir showed high efficacy in protecting mice from lethal respiratory infection with either vaccinia or cowpox, provided drug treatment is initiated within a few days after exposure.

Still, the current therapies have their limitations. The use of currently stockpiled vaccines to manage a significantly higher rate of complications than occurred in the 1960s is likely not effective, as demands may not be met and efficacy can be reduced due to the evolution of the small pox virus in recent times. There are also the aforementioned safety concerns with individuals that are immunocompromised or have weakened health. The viability of DNA based vaccines is thought to be a potential platform for vaccines, but yet to be proven successful on humans. And further, because smallpox virus is a highly complex DNA virus that encodes over 200 genes and has two infectious forms, the mature virion (MV) and the enveloped virion (EV) each with its own unique set of membrane glycoproteins and different requirements for entry, candidate antigens for developing an effective DNA vaccine has been difficult.

There still remains a need for a safe and effective alternative for current smallpox vaccines. Further, there is a need for a smallpox vaccine that is well tolerated and provides broad immunoprotection, and can be manufactured in large scale in a timely manner in response to bioterror threats.

SUMMARY OF THE INVENTION

An aspect of the present invention comprises DNA vaccines that are capable of generating a protective immune response in mammals against a smallpox virus. The DNA vaccine comprises at least one DNA plasmid capable of expressing a plurality of VACV MV antigens, and at least one DNA plasmid capable of expressing a plurality of VACV EV antigens. Preferably, the DNA vaccines further include a plasmid capable of expressing A4L antigen. Another aspect of the present invention relates to methods of inducing a protective immune response in a mammal to smallpox virus, including a neutralizing antibody response, comprising: injecting into tissue of said mammal a DNA vaccine comprising at least one DNA plasmid capable of expressing a plurality of VACV MV antigens, at least one DNA plasmid capable of expressing a plurality of VACV EV antigens, and a DNA plasmid capable of expressing A4L. Preferably, the methods further comprise the step of electroporating said tissue with an electroporating amount of electrical energy.

BRIEF DESCRIPTION OF DRAWINGS

The numerous objects and advantages of the present invention may be better understood by those skilled in the art by reference to the accompanying figures, in which:

FIG. 1 displays a table of lots of smallpox Plasmid-Based manufacturing along with a summary of their physical and chemical characteristics.

FIG. 3 displays a plasmid map pGX4002 that expresses A27L antigen, including consensus, human-codon optimized A27L (encoding DNA sequence set forth as SEQ ID NO.: 3).

FIG. 4 displays a plasmid map pGX4003 that expresses B5R antigen, including consensus, human-codon optimized B5R (encoding DNA sequence set forth as SEQ ID NO.: 5).

FIG. 7 displays a plasmid map pGX4006 that expresses F9L antigen, including consensus, human-codon optimized F9L (encoding DNA sequence set forth as SEQ ID NO.: 11).

FIG. 9 displays a plasmid map pGX4008 that expresses L1R antigen, including consensus, human-codon optimized L1R (encoding DNA sequence set forth as SEQ ID NO.: 15).

FIG. 17 displays a timeline showing the chronology of events in study comparing delivery of antigens either intradermally (ID) or intramuscularly (IM) in rabbits.

FIG. 18 displays a table that provides the electroporation and delivery conditions of multiple plasmids given to rabbits of each one of groups A through J.

FIG. 22 displays a timeline showing the IM or ID vaccination schedule of rabbits.

FIG. 23 displays a table that provides electroporation and delivery conditions of multiple plasmids given to rabbits of each one of groups A through J.

Figure 24:
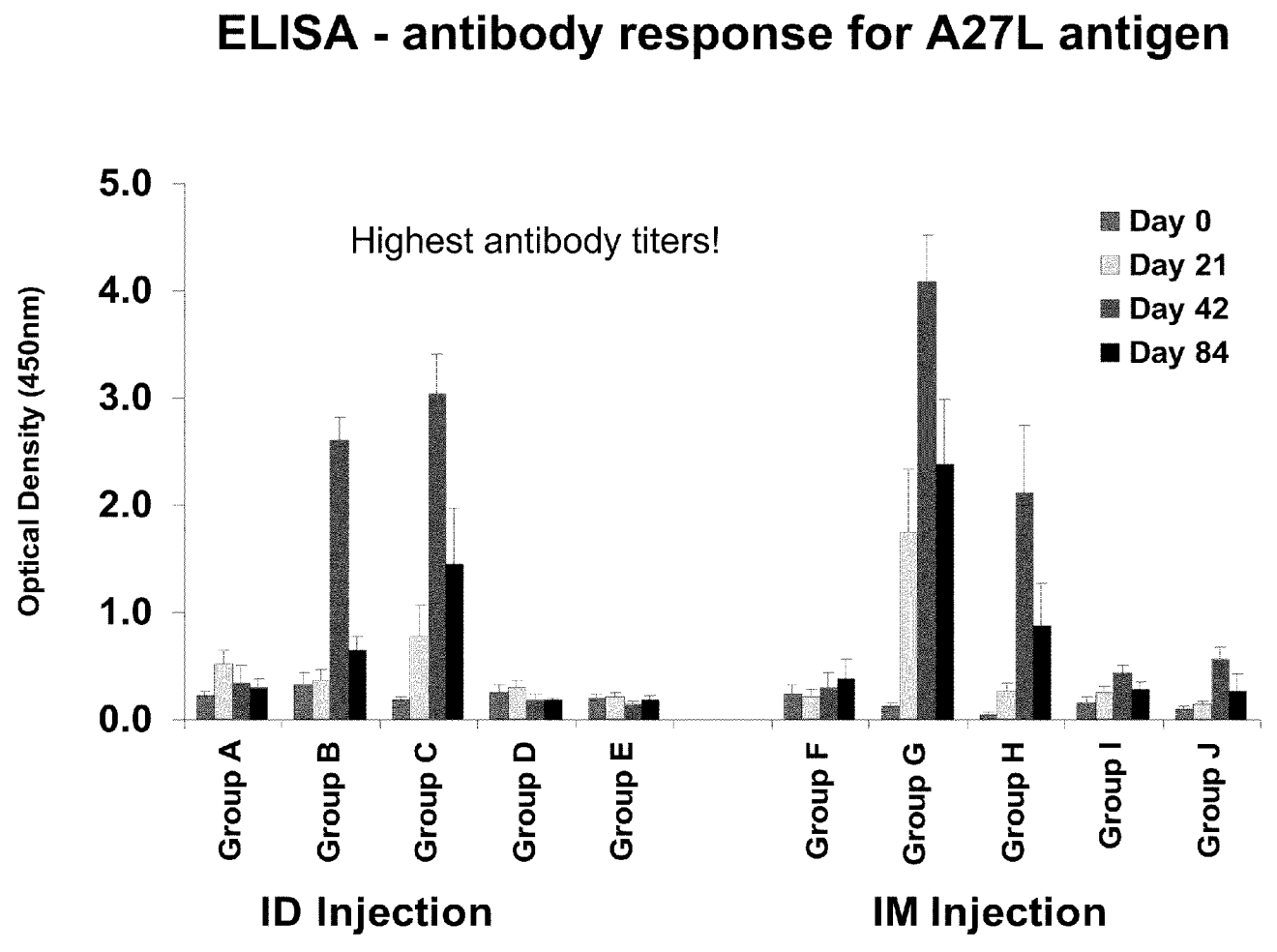

FIG. 24 displays a bar graph showing the antibody response for A27L antigen in rabbits of various groups.

Figure 27:
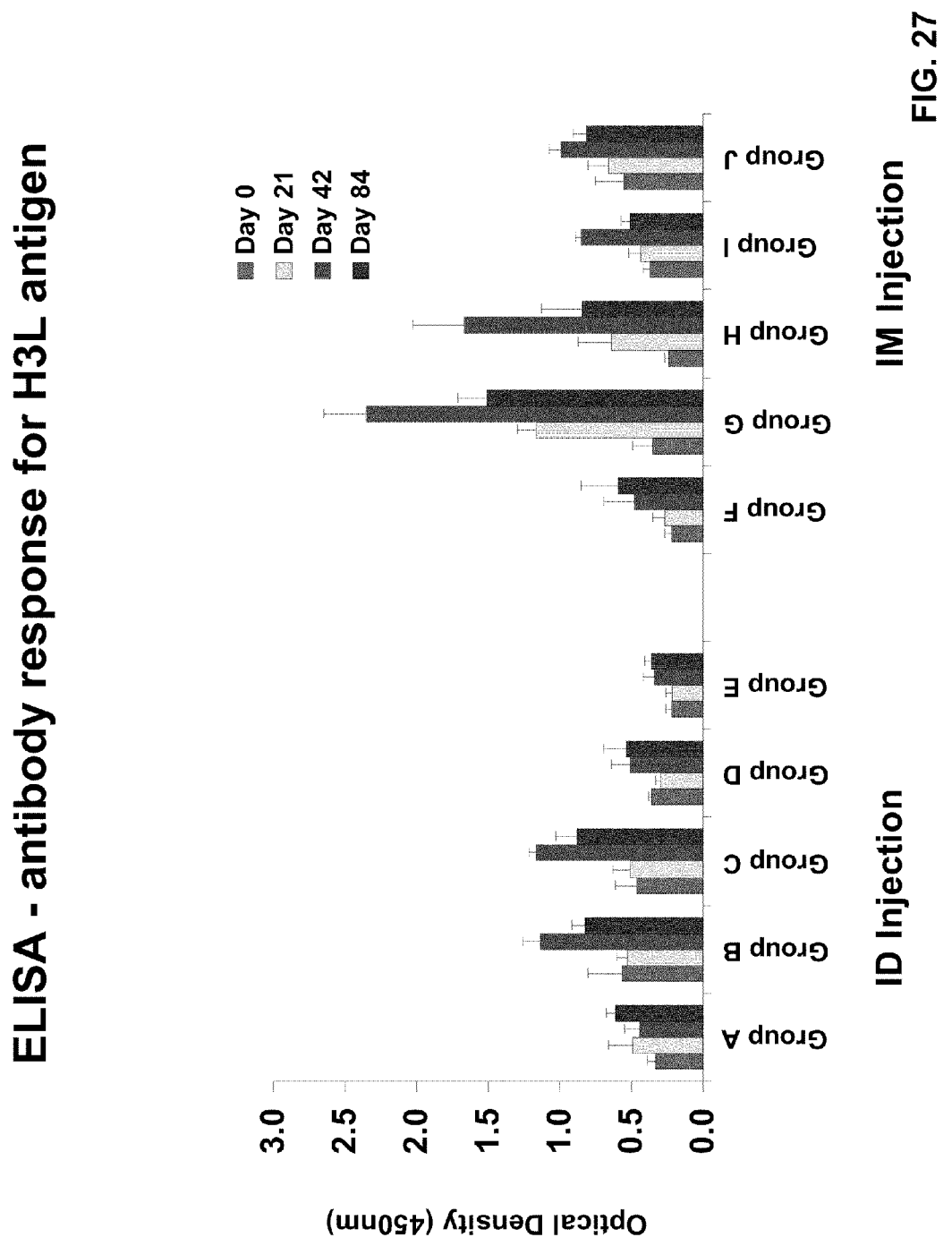

FIG. 27 displays a bar graph showing the antibody response for H3L antigen in rabbits of various groups.

FIG. 34 Enhanced antibody and cellular response after ID and IM delivery for each vaccination. Cynomolgus macaques were vaccinated on Days 0, 28, and 56.

DETAILED DESCRIPTION OF PREFERRED EMBODIMENTS

Figure 2:
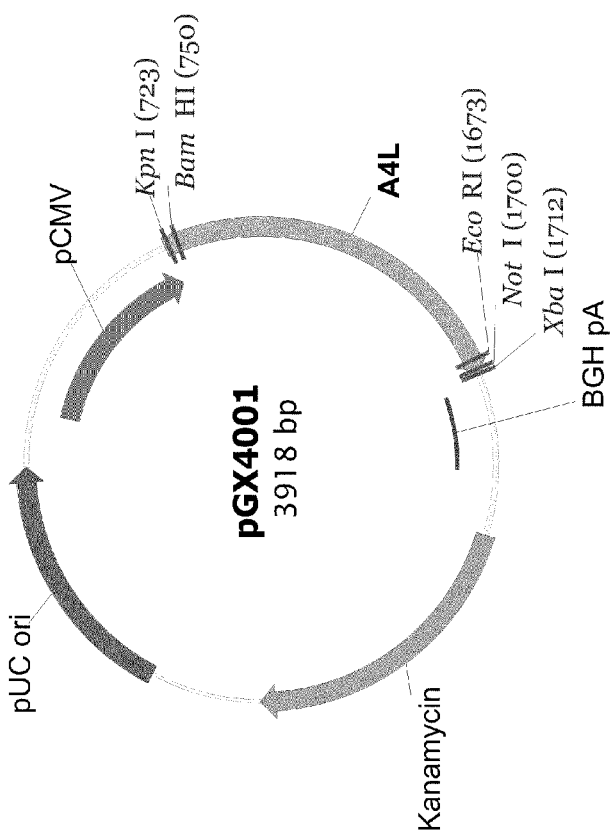
FIG. 2 displays a plasmid map pGX4001 that expresses A4L antigen, including consensus, human-codon optimized A4L (encoding DNA sequence set forth as SEQ ID NO.: 1).
Figure 5:
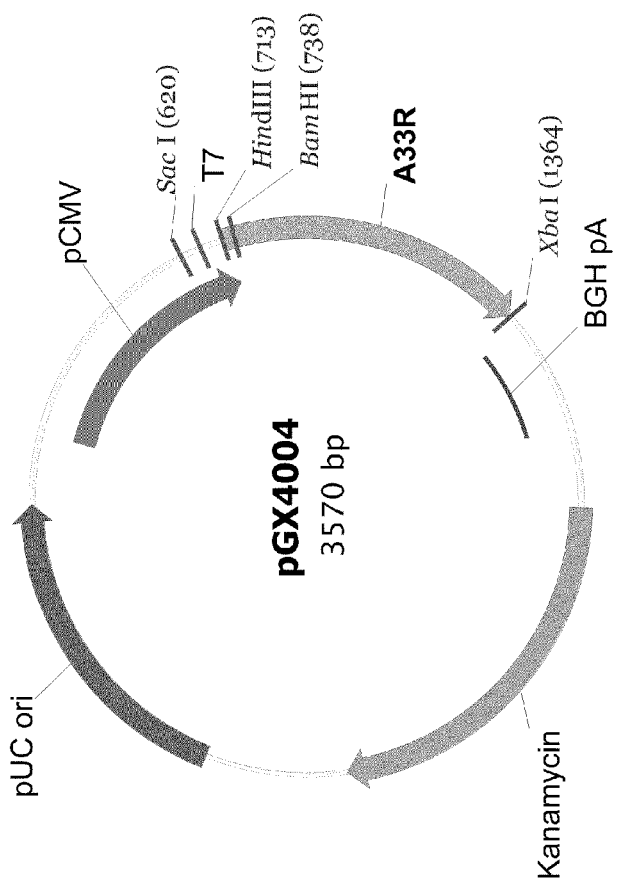
FIG. 5 displays a plasmid map pGX4004 that expresses A33R antigen, including consensus, human-codon optimized A33R (encoding DNA sequence set forth as SEQ ID NO.: 7).
Figure 6:
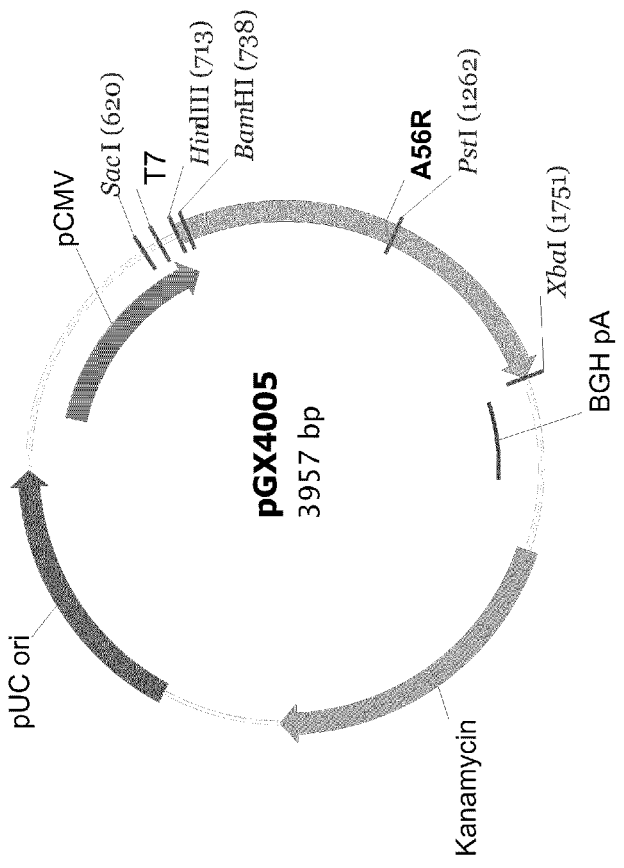
FIG. 6 displays a plasmid map pGX4005 that expresses A56R antigen, including consensus, human-codon optimized A56R (encoding DNA sequence set forth as SEQ ID NO.: 9).
Figure 8:
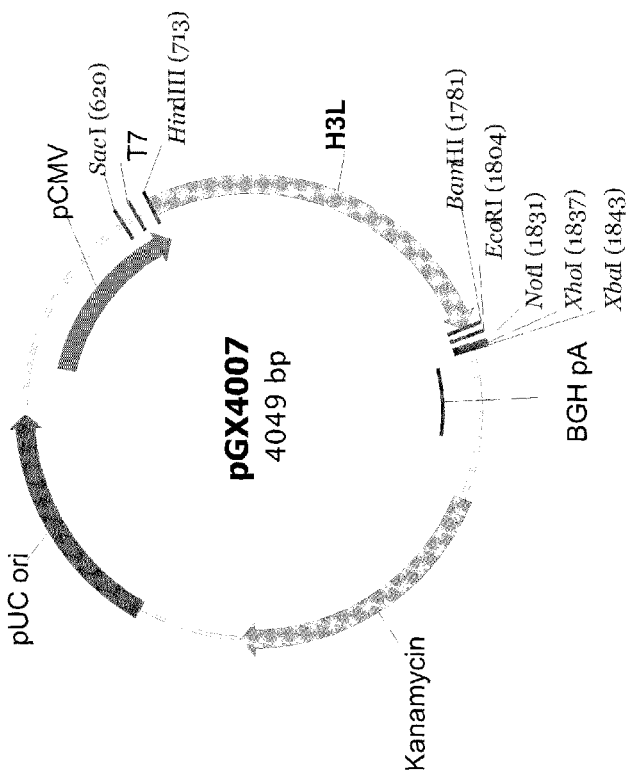
FIG. 8 displays a plasmid map pGX4007 that expresses H3L antigen, including consensus, human-codon optimized H3L (encoding DNA sequence set forth as SEQ ID NO.: 13).
Figure 10:
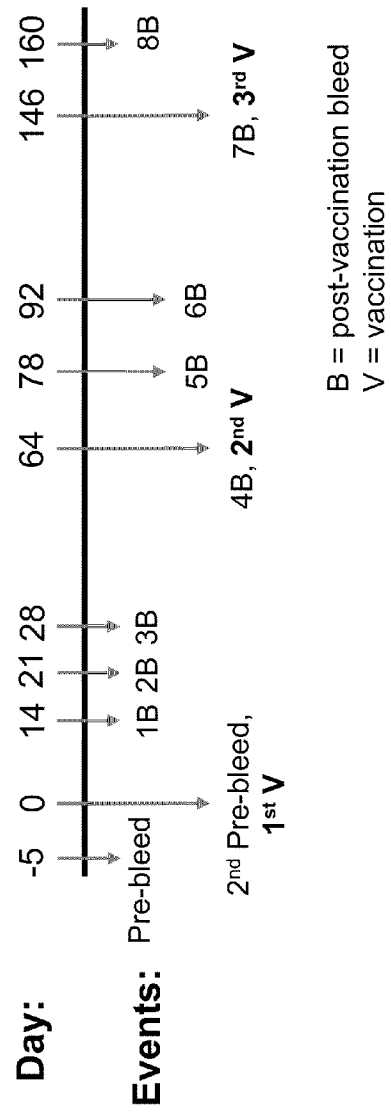
FIG. 10 displays a timeline showing the chronology of events in a pilot study in rabbits.
Figure 11:
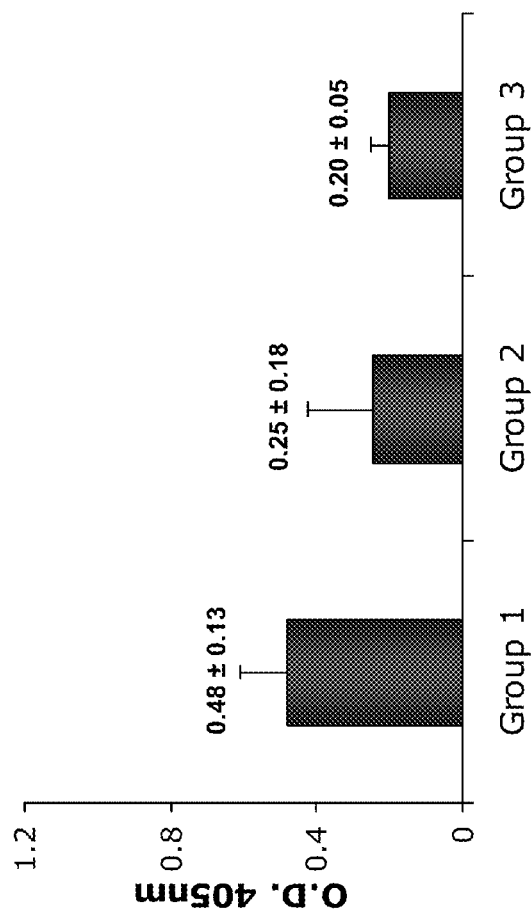
FIG. 11 displays a bar graph showing the B5R antibody response in rabbits from three different groups.
Figure 12:
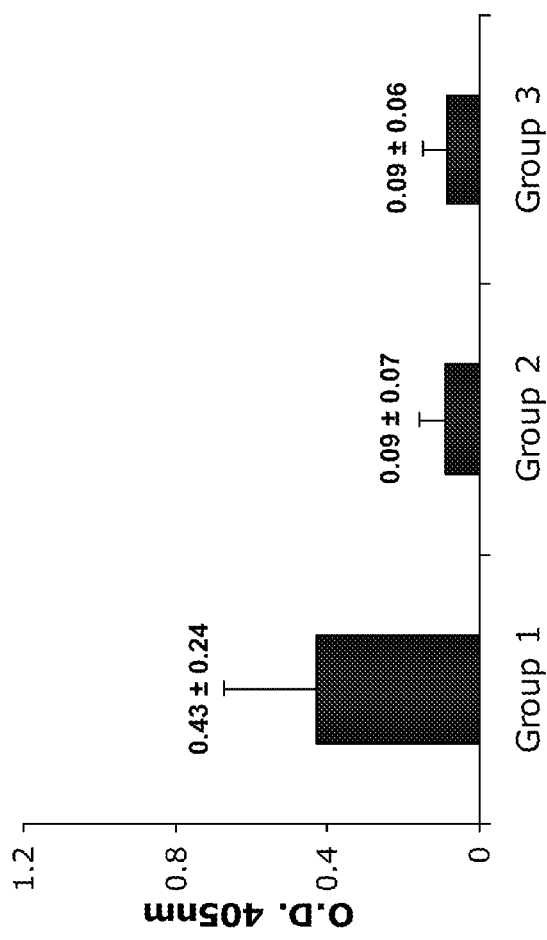
FIG. 12 displays a bar graph showing the H3L antibody response in rabbits from three different groups.
Figure 13:
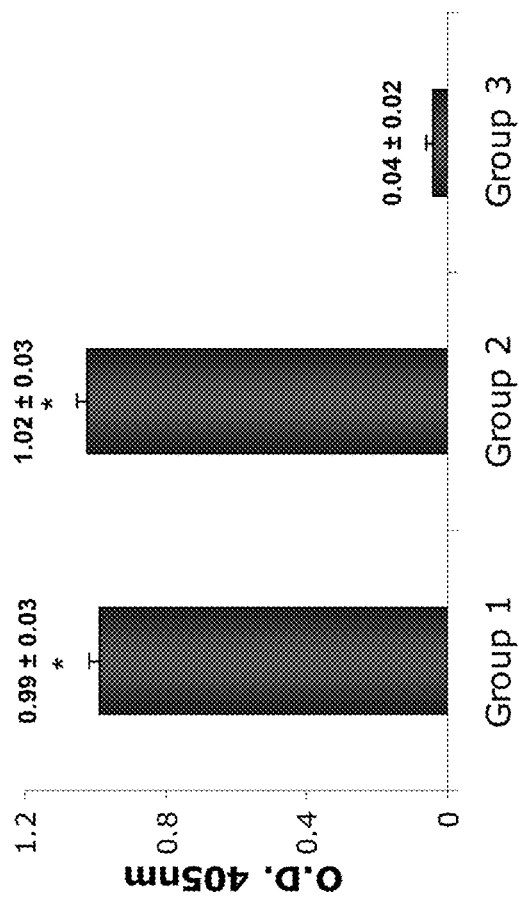
FIG. 13 displays a bar graph showing the A27L antibody response in rabbits from three different groups.
Figure 14:
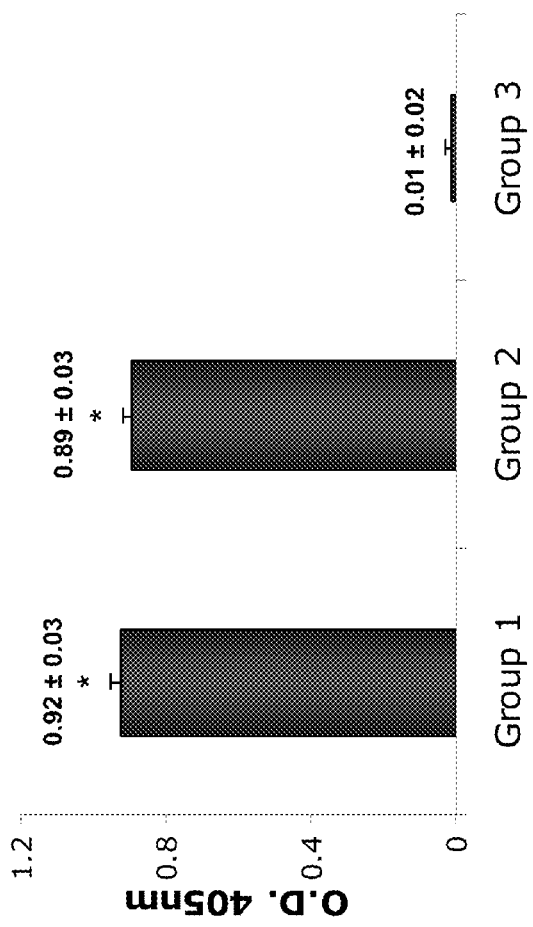
FIG. 14 displays a bar graph showing the L1R antibody response in rabbits from three different groups.
Figure 15:
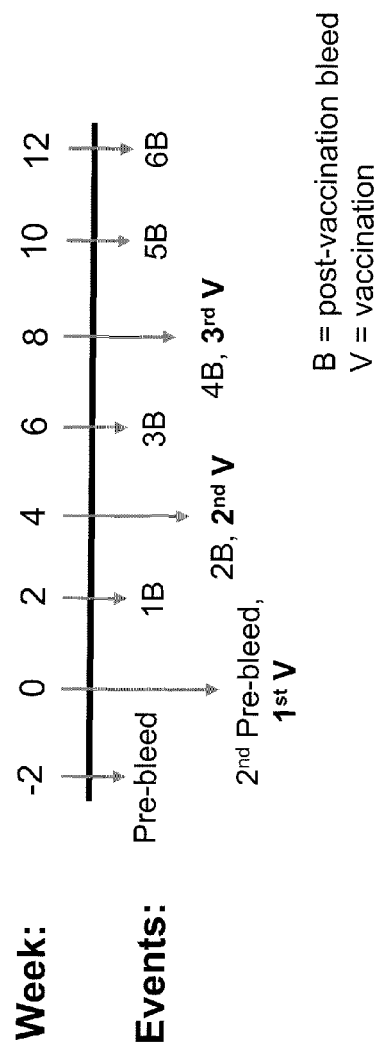
FIG. 15 displays a timeline showing the chronology of events in a pilot study in cynomolgus macaques (non-human primates).
Figure 16:
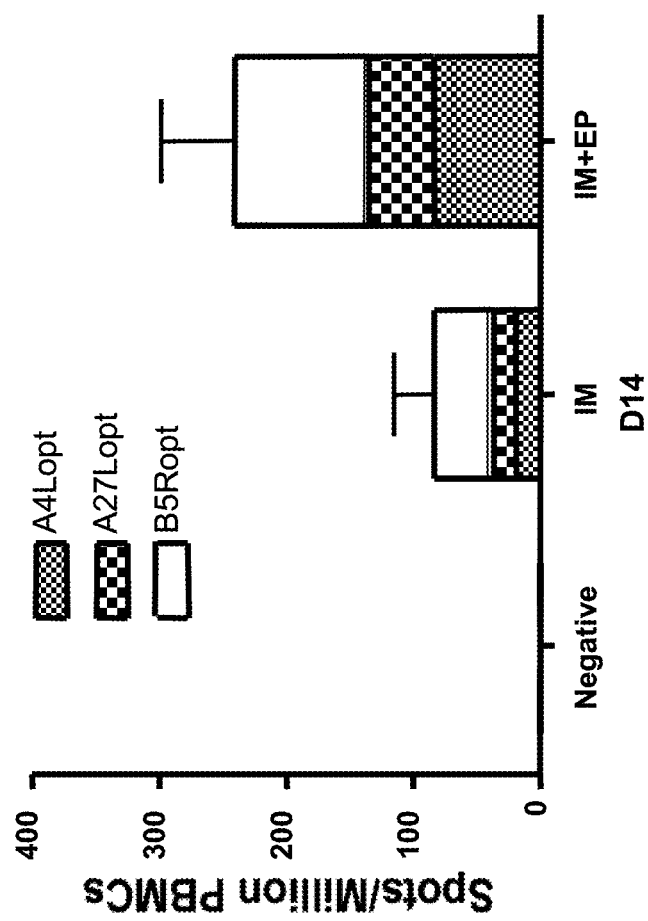
FIG. 16 displays a bar graph showing the ELISpot results for three groups of primates.
Figure 19:
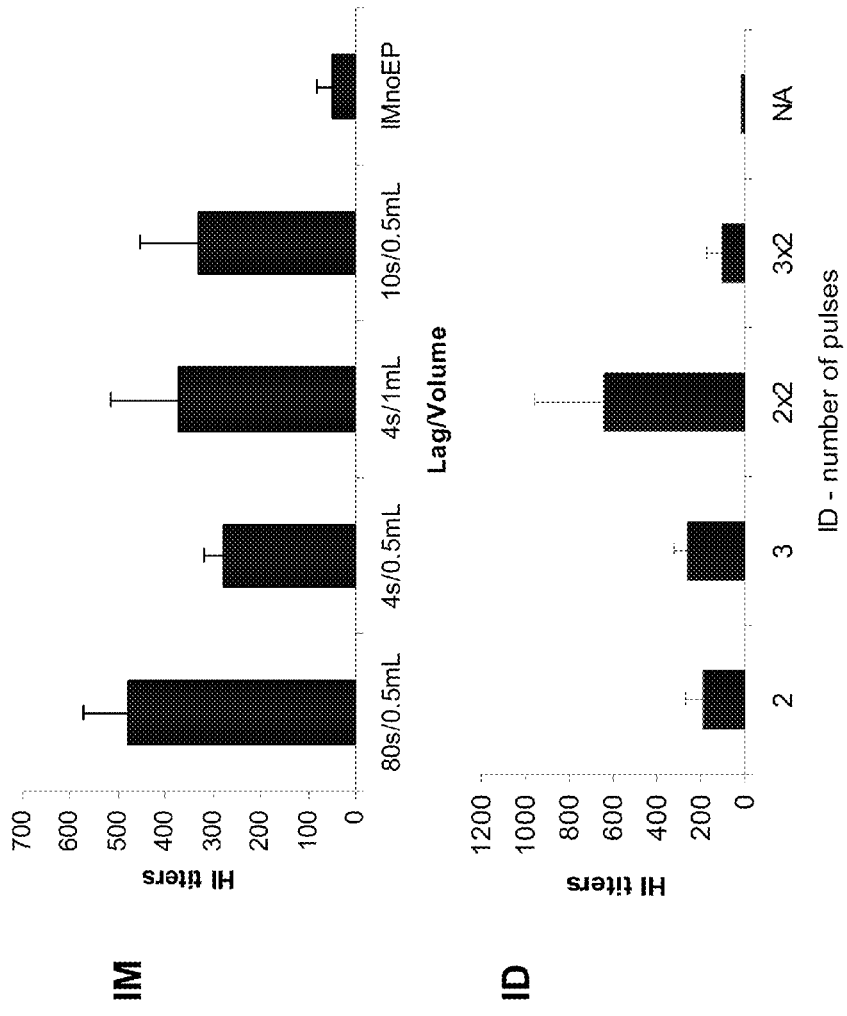
FIG. 19 displays a bar graph showing antibody titers (HA antigen) under various IM or ID conditions.
Figure 20:
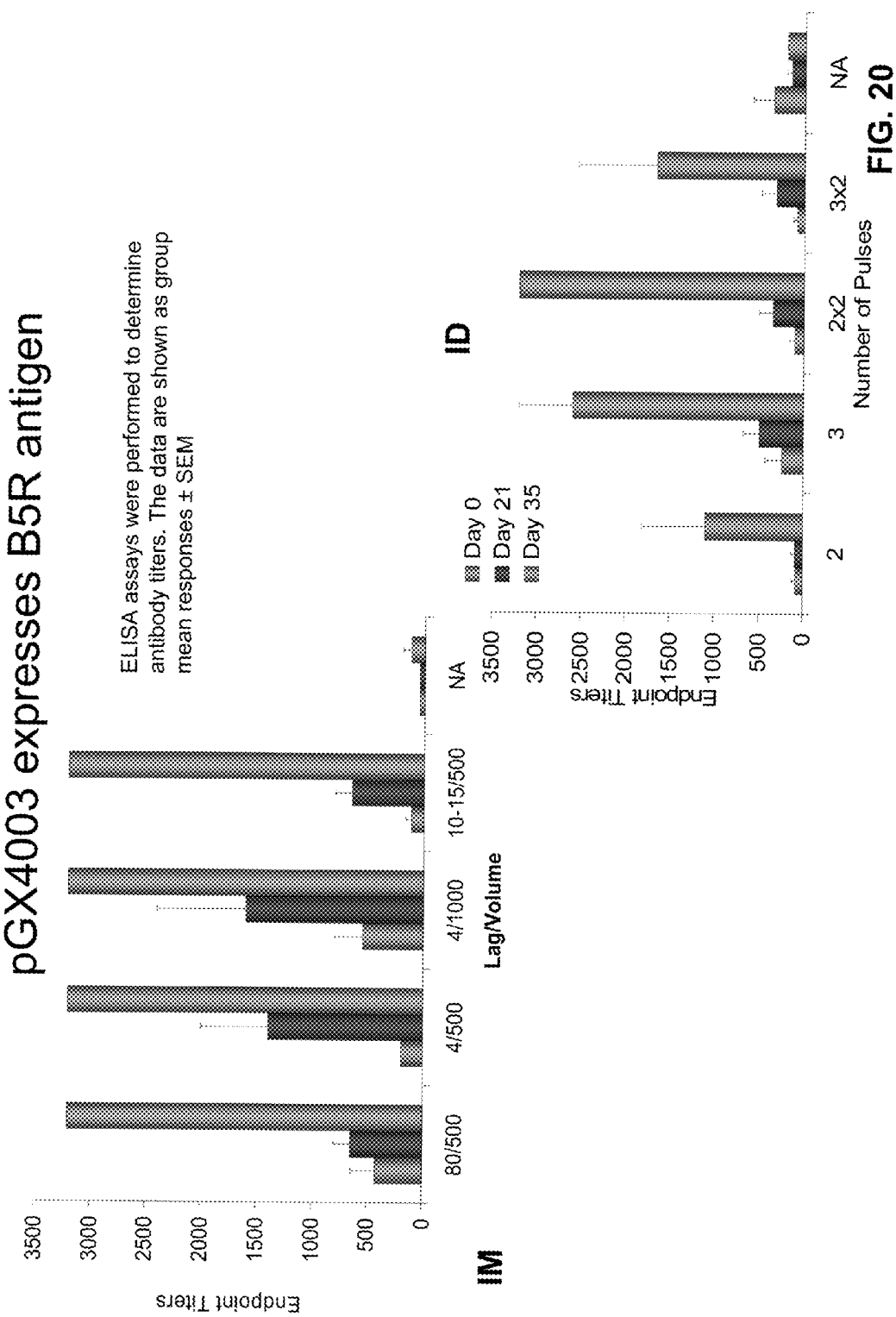
FIG. 20 displays a bar graph showing antibody titers (B5R antigen) under various IM or ID conditions.
Figure 21:
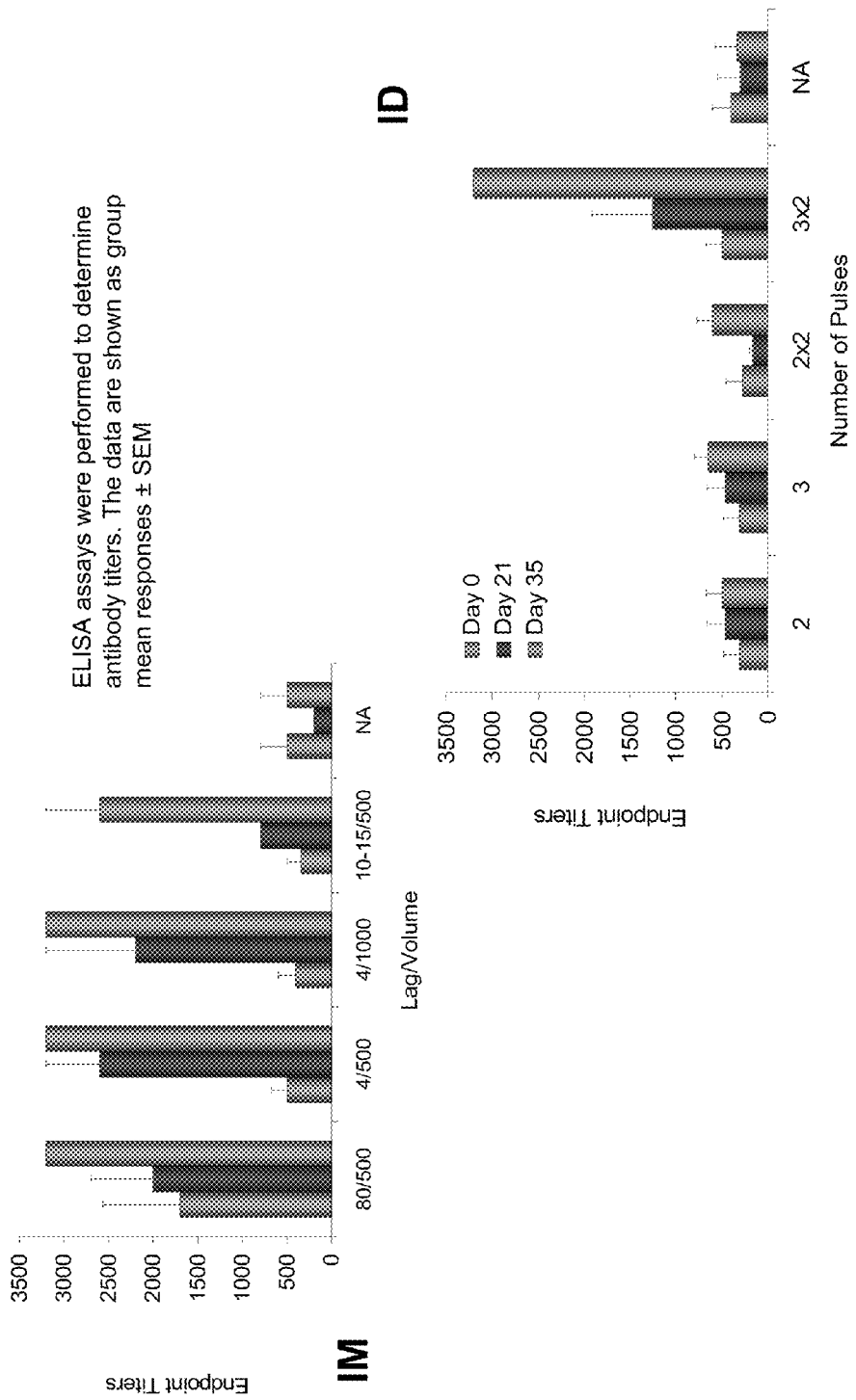
FIG. 21 displays a bar graph showing antibody titers (A27L antigen) under various IM or ID conditions.
Figure 25:
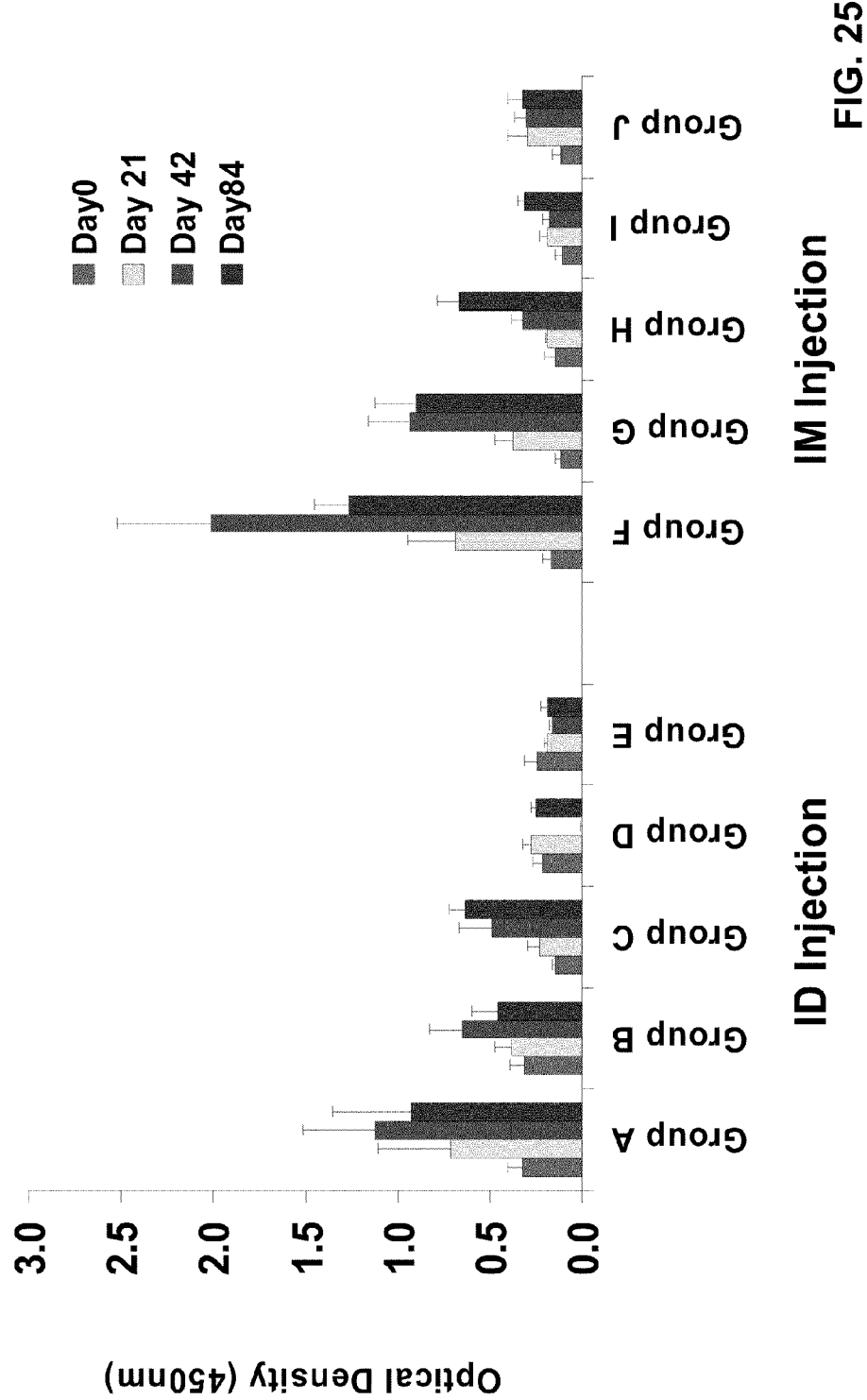
FIG. 25 displays a bar graph showing the antibody response for B5R antigen in rabbits of various groups.
Figure 26:
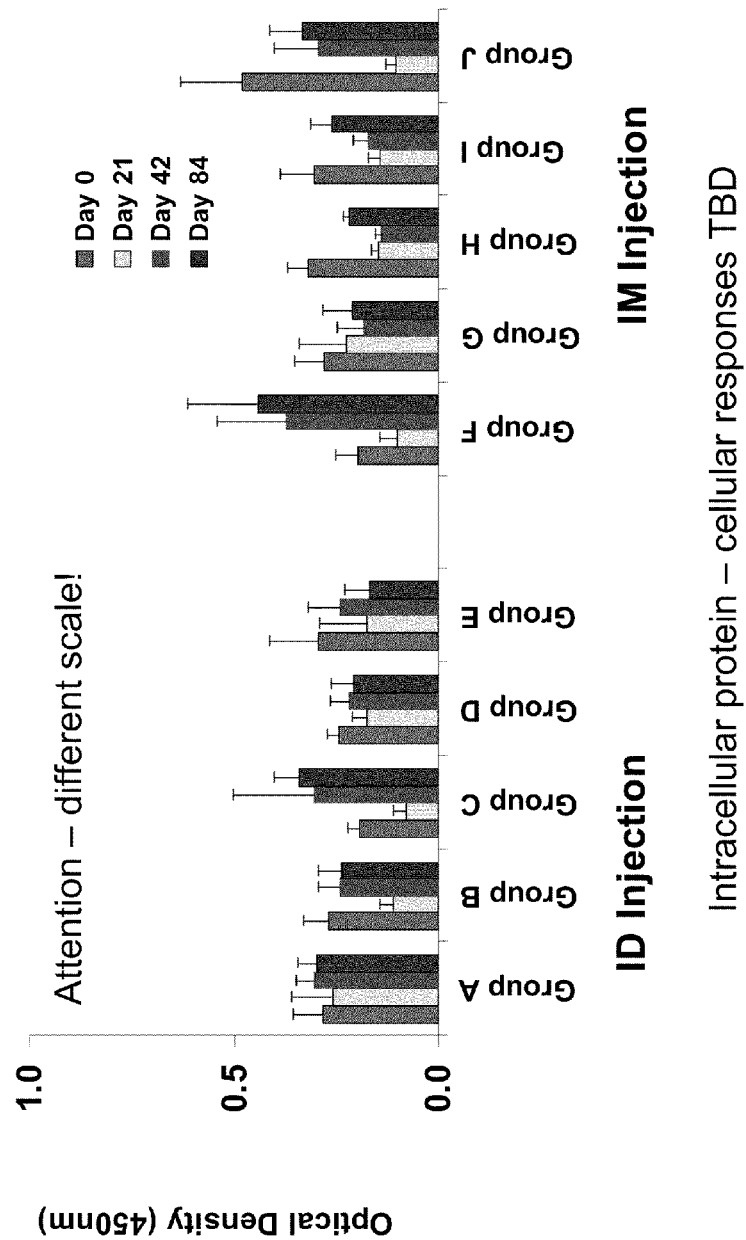
FIG. 26 displays a bar graph showing the antibody response for A4L antigen in rabbits of various groups.
Figure 28:
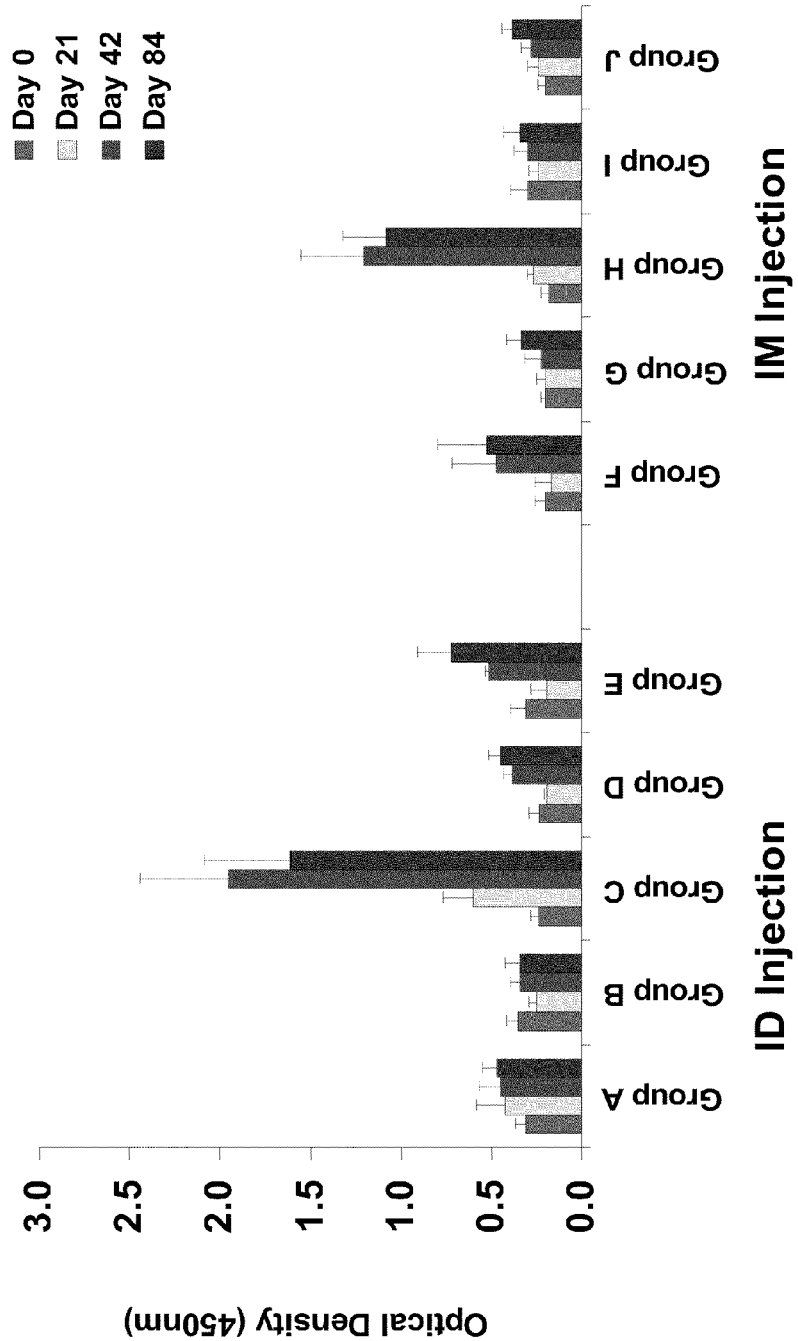
FIG. 28 displays a bar graph showing the antibody response for A33R antigen in rabbits of various groups.
Figure 29:
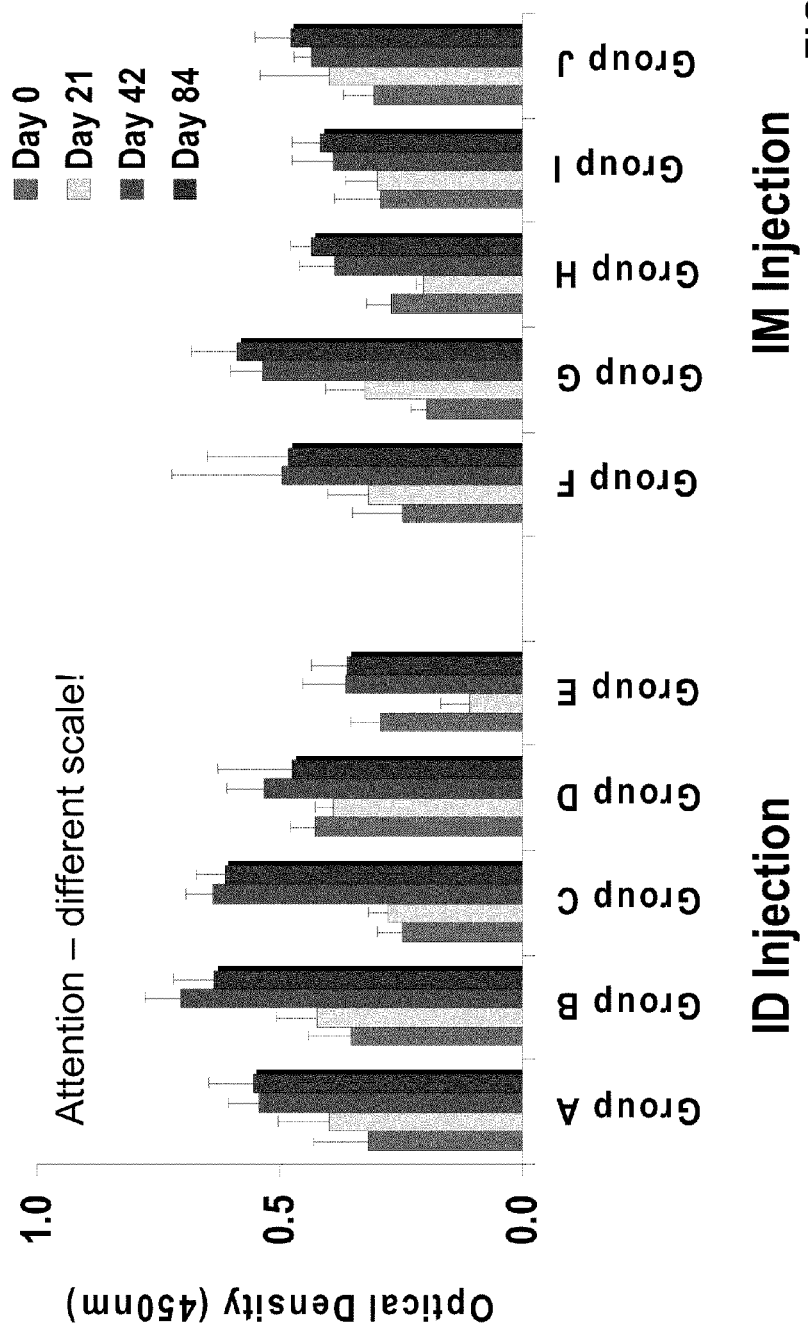
FIG. 29 displays a bar graph showing the antibody response for L1R antigen in rabbits of various groups.
Figure 30:
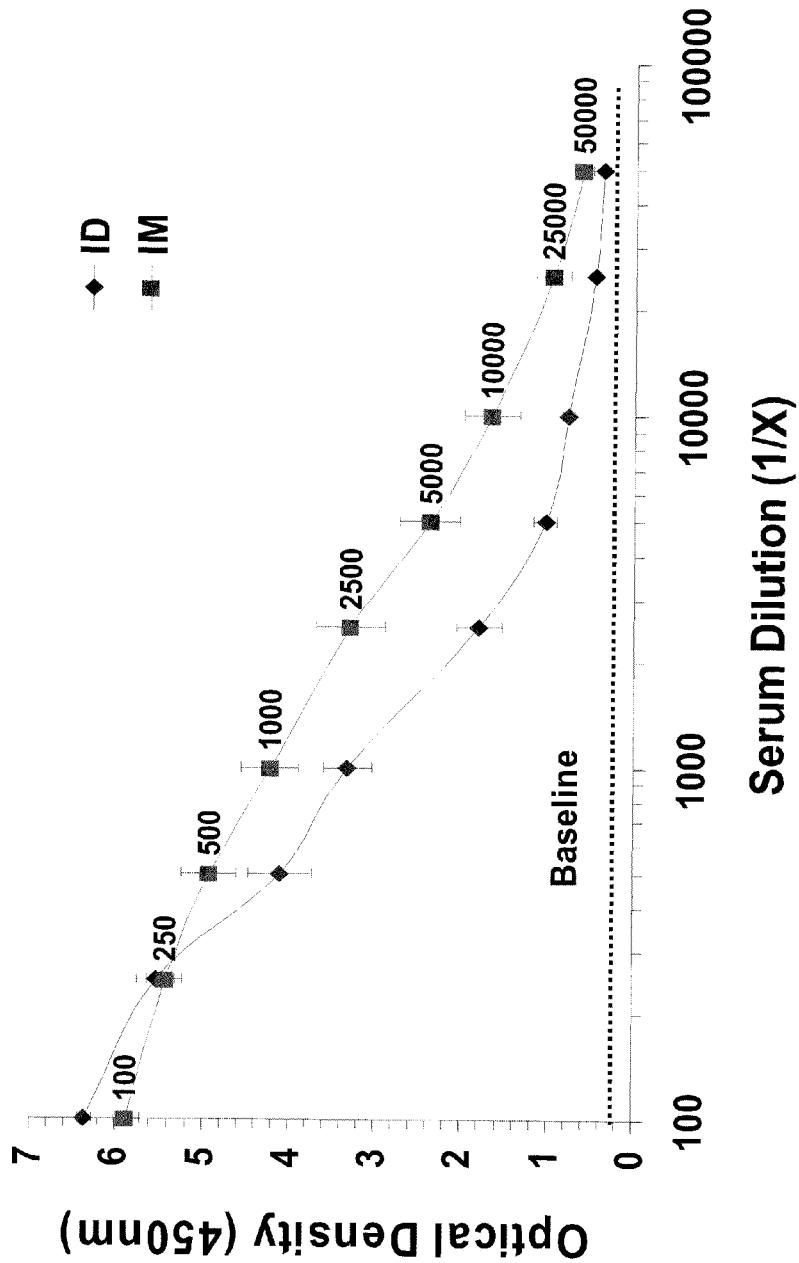
FIG. 30 displays a line graph showing an endpoint ELISA curve against A27L antigen for a four plasmid combination at day 42.
Figure 31:
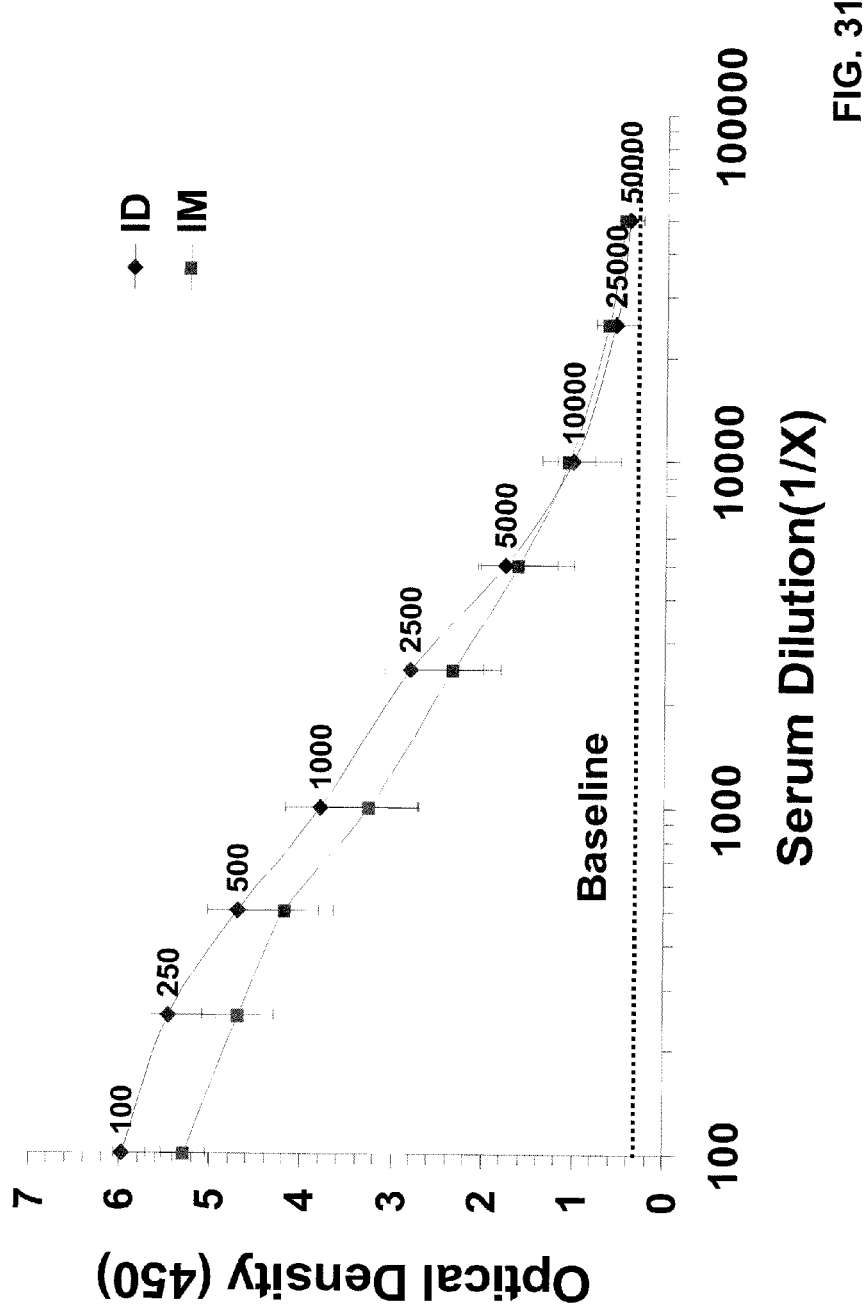
FIG. 31 displays a line graph showing an endpoint ELISA curve against A27L antigen for an eight plasmid combination at day 42.
Figure 32:
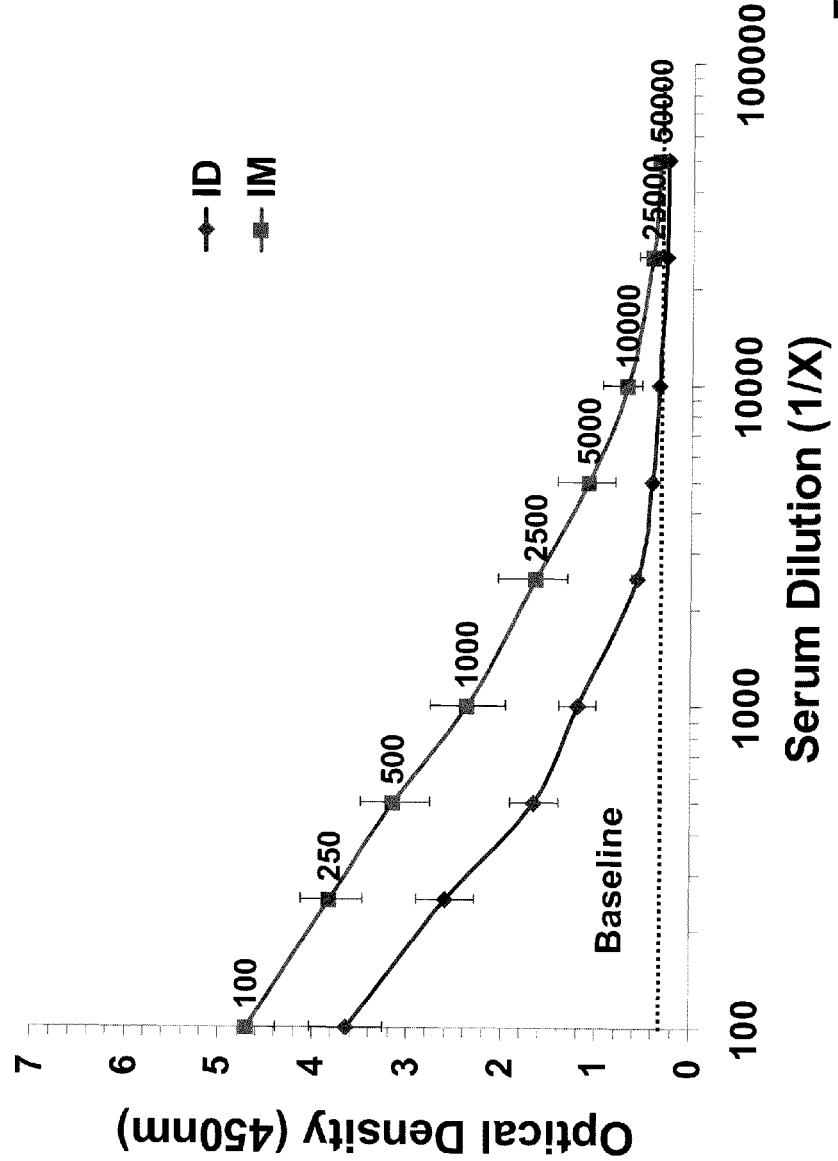
FIG. 32 displays a line graph showing an endpoint ELISA curve against A27L antigen for a four plasmid combination at day 84.
Figure 33:
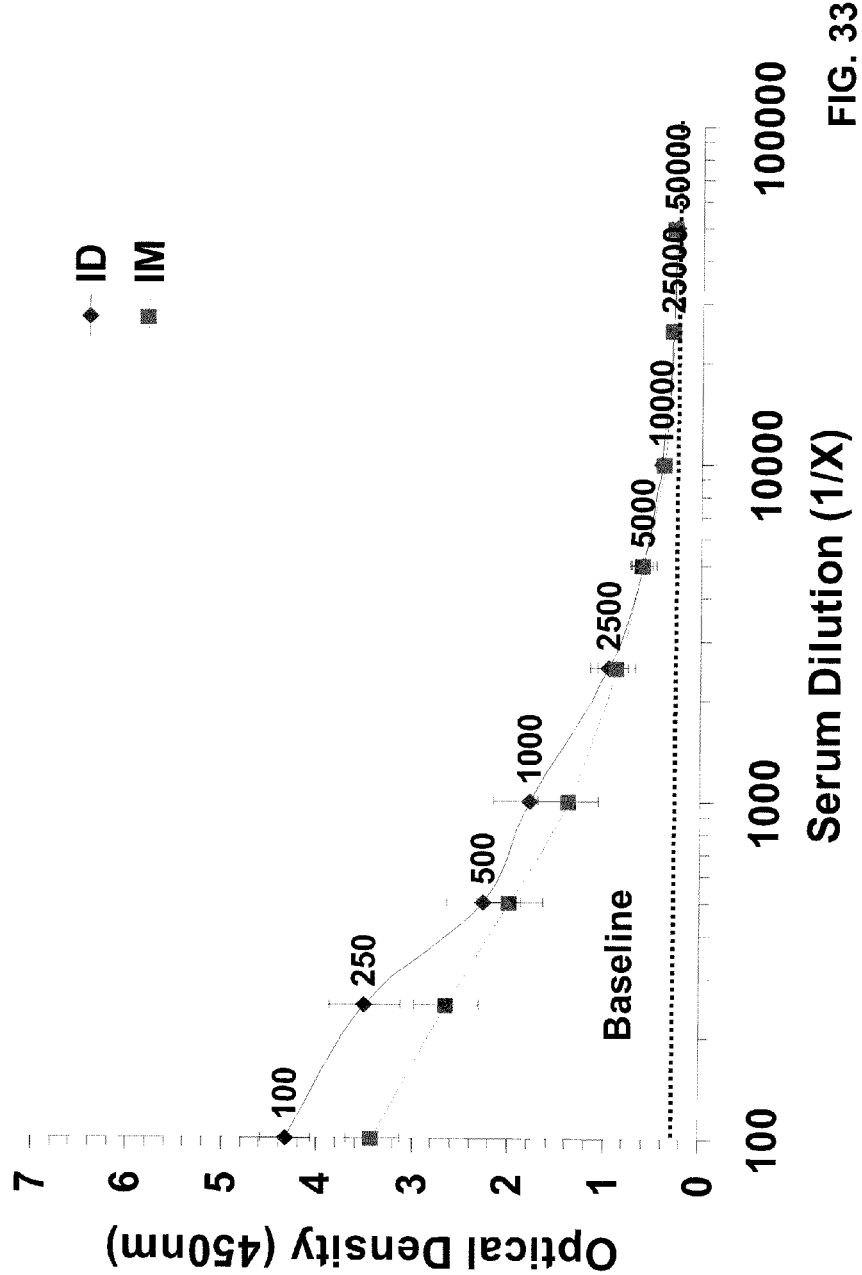
FIG. 33 displays a line graph showing an endpoint ELISA curve against A27L antigen for an eight plasmid combination at day 84.

The following abbreviated, or shortened, definitions are given to help the understanding of the preferred embodiments of the present invention. The abbreviated definitions given here are by no means exhaustive nor are they contradictory to the definitions as understood in the field or dictionary meaning. The abbreviated definitions are given here to supplement or more clearly define the definitions known in the art.

Definitions

As used herein, the term "nucleic acid construct" refers to the DNA or RNA molecules that comprise a nucleotide sequence that encodes protein. The coding sequence, or "encoding nucleic acid sequence," can include initiation and termination signals operably linked to regulatory elements including a promoter and polyadenylation signal capable of directing expression in the cells of the individual to whom the nucleic acid molecule is administered.

As used herein, the term "expressible form" refers to nucleic acid constructs that contain the necessary regulatory elements operably linked to a coding sequence that encodes a protein such that when present in the cell of the individual, the coding sequence will be expressed.

The term "constant current" is used herein to define a current that is received or experienced by a tissue, or cells defining said tissue, over the duration of an electrical pulse delivered to same tissue. The electrical pulse is delivered from the electroporation devices described herein and contemplated for use with the plasmids and vaccines described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

The term "feedback" or "current feedback" is used interchangeably and means the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. Preferably, the feedback is accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. In some embodiments, the feedback loop is instantaneous as it is an analog closed-loop feedback.

The terms "electroporation," "electro-permeabilization," or "electro-kinetic enhancement" ("EP"), as used interchangeably herein, refer to the use of a transmembrane electric field pulse to induce microscopic pathways (pores) in a bio-membrane; their presence allows biomolecules such as plasmids, oligonucleotides, siRNA, drugs, ions, and/or water to pass from one side of the cellular membrane to the other.

The term "decentralized current" is used herein to define the pattern of electrical currents delivered from the various needle electrode arrays of the electroporation devices described herein, wherein the patterns minimize, or preferably eliminate, the occurrence of electroporation related heat stress on any area of tissue being electroporated.

The term "feedback mechanism" as used herein refers to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. The term "impedance" is used herein when discussing the feedback mechanism and can be converted to a current value according to Ohm's law, thus enabling comparisons with the preset current. In a preferred embodiment, the "feedback mechanism" is performed by an analog closed loop circuit.

The term "adjuvant" is used herein to mean any molecule added to the DNA vaccines described herein to enhance antigenicity of the VACV antigen encoded by the DNA plasmids and encoding nucleic acid sequences described hereinafter.

The term "protective immune response" is used herein to mean a combination of antibody response along with cellular immune response, and preferably neutralizing antibody response, which results from immunization with the DNA vaccines provided herein.

The term "consensus" or "consensus sequences" or "consensus antigens", used interchangeable to describe the preferred antigens of the present invention, refers to a synthetic sequence that is generated based on contemporary isolates of a particular virus. The consensus may be genetically closer to current circulating viral strains than any given natural virus isolate. However, since global sequencing is generally conducted with viruses sampled during chronic infections instead of viruses sampled during acute infection, developing a consensus vaccine response on epitopes that for the most part have escaped may be a disadvantage. To minimize this disadvantage, one useful strategy for vaccine design would be to take early transmitter sequences into account. The consensus becomes an effective approach to minimize the degree of sequence dissimilarity between a vaccine strain and contemporary circulating viruses is to create artificial sequences that are "central" to these viruses. One design strategy is to use a consensus sequence derived from the most common amino acid in every position in an alignment. Such consensus can then elicit a broad immune response against various natural viral isolates and polymorphisms in combinations not found in any natural virus.

An aspect of the present invention comprises DNA vaccines that are capable of generating a protective immune response in mammals against a pox virus. Preferably the pox virus is smallpox virus. The DNA vaccine comprises at least one DNA plasmid capable of expressing a plurality of VACV MV antigens, and at least one DNA plasmid capable of expressing a plurality of VACV EV antigens. Preferably, the DNA vaccines further includes a plasmid capable of expressing A4L antigen. Each of said antigens can be expressed by a single DNA plasmid (includes multiple encoding sequences) or by distinct DNA plasmids. Preferably, each distinct antigen will be expressed by a distinct DNA plasmid. The VACV MV antigens comprise: A27L, F9L, H3L, or L1R, while the VACV EV antigens comprise: A33R, A56R, or B5R. Preferably, each of the DNA plasmids comprise consensus DNA sequences that encode said antigens. The consensus DNA sequences that encode VACV MV antigens comprise: SEQ ID NO: 3 (A27L), SEQ ID NO: 11 (F9L), SEQ ID NO: 13

(H3L), or SEQ ID NO: 15 (L1R). The consensus DNA sequences that encode VACV EV antigens comprise: SEQ ID NO: 5 (B5R), SEQ ID NO: 7 (A33R), or SEQ ID NO: 9 (A56R). The consensus DNA sequences that encode A4L comprise: SEQ ID NO: 1. In some embodiments, the DNA plasmid capable of expressing a plurality of VACV MV antigens comprises encoding sequences that encode a protein having a sequence comprising: SEQ ID NO: 4 (A27L), SEQ ID NO: 12 (F9L), SEQ ID NO: 14 (H3L), or SEQ ID NO: 16 (L1R), the DNA plasmid capable of expressing a plurality of VACV MV antigens comprises encoding sequences that encode a protein having a sequence comprising: SEQ ID NO: 6 (B5R), SEQ ID NO: 8 (A33R), or SEQ ID NO: 10 (A56R), and DNA plasmid capable of expressing A4L antigen comprises encoding sequences that encode a protein having sequence of SEQ ID NO: 2. Preferably, the DNA vaccine comprises a plurality of distinct DNA plasmids that comprise encoding DNA sequences: SEQ ID NO: 1 (A4L), SEQ ID NO: 3 (A27L), SEQ ID NO: 5 (B5R), SEQ ID NO: 7 (A33R), SEQ ID NO: 9 (A56R). SEQ ID NO: 11 (F9L), SEQ ID NO: 13 (H3L), and SEQ ID NO: 15 (L1R), respectively. In another preferred embodiment, the DNA vaccine comprises a plurality of distinct DNA plasmids that comprise encoding DNA sequences that encode a protein having sequences: SEQ ID NO: 2 (A4L), SEQ ID NO: 4 (A27L), SEQ ID NO: 6 (B5R), SEQ ID NO: 8 (A33R), SEQ ID NO: 10 (A56R). SEQ ID NO: 12 (F9L), SEQ ID NO: 14 (H3L), and SEQ ID NO: 16 (L1R), respectively. In some preferred embodiments, the consensus encoding sequences are human codon-optimized.

In another preferred embodiment, the DNA vaccine comprises DNA plasmids pGX4001, pGX4002, pGX4003, pGX4004, pGX4005, pGX4006, pGX4007, or pGX4008, or a combination thereof.

Another aspect of the present invention relates to methods of inducing a protective immune response in a mammal to pox virus, including a neutralizing antibody response, comprising: injecting into tissue of said mammal a DNA vaccine comprising at least one DNA plasmid capable of expressing a plurality of VACV MV antigens, at least one DNA plasmid capable of expressing a plurality of VACV EV antigens, and a DNA plasmid capable of expressing A4L. Preferably, the pox virus is smallpox virus. In preferred embodiments, the injecting step comprises injecting intradermally or injecting intramuscularly. The method of inducing a protective immune response can further comprise the step of electroporating said tissue with an electroporating amount of electrical energy. Preferably, the electroporating step comprises delivering a constant current to said tissue. More preferably, the electroporating step comprises delivering 0.2 A of current. In some embodiments, the methods of inducing a protective immune response comprises repeating said injecting step. In a preferred embodiment, the delivering step comprises delivering eight distinct DNA plasmids.

The DNA vaccine described herein is formulated using DNA plasmid formulations that have a high DNA concentration. The high DNA concentration can be a concentration of 5 mg/mL or more, 6 mg/mL or more, 7 mg/mL or more, 8 mg/mL or more, 9 mg/mL or more, 10 mg/mL or more, 11 mg/mL or more, 12 mg/mL or more, 13 mg/mL or more, 14 mg/mL or more, 15 mg/mL or more. In some embodiments, the plasmid DNA may be in a concentration of 5-15 mg/mL, 5-14 mg/mL, 5-13 mg/mL, 5-12 mg/mL, 5-11 mg/mL, 5-10 mg/mL, 5-9 mg/mL, 5-8 mg/mL, a concentration of 6-15 mg/mL, 6-14 mg/mL, 6-13 mg/mL, 6-12 mg/mL, 6-11 mg/mL, 6-10 mg/mL, 6-9 mg/mL, 6-8 mg/mL, a concentration of 7-15 mg/mL, 7-14 mg/mL, 7-13 mg/mL, 7-12 mg/mL, 7-11 mg/mL, 7-10 mg/mL, 7-9 mg/mL, 8-15 mg/mL, 8-14 mg/mL, 8-13 mg/mL, 8-12 mg/mL, 8-11 mg/mL, 8-10 mg/mL, 9-15 mg/mL, 9-14 mg/mL, 9-13 mg/mL, 9-12 mg/mL, 9-11 mg/mL, 10-15 mg/mL, 10-14 mg/mL, 10-13 mg/mL, 10-12 mg/mL, 11-15 mg/mL, 11-14 mg/mL, 11-13 mg/mL, 12-15 mg/mL, 12-14 mg/mL, or 13-15 mg/mL. Using the high DNA plasmid concentration formulations to formulate the DNA vaccine, a mixture of various distinct DNA plasmids can be admixed together while maintaining high doses of each DNA plasmid. In some embodiments each distinct DNA plasmid is present at a high dose, which is a dose: greater than 50 µg, greater than 60 µg, greater than 70 µg, greater than 80 µg, greater than 90 µg, greater than 100 µg, greater than 110 µg, greater than 120 µg, greater than 130 µg, greater than 140 µg, greater than 150 µg, greater than 160 µg, greater than 170 µg, greater than 180 µg, greater than 190 µg, greater than 200 µg, greater than 210 µg, greater than 220 µg, greater than 230 µg, greater than 240 µg, or greater than 250 µg. Preferably, the high dose is greater than 120 µg, and more preferably 125 µg. In one preferred embodiment, DNA vaccines include DNA plasmids that are present at a dose of 125 µg.

In some embodiments of the present invention, the DNA vaccines can further include an adjuvant. In some embodiments, the adjuvant is selected from the group consisting of: alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86 including IL-15 having the signal sequence deleted and optionally including the signal peptide from IgE. Other genes which may be useful adjuvants include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. In some preferred embodiments, the adjuvant is selected from IL-8, IL-12, IL-15, IL-18, IL-28, MCP-1, MIP-1α, MIP-1p, RANTES, RANK, RANK LIGAND, Ox40, Ox40 LIGAND, CTACK, TECK, or MEC, or a combination thereof, and more preferably, the adjuvant is IL-12, IL-15, IL-28, or RANTES.

Poxviruses are a large complex viruses from the family Poxiridae and include VACV and variola virus (smallpox). Four genera of poxviruses are known to infect humans, and include orthopox, parapox, yatapox, molluscipox. Orthopox: variola virus, vaccinia virus, cowpox virus, monkeypox virus, smallpox (eradicated); Parapox: orf virus, pseudocowpox, bovine papular stomatitis virus; Yatapox: tanapox virus, yaba monkey tumor virus; Molluscipox: molluscum contagiosum virus (MCV). Other poxviruses, include Orthopoxvirus, such as camelpox virus, cowpox virus, ectromelia virus, monkeypox virus, raccoon poxvirus, skunk poxvirus, Tatera poxvirus, Uasin Gishu virus, variola virus, Volepox virus, Parapoxvirus such as Ausdyk virus, Bovin papular stomatitis virus, orf virus, pseudocowpox virus, red deer poxvirus, seal parapoxvirus, Capripoxvirus such as sheep-pox virus, goat-pox Vlrus lumpyskin disease virus, Suipoxvirus such as swinepox virus, Leporipoxvirus such as myxoma virus fibroma virus, hare fibroma virus, squirrel fibroma virus, western squirrel fibroma, Avipoxvirus of many species, Yatapoxvirus such as Tantpox virus, Yabapoxvirus, Molluscipoxvirus such as molluscum contagiosum virus, macropod poxvirus, crocodilian poxvirus, among others. In addition to the high crossreactivity (broad protection) of the DNA vaccines described herein to smallpox, due to the high identity between poxviruses, it is expected that the DNA vaccines of the present invention would provide cross protection between different poxviruses as well.

Routes of administration include, but are not limited to, intramuscular, intranasally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, traditional syringes, needleless injection devices, "microprojectile bombardment gone guns", or other physical methods such as electroporation ("EP"), "hydrodynamic method", or ultrasound.

Examples of electroporation devices and electroporation methods preferred for facilitating delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

The following is an example of a preferred embodiment of the present invention, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The present invention is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 μs, 20 μs, 10 μs or 1 μs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

A pharmaceutically acceptable excipient can include such functional molecules as vehicles, adjuvants, carriers or diluents, which are known and readily available to the public. Preferably, the pharmaceutically acceptable excipient is an adjuvant or transfection facilitating agent. In some embodiments, the nucleic acid molecule, or DNA plasmid, is delivered to the cells in conjunction with administration of a polynucleotide function enhancer or a genetic vaccine facilitator agent (or transfection facilitating agent). Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021,579 filed Apr. 1, 1994, which is incorporated herein by reference. The transfection facilitating agent can be administered in conjunction with nucleic acid molecules as a mixture with the nucleic acid molecule or administered separately simultaneously, before or after administration of nucleic acid molecules. Examples of transfection facilitating agents includes surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

In some preferred embodiments, the DNA plasmids are delivered with an adjuvant that are genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, pl50.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The DNA plasmid vaccines according to the present invention comprise DNA quantities of from about 1 microgram to about 10 milligrams, about 10 microgram to about 10 milligrams, about 100 microgram to about 10 milligrams, about 200 microgram to about 10 milligrams, about 300 microgram to about 10 milligrams, about 400 microgram to about 10 milligrams, about 500 microgram to about 10 milligrams, about 1 microgram to about 1 milligrams, about 10 microgram to about 1 milligrams, about 100 microgram to about 1 milligrams, about 200 microgram to about 1 milligrams, about 300 microgram to about 1 milligrams, about 400 microgram to about 1 milligrams, about 500 microgram to about 1 milligrams, about 100 microgram to about 1 milligrams, about 200 microgram to about 1 milligrams, about 300 microgram to about 1 milligrams, about 400 microgram to about 1 milligrams, or about 500 microgram to about 1 milligrams. Preferably, the quantity of DNA present in the vaccine is from about 100 microgram to about 1 milligrams.

The DNA plasmid vaccines according to the present invention are formulated according to the mode of administration to be used. In cases where DNA plasmid vaccines are injectable compositions, they are sterile, and/or pyrogen free and/or particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. In some embodiments, a stabilizing agent that allows the formulation to be stable at room or ambient temperature for extended periods of time, such as LGS or other polycations or polyanions is added to the formulation.

In some embodiments, methods of eliciting an immune response in mammals against a consensus smallpox antigen include methods of inducing mucosal immune responses. Such methods include administering to the mammal one or more of CTACK protein, TECK protein, MEC protein and functional fragments thereof or expressible coding sequences thereof in combination with an DNA plasmid including a consensus smallpox antigen, described above. The one or more of CTACK protein, TECK protein, MEC protein and functional fragments thereof may be administered prior to, simultaneously with or after administration of the DNA plasmid smallpox vaccines provided herein. In some embodiments, an isolated nucleic acid molecule that encodes one or more proteins of selected from the group consisting of: CTACK, TECK, MEC and functional fragments thereof is administered to the mammal.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Preferably the DNA formulations for use with a muscle or skin EP device described herein have high DNA concentrations, preferably concentrations that include microgram to tens of milligram quantities, and preferably milligram quantities, of DNA in small volumes that are optimal for delivery to the skin, preferably small injection volume, preferably 25-200 microliters (μL). In some embodiments, the DNA formulations have high DNA concentrations, such as 1 mg/mL or greater (mg DNA/volume of formulation). More preferably, the DNA formulation has a DNA concentration that provides for gram quantities of DNA in 200 μL of formula, and more preferably gram quantities of DNA in 100 μL of formula.

The DNA plasmids for use with the EP devices of the present invention can be formulated or manufactured using a combination of known devices and techniques, but preferably they are manufactured using an optimized plasmid manufacturing technique that is described in a commonly owned, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a commonly owned U.S. Pat. No. 7,238,522, which issued on Jul. 3, 2007. The high concentrations of plasmids used with the skin EP devices and delivery techniques described herein allow for administration of plasmids into the ID/SC space in a reasonably low volume and aids in enhancing expression and immunization effects. The commonly owned application and U.S. Ser. No. 60/939,792 and U.S. Pat. No. 7,238,522, respectively, are hereby incorporated in their entirety.

Methods

The following methods are utilized for the examples below, where applicable and where a specific method is not provided otherwise in the particular example.

Cloning of the DNA expression constructs. The VACV genes, A4L, A27L, A33R, A56R, B5R, F9L, H3L, and L1R (from the Western Reserve Strain), were chemically synthesized from synthetic oligonucleotides, human codon-optimized, and modified to contain a Kozak consensus sequence and IgE leader sequence at the 5' end and HA epitope tag at the 3' end of the DNA sequence. Each of these modified gene cassettes were cloned using conventional cloning methods into the eukaryotic expression plasmid, pVAX1 (Invitrogen, Carlsbad, Calif.) by GENEART (Burlingame, Calif.). Expression of each gene is regulated by the CMV promoter. The synthetic gene cassettes of A4L and B5R were cloned into the HindIII and XhoI sites to make the expression plasmids pGX4001 and pGX4003, respectively. To make expression plasmids of A33R (pGX4004) and A56R (pGX4005), the synthetic gene cassettes were cloned into the HindIII and XbaI restriction sites. pGX4007 and pGX4008 were prepared by cloning the synthetic gene cassettes of H3L and L1R into the HindIII and BamHI restriction sites. The remaining expression plasmids, pGX4002 and pGX4006 were made by cloning the synthetic gene cassettes of A27L and F9L into the KpnI/XhoI and EcoRI/XbaI restriction sites, respectively. After cloning, all antigens were confirmed by sequencing.

Vaccine preparation and immunization. Plasmids were manufactured to high concentrations and purified using the manufacturing procedure described by Hebel et al. in U.S. Pat. No. 7,238,522 with modifications. This method yields endotoxin-free plasmid formulations ($\leq 10$ EU/mg) at very high plasmid concentrations, adapted for biopharmaceutical delivery of vaccines. All plasmid preparations were formulated and prepared with 1% weight/weight with high-performance liquid chromatography (HPLC) purified low molecular weight poly-L-glutamate (LGS, average MW 10,900) in sterile water. All plasmids (pGX4001 to pGX4008) were combined to make a single vaccine preparation consisting of 125 μg of each plasmid in a total volume of 0.1 mL for the ID or 0.5 mL for the IM administration.

Animals were anesthetized intramuscularly with ketamine HCL (10 to 30 mg/kg). The vaccine was administered to each thigh (one injection site per thigh per vaccination) and delivered either ID or IM in the semimembranous muscle in combination with EP using CELLECTRA® 2000 device (device validated for human use; VGX Pharmaceuticals, Blue Bell, Pa.). Immediately following the injection, 2×2 at 0.2 A constant-current, 52 ms pulse length with 1 s between pulses were applied for ID administration, and 3 pulses at 0.5 A constant-current with 52 ms pulse length with 1 s between pulses was applied for IM administration. Immunizations were performed at days 0, 28, and 56 with serum collected on the days of immunization to measure antibody responses.

Sample collection and PBMC isolation. Cynomolgus macaques were bled every two weeks during the vaccination schedule and every three post-challenge. Animals were anesthetized intramuscularly with ketamine HCL (10 to 30 mg/kg). Blood was collected in EDTA tubes. PBMC's were isolated from whole blood by standard Ficoll-Hypaque density gradient centrifugation, resuspended in complete culture medium (RPMI 1640 with 2 mM L-glutamine supplemented with 10% heat-inactivated FBS, 100 IU/ml penicillin, 100 μg/ml streptomycin, and 55 μM β-mercaptoethanol).

Preparation of the Antigens for Antigen-Specific ELISA. The Open Reading Frames of each antigen were PCR amplified from the Western Reserve strain of VACV using gene-specific primers containing appropriate restriction enzyme sites and cloned into the prokaryotic expression vector, pEt219a(+) (EMD Chemicals, Gibbstown, N.J.). The 3'-end oligonucleotide was designed to allow fusion with the 6× Histidine tag present in pEt21a(+). Proteins were purified using standard nickel column purification methods (Abgent, Inc., San Diego, Calif.).

Antigen-specific ELISA. To determine the IgG antibody responses, ELISAs were performed by coating a MaxiSorp Immuno 96 well plate (Nunc, Rochester, N.Y.) with 50 ng of purified antigen (A4L, A27L, A33R, A56R, B5R, F9L, H3L, or L1R) diluted in PBS. After overnight incubation at 4° C., plates were washed with PBS supplemented with 0.05% Tween 20 (PBS-T) and then blocked for 1 h at RT with PBS supplemented with 3% BSA. Serum collected from individual Cynomolgus macaques were diluted in PBS supplemented with 0.5% BSA; 0.05% Tween 20, and incubated overnight at 4° C. with 50 μl of the diluted serum. The wells were washed with PBS-T and then incubated with the secondary antibody, goat anti-rabbit IgG-HRP conjugated (Sigma-Aldrich, St. Louis, Mo.) and diluted 1 in 10,000 in PBS supplemented with 0.5% BSA; 0.05% Tween 20 (100 μL/well). The wells were incubated for 1 h at room temperature and washed. TMB substrate and stop solution was added to each well according to manufacturer's recommendations (KPL, Gaithersburg, Md.).

Absorbance was measured at 450 nm using the Lumistar Galaxy plate reader (BMG Labtech). Endpoint titers are expressed as the reciprocal of the highest serum dilution yielding a positive reactivity greater than two-fold above negative control serum.

VACV ELISA. Microtiter plates were coated with paraformaldehyde-fixed sucrose-gradient purified VACV WR strain (Advanced Biotechnologies, Inc.) at a concentration of 0.6 μg/ml and incubated overnight at 4° C. Plates were blocked for 2 h at 37° C. using PBS-T supplemented with 5% non-fat dry milk (PBS-TM). Wells were washed 8 times with PBS-T and incubated with serial dilutions of monkey serum for 1 h at 37° C. After washing, the wells were incubated with secondary antibody, with goat anti-monkey IgG conjugated to horseradish peroxidase (KPL), and ABTS substrate (Sigma-Aldrich). The reaction was stopped with the addition of 100 μL of 10% SDS and read at 405 nm using a Molecular Devices SpectraMax Plus 384.

Endpoint titers are expressed as the reciprocal of the highest serum dilution yielding a positive reactivity≥mean O.D. plus 3 S.D. of the negative control serum.

Synthetic peptides. The peptides used for this study were derived from the coding region of A4L, A27L, A33R, A56R, B5R, F9L, H3L, and L1R of WR strain of VACV. Total antigen peptide libraries were synthesized for A4L, A27L, A33R, A56R, F9L, H3L, and L1R. All peptides were 15-mers overlapping by either 9 amino acids (in the case of A27L), 11 amino acids (in the case of A4L, A33R, A56R, F9L, H3L, and L1R), or 6 amino acids (in the case of B5R). The A27L library was prepared by Invitrogen. All other libraries were prepared by GenScript Corporation (Piscataway, N.J.). Libraries were prepared as the corresponding peptide pool at a concentration of 10 mg/mL in DMSO.

IFN-γ ELISPOT assay. The nonhuman primate ELISpot assays were performed (See Boyer, J. D. et al. *J. Med. Primatol.* 34, 262-270 (2005). Antigen-specific responses were determined by subtracting the number of spots in the negative control wells from the wells containing peptides. Results are shown as the mean value (spots/million splenocytes) obtained for triplicate wells.

Carboxyfluorescein succinimidyl ester (CFSE) conjugation and flow cytometry analysis of PBMCs. Cells were pelleted and resuspended in 1 ml carboxyfluorescein diacetate succinimidyl ester (CFDA-SE) (Molecular Probes, Eugene, Oreg.) in PBS (1:2000 dilution). Cells were incubated at 37° C. for 10 min. Cells were washed with complete media and resuspended to a concentration of $1 \times 10^6$ cells/100 µl and plated in 96 well round bottom plates with 100 µl of total peptide pools. Five µg/ml Concavalin A (positive) and complete media (negative) were used as controls. Cultures were incubated for 5 days. Cells were first stained with Vivid dye violet, a live/dead cell marker, for 10 min at 37° C. Cells were washed once with PBS. Cells were then stained using anti-human CD3-APC Cy7 (clone SP34-2) (BD Pharmingen) and anti-human CD4-PerCP Cy5.5 (clone L200), anti-human CD8-APC (clone SKI) for 1 hour at 4° C. Cells were then washed twice with PBS and fixed with 1% paraformaldehyde. Data was collected using a LSRII flow cytometer (BD Biosciences, Franklin Lakes, N.J.). Flow cytometry data was analyzed using FlowJo software (Tree Star, Ashland, Oreg.), gating on $CD3^+$ lymphocytes. Thirty to fifty thousand $CD3^+$ lymphocytes were collected per sample. Data is shown after media subtraction. Proliferative responses to A4 were not assessed due to high background proliferation in pre-immune samples.

Intracellular Cytokine Staining. Antibody Reagents: Directly conjugated antibodies were obtained from the following: BD Biosciences (San Jose, Calif.): IL-2 (PE), CD3 (APC Cy7), CD8 (APC), IFN-γ (Alexa Fluor 700), and TNF-α (PE Cy7), CD95 (PE Cy5) and CD4 (PerCP Cy5.5). CD28 (ECD) was obtained from Beckman Coulter.

Cell stimulation and staining. PBMCs were resuspended to $1 \times 10^6$ cells/100 µl in complete RPMI and plated in 96 well plates with A27L and B5R stimulating peptides 100 µl of 1:200 dilutions. An unstimulated and positive control (Staphylococcus enterotoxin B, 1 µg/ml; Sigma-Aldrich) was included in each assay. Cells were incubated for 5 hours at 37° C. Following incubation, the cells were washed (PBS) and stained with surface antibodies. The cells were washed and fixed using the Cytofix/Cytoperm kit (BD Pharmingen, San Diego, Calif.) according to instructions. Following fixation, the cells were washed twice in the perm buffer and stained with antibodies against intracellular markers. Following staining, the cells were washed, fixed (PBS containing 1% paraformaldehyde), and stored at 4° C. until analysis.

Flow cytometry. Cells were analyzed on a modified LSR II flow cytometer (BD Immunocytometry Systems, San Jose, Calif.). Fifty thousand $CD3^+$ events were collected per sample. Data analysis was performed using FlowJo version 8.6.3 (TreeStar, San Carlos, Calif.). Initial gating used a forward scatter area (FSC-A) versus height (FSC-H) plot to remove doublets. The events were subjected to a lymphocyte gate by a FSC-A versus SSC plot. Live T cells were identified by a live/dead versus $CD3^+$ plot. Following this, events are sequentially gated on $CD8^+$ and $CD4^-$ events versus IFN-γ to account for down-regulation. Following identification of $CD8^+$ T cells, a gate was made for each respective function using combinations that provided optimal separation. After the gates for each function were created, we used the Boolean gate platform to create the full array of possible combinations, equating to 15 response patterns when testing 4 functions. Data are reported after background correction. Responses for one pVAX1 animal (#4384) were not included in the analysis due to high pre-immune responses.

Virus propagation and preparation. The Zaire strain, V79-I-005 (monkeypox virus Master Seed NR-523), of monkeypox virus was obtained from the National Institutes of Health Biodefense and Emerging Infections Research Resources Repository. This Zaire strain was originally obtained from a fatally infected human from Zaire in 1979 (isolated by World Health Organization Collaborating Center for Smallpox and Other Poxvirus Infections at the US Center for Disease Control and Prevention). The inoculum was prepared by passaging the virus in chicken embryo fibroblasts, and purified by sedimentation through a standard sucrose gradient. It was propagated in chicken embryo fibroblasts and purified.

Monkeypox virus challenge. Four weeks after the last vaccination (day 91), Cynomolgus macaques were anesthetized as described herein and intravenously infused with $2\times10^7$ PFU of monkeypox virus NR-523 into the saphenous vein using a 23 gauge butterfly. In order to confirm the actual delivered dose, the challenge inoculum was back-tittered on Vero E6 cells using standard plaque assay technique.

Real-time PCR to detect monkeypox virus genomes. DNA was extracted from frozen blood samples using QIAamp DNA mini kit (Qiagen). The real-time PCR was prepared according to manufacturer's instructions for Quantitative Pan-orthopox HA PCR assay (Applied Biosystems) and consisted of the following primers for amplification hemagglutinin gene: OPHA F89: 5'-ATGTACTATCTCAACGTAG-TAG-3' (SEQ ID NO.: 17) and OPHA R219: 5'-CTGCAGAACATAAAACTATTAATATG-3' (SEQ ID NO.:18). The TaqMan probe (OPHA P143S-MGB: 6FAM AGTGCTTGGTATAAGGAG MGBNFQ (SEQ ID NO.:19 and SEQ ID.: 20)) was FAM-labeled at the 5'-end and contained a nonfluorescent quencher. Viral genome copies were performed with a LightCycler 1.5 (Roche).

Measurement of VACV-neutralizing antibody. Serum from monkeys were collected throughout the duration of the study, heat-inactivated (56° C. for 30 min), and evaluated for the presence of VACV-neutralizing antibodies using classical plaque reduction neutralization tests. Each assay included as a positive control FDA standard reference Vaccinia Ig (Cangene) and validated at the Center for Biologics Evaluation and Research at the FDA. Negative controls included serum from unvaccinated macaques. One to four serial dilutions of the serum were prepared in complete culture medium and added to 24 well plates of Vero E6 cells (100% confluent) in triplicate. $4.5\times10^5$ PFU of Zaire 79 strain was added to each well of a 24-well plate. A 500 μL semisolid overlay of pre-warmed methylcellulose (comprised of equal volume of 4% MEM (supplemented 4% FBS, 4 mM L-glutamine and 1% methylcellulose) was added to each well. Plates were incubated at 37° C.; 5% $CO_2$ for 72 h. Cell monolayers were stained with 250 μL of 0.1% crystal violet staining solution (prepared in 20% methanol).

Plaques were counted and percent neutralization was calculated relative to the number of plaques in the absence of antibody. Titers represent the reciprocal of the highest dilution resulting in 50% reduction in the number of plaques.

Complete blood count analysis Complete cell blood counts (CBC) were determined using a HevaVet 950 FS Hematology Analyzer (Drew Scientific). CBC was performed at each time point bleed during vaccination and on days 0, 6, 12, 21, and 27 of the challenge. Hematology parameters included: hematocrit, hemoglobin, total leukocyte count, and differential leukocyte counts (neutrophils, lymphocytes, monocytes, eosinophils, and basophils), platelet count, mean corpuscular volume, mean corpuscular hemoglobin, mean corpuscular and hemoglobin concentration.

Statistical analysis Student's paired t-test was used for comparison where mentioned. Data are represented as the mean±s.e.m and P<0.05 (two-tailed T-Test) was considered statistically significant. The Spearman Rank correlation (nonparametric) test was used to evaluate the correlation between neutralizing antibody titers (measured by PRNT assay) and lesion counts.

Example 1

Cloning, In Vitro Expression and Manufacturing of Plasmids Expressing Smallpox Antigens Each gene was synthetically-constructed and prepared by GeneArt Inc. (Toronto, ON) from oligonucleotides. The oligonucleotides were codon-optimized from the Vaccinia Virus Western Reserve (WR) strain and cloned into pVAX1 (Invitrogen, Carlsbad, Calif.) using standard cloning methods. The DNA vaccine plasmids, pGX4001 and pGX4003, encoding the optimized genes for A4L and B5R, respectively, were prepared by cloning the synthetically-constructed fragment into the HindIII and XhoI restriction sites. pGX4004 (encoding A33R) and pGX4005 (encoding A56R) were prepared by cloning the DNA fragment into the Hind III and XbaI restriction sites. pGX4007 and pGX4008 were prepared by cloning the DNA fragment encoding H3L and L1R, respectively, into the Hind III and BamHI restriction sites. For the plasmid encoding F9L (pGX4006) and A27L (pGX4002), the DNA fragment was cloned into the EcoRI/XbaI, and KpnI/XhoI restriction sites, respectively. To allow for more efficient protein expression, a Kozak consensus sequence and an IgE leader sequence was added to the 5'-end of each gene. In addition, to aid in localization and expression analysis, a HA-epitope tag was added to the 3'-end of the gene.

Following cloning, all antigens were confirmed by sequencing, and the inserts were tested for expression. Then, the plasmids were produced using partially the manufacturing procedure described by Hebel et al. in U.S. Pat. No. 7,238,522 with modifications, which yielded plasmid formulations at very high plasmid concentrations, adapted for biopharmaceutical delivery of vaccines (for example purposes see FIG. 1). Using the method, a smallpox multivalent DNA vaccine composed of the VACV antigens A4L, A27, A33R, A56R, B5R, F9L, H3L, and L1R was produced. The products demonstrated high purity with undetectable RNA, protein and endotoxin, average concentration of 10.7±0.7 mg/mL and supercoiled percentage of 94.5±1.1% after storage at −80° C. for over 1 year (data not shown). Each antigen in the vaccine preparation elicited both a robust antibody and cellular immune response in mice or rabbits (data not shown).

Some of the smallpox antigens encoding plasmids are also shown (FIGS. 2-9).

TABLE 1

Summary of cloned vaccine antigens

| Antigen | Size (kDa) | Biological Properties | Infectious form association |
|---|---|---|---|
| A4L | 39 | Viral core protein synthesized late post-infection and involved in viral core assembly. | IMV |
| A27L | 14.0 | Required for formation and assembly. | IMV |
| A13L | 14 | Required for virion maturation. | IMV |
| A14L | 9.9 | Required for morphogenesis. | IMV |
| D8L | 35.3 | Envelope protein, binds chondroitin. | IMV |
| F9L | 23.8 | Membrane glycoprotein structurally related to L1R and involved in cell fusion/entry | IMV |
| H3L | 37.5 | C-terminal transmembrane protein, morphogenesis, neutralizing antibodies. | IMV |
| L1R | 27.3 | Type I membrane protein, myristoylated, target of neutralizing antibodies. | IMV |
| A33R | 20.5 | Type II membrane protein, actin tail formation. | EEV |
| A56R | 69-85 | Encodes the Hemagglutinin gene and involved in cell fusion | EEV |
| B5R | 35.1 | Type I membrane, viral egress, target of neutralizing antibodies. | EEV |

In all experiments described herein, endotoxin-free plasmid preparations was diluted in sterile water and formulated at 1% weight/weight with high-performance liquid chromatography (HPLC) purified low molecular weight poly-L-glutamate (LGS, average MW 10,900), as previously described in Draghia-Akli R, Khan A S, Pope M A, Brown P A. *Innovative electroporation for therapeutic and vaccination applications. Gene Therapy & Molecular Biology;* 9:329-38 (2005).

For these plasmid-based therapies to be effectively transferred to humans, it is preferred to have larger quantities of plasmid in a small formulation volume (volumes that are similar to that of classic vaccines). Furthermore, the transgene product should be secreted efficiently from the target organ, and be detectable and active.

Example 2

Plasmid Administration and Electroporation

A constant current electroporation device for ID application (CELLECTRA®, VGX Pharmaceuticals, Inc., Blue Bell, Pa.) was developed with micro-electrodes (mEP) mounted on a sterilizable, disposable plastic array, which is the only component that actually touches the skin of the patient (to prevent cross-contamination). The concentrated, high purity vaccine formulation in a small volume (volumes similar to that of classic vaccines, i.e., between 50 and 300 µL, and more preferably between 50-100 µL or 100-200 µL) is delivered to the selected area, the target area, and then the target area is surrounded by the micro-array. The micro-electrodes are inserted into the skin. The plastic array creates a uniform pressure around the micro-electrodes inserted into the skin, which helps to generate a uniform electric field during the EP process in the target area.

Example 3

Immunization of Rabbits with Smallpox-expressing Constructs

In a pilot experiment, immune responses to smallpox antigens delivered by the plasmid vaccines of Example 1, above, and in vivo constant current electroporation were analyzed in groups of rabbits (n=3/group) (see timeline, FIG. 10). Rabbits were fed food and water ad libitu and housed according to IUCUC standards and practices at Stillmeadow, Inc. (Sugarland, Tex.). Prior to the DNA vaccine administration, the injection site was shaved and thoroughly cleaned to remove excess hair and debris. On the day of DNA vaccination, rabbits were weighed, anaesthetized with ketamine/xylazine, and bled, and maintained on isoflourane (2%) for the duration of the treatment.

The plasmids were administered via a single intramuscular (IM) injection of 800 μg (100 μg each antigen and/or empty vector up to 800 μg per injection) in the following combinations: Group 1 rabbits were immunized with a combination of eight plasmids expressing varying smallpox antigens (A13L, A14L, A27L, A33R, B5R, D8L, H3L, L1R); group 2 rabbits were immunized with a combination of four different antigens (A27L, B5R, D8L, L1R); group 3 received an immunization with an individual plasmid expressing a single antigen (B5R). All plasmids were administered into semimembranosus muscle followed by electroporation using the CELLECTRA® device (VGX Pharmaceuticals, Inc., Blue Bell, Pa.), at 0.6 Amps, 3 pulses, 52 ms/pulse, 1 sec between pulses. Sera were collected from rabbits at different time points and used to determine antibody responses by protein ELISA.

Antibody responses were improved by electroporation in both immunized groups irrespective of the number of antigens delivered. Humoral responses to various antigens were also measured by ELISpot: B5R (FIG. 11), H3L (FIG. 12), A27L (FIG. 13), L1R (FIG. 14). Sera from animals in each group (n=3) were pooled and diluted 1:50. Sera from groups 1 and 2 demonstrated significant response to A27L and L1R (*$p<0.05$ compared to Group 3), and the immune response to a single vaccine was not affected when these antigens were administered in groups of either 4 or 8 antigens.

Example 4

Immunization of Non-human Primates with Smallpox-expressing Constructs

An initial pilot study was conducted in a small number of cynomolgus macaques (6 animals) to examine whether DNA injection followed by electroporation (EP) elicits a significantly superior immune response. The experiments were performed using the CELLECTRA® device. Groups of 2 macaques (n=2/group) were injected intramuscularly (IM) with ascending doses of a plasmid encoding a viral antigens: optimized A4L (or A4Lopt), A27Lopt, and B5Ropt (see plasmids in Example 1, above).

Animals were injected at d0, 28 and 56 with 0.03, 0.1 and 0.3 mg of each plasmid, respectively (in 0.5 mL sterile water+0.01 mg/mL LGS) in the semimembranosus muscle through intact skin, and then electroporated under conditions of 0.6 Amps, 52 msec pulse length and 1 sec between pulses. At d84, all animals received a protein boost. cytotoxic T-lymphocytes (CTL) responses were measured at baseline, and at d28, 56, 84 and 112 (FIG. 16). As shown in FIG. 16, ELISpot results 2 weeks after the first immunization showed that the group that received the IM injection and electroporation had, on average, 2.5× as many interferon-gamma (IFNγ) producing cells than the groups receiving the IM injection alone.

Example 5

A combination vaccine consisting of several different Vaccinia Virus antigens was evaluated to determine the efficacy of the combination vaccine as measured by the level of antibody responses generated in the animals. In addition, the DNA delivery method, comparing the delivery either intradermally (ID) or intramuscularly (IM), was evaluated for efficacy. The DNA was delivered using the CELLECTRA® constant current device.

Animals: New Zealand White rabbits (n=3 to 4 per group) were evaluated for the antibody immune response using ELISA. Rabbits were fed food and water ad libitu and housed according to IUCUC standards and practices at Stillmeadow, Inc. (Sugarland, Tex.). Prior to the DNA vaccine administration, the injection site was shaved and thoroughly cleaned to remove excess hair and debris.

On the day of DNA vaccination, rabbits were weighed, anaesthetized with ketamine/xylazine, and bled, and maintained on isoflourane (2%) for the duration of the treatment. The DNA vaccines, which included plasmids encoding various vaccinia virus antigens, were administered (Day 0, 21, and 35) either intradermally (ID) (100 μl) or intramuscularly (IM) (500 μl or 1000 μl), and each vaccine consisted of a total of 1 mg of total plasmid per rabbit (250 μg per antigen). The plasmid combination utilized in the vaccine formulations consisted of: influenza H5 hemagglutinin-expressing plasmid (H5HA) (used as positive control for the assay), and a combination of three vaccinia virus antigens (A4L, A27L, and B5R; see Example 1, above). Each DNA vaccine formulation was prepared in 1% LGS.

All DNA vaccines were administered into semimembranosus muscle followed by electroporation using the CELLECTRA® constant current device using a variety of electroporation conditions as shown in FIG. 18. Groups A to D were subjected to an ID injection of 100 μl and electroporated at 0.2 Amps and either received 2 pulses (Group A), 3 pulses (Group B), 4 pulses (Group C), 6 pulses (Group D). Group E received an ID injection, but did not receive an electroporation. Group F, G and I were intramuscularly (IM) administered with 500 μl formulation of the DNA vaccine and were electroporated at 0.5 Amps and received 3 pulses, with each consisting of either an 80, 4, 4, and 10-15 sec lag period, respectively. Group J received no electroporation (1M, 500 μl). Group H received 1000 μl of an intramuscular injection and electroporation conditions consisting of 0.5 Amps, 4 sec lag, and 3 pulses. The CELLECTRA® constant current device was programmed to deliver 52 ms/pulse and 1 sec between pulses. Sera was collected from rabbits at different time points and used to determine antibody responses by ELISA (See results in FIGS. 19-21).

Example 6

New Zealand White rabbits of 8 to 9 weeks of age (n=4 per group) were evaluated for antibody immune response using ELISA. Rabbits were fed food and water ad libitum and housed according to IUCUC standards and practices at Stillmeadow, Inc. (Sugarland, Tex.). Prior to the DNA vaccine administration, the injection site was shaved and thoroughly cleaned to remove excess hair and debris. On the day of DNA vaccination, rabbits were weighed, anaesthetized with ketamine/xylazine, and bled, and maintained on isoflourane (2%) for the duration of the treatment.

The plasmids encoding various Vaccinia virus antigens (see Example 1, above) were administered (Day 0, 21, 42, and 84) either intradermally (ID) or intramuscularly (IM), in volumes of 100 µl and 500 µl, respectively, and consisted 1 mg of total plasmid per rabbit (125 µg per antigen and/or empty vector up to 1 mg per injection). FIGS. 22 and 23 show the vaccination schedule and the vaccination parameters in detail. The following combinations were used and were followed by electroporation (Groups A to J): Group A and F rabbits were immunized with an individual plasmid expressing a single antigen (B5R) antigen; Group B and G rabbits were immunized with a combination of four different antigens (A27L, B5R, H3L, and L1R); Groups C and H consisted of a combination of 8 plasmids expressing various antigens (A4L, A27L, A33R, A56R, B5R, F9L, H3L, and L1R); Groups D and I served as a negative control for antibody response and were immunized with the empty vector, pVAX1 (Invitrogen, Carlsbad, Calif.); and Groups E and J were vaccinated with the same combination of 8 antigens, but without electroporation. Each antigen formulation was prepared in 1% LGS.

All plasmids were administered into semimembranosus muscle followed by electroporation using the CELLECTRA® constant current device (other than Group 5), at 0.5 Amps, 3 pulses, 52 ms/pulse, 1 sec between pulses for IM injections and 0.2 Amps, 4 pulses, 52 ms/pulse, 1 sec between pulses for ID injections. Sera were collected from rabbits at different time points and used to determine antibody responses by protein ELISA (FIGS. 24 to 33).

ELISA antigen preparation: The antigens for ELISA were prepared by Abgent, Inc. (San Diego, Calif.). The ORF encoding the gene was PCR amplified using gene-specific primers containing appropriate restriction sites for cloning. The 3'-end oligonucleotide was designed to allow fusion with the 6× Histidine tag present in the prokaryotic expression vector, pEt21a(+). Proteins were purified using standard nickel column purification methods.

ELISA assay: To determine the IgG responses, ELISA assays were performed by coating a MaxiSorp Immuno 96 well plate (Nunc, Rochester, N.Y.) with 50 ng of antigen (A4L, A27L, A33R, B5R, H3L, or L1R) diluted in PBS and incubated overnight at 4° C. Following washing with PBS supplemented with 0.05% Tween 20 (PBS-T), plates were blocked with PBS supplemented with 3% BSA and incubated for 1 h at room temperature. Rabbit sera was diluted in PBS supplemented with 0.5% BSA; 0.05% Tween 20, and incubated (50 µl) overnight at 4° C. Following washing with PBS-T, the wells were incubated with the secondary antibody, goat anti-rabbit IgG-HRP conjugated (Sigma-Aldrich, St. Louis, Mo.) and diluted 1 in 10,000 in PBS supplemented with 0.5% BSA; 0.05% Tween 20 (100 µl/well). The wells were incubated for 1 h at room temperature and washed accordingly. TMB substrate and stop solution was added to each well according to manufacturer's recommendations (KPL, Gaithersburg, Md.). Absorbance was measured at 450 nm using the Lumistar Galaxy plate reader (BMG Labtech, Durham, N.C.). ELISpot assay: MultiScreen—IP 96 well plates (Millipore, Bedford, Mass.) were coated with monoclonal antibody (mAb) to monkey IFN-γ (GZ-4) diluted 1 to 100 in PBS and incubated overnight at 4° C. After five washes with PBS, plates were blocked for 2 h at room temperature with complete culture medium (RPMI 1640 with 10% FBS, 1% Penicillin/Streptomycin). PBMCs were added in triplicates at an input cell number of 2×10$^5$ cells in 100 µl of complete culture medium. Peptides were diluted in complete culture medium at a final concentration of 25 µg/ml and 100 µl dilution was added per well. Concanavalin A (ConA, 5 µg/ml; Sigma-Aldrich, St. Louis, Mo.) was used as a positive control, and cells resuspended in complete culture medium only served as a negative control. After an incubation of 24 h at 37° C., plates were washed five times with PBS followed by overnight incubation at 4° C. along with 100 µl/well of biotinylated detector mAb to monkey INF-γ (7-B6-1) and diluted to 1,000 in PBS. Plates were washed and 100 µl/well of strepatavidin-alkaline phosphatase conjugate, diluted 1 to 1,000 in PBS were added and incubated at room temperature for 1 h. The wells were then washed and 100 µl of substrate solution (BCIP/NBT, Sigma-Aldrich) was added per well. The colorimetric reaction was terminated after 10 minutes at room temperature by washing several times with tap water. Plates were air-dried and the spots counted using an automated ELISpot reader system (CTL analyzers, Cleveland, Ohio) with the ImmunoSpot® Software. The mean number of spots from triplicate wells was adjusted to 1×10$^6$ splenocytes. ELISpot data are expressed as mean±S.D.

The antigen specific IFN-γ responses were calculated after subtraction of spots formed in control medium wells from the number of spots formed in response to the corresponding peptides used for stimulation. ELISpot assays were also performed after depletion of CD8$^+$ lymphocytes from PBMCs by using CD8 depletion beads (Miltenyi Biotec, Gladbach, Germany).

Example 7

Optimization of Electroporation Conditions for Intradermic Vaccination of High Concentration Multivalent DNA Vaccine in Rabbits Optimization of EP conditions is an important factor for protein expression. Experiments to optimize EP conditions were carried out in rabbits using a high concentrated combination vaccine. Table 2 shows the EP conditions that were investigated.

TABLE 2

Optimization conditions for EP and titers for B5R, A27L and A4L in rabbits.

| Group | Nb | Lag | Amp | Pulse | HI titers | Endpoint titer B5R | Endpoint titer A27L | Endpoint titer A4L |
|---|---|---|---|---|---|---|---|---|
| A | 4 | 4 | 0.2 | 2 | 190 ± 75.5 | 1100 ± 714.1 | 500 ± 173.2 | 125 ± 43.3 |
| B | 4 | 4 | 0.2 | 3 | 120 ± 60.0 | 2600 ± 600.0 | 650 ± 150.0 | 1100 ± 714.1 |
| C | 4 | 4 | 0.2 | 2 × 2 | 640 ± 320.0 | 3200 ± 0.0 | 600 ± 173.2 | 1250 ± 665.2 |
| D | 4 | 4 | 0.2 | 3 × 2 | 105 ± 71.8 | 1662.5 ± 888.2 | 3200 ± 0.0 | 400 ± 173.2 |
| E | 3 | NA | NA | NA | 20 ± 0.0 | 200 ± 0.0 | 333 ± 240.4 | 466.3 ± 156.2 |

Animals were vaccinated with a positive control influenza H5 hemagglutinin expressing plasmid (HA) (Laddy, D. J. et al. Heterosubtypic protection against pathogenic human and avian influenza viruses via in vivo electroporation of synthetic consensus DNA antigens. PLoS. ONE. 3, e2517

(2008)) and a combination of B5R, A27L and A4L under different ID-EP parameters. The results indicated that a 2×2 intradermic EP pulse pattern provided the better response with the most robust hemagglutinin inhibition (HI) and titers for two smallpox antigens. The third smallpox antigen yielded better results with a 3 pulse pattern. A "majority rules" standard was used and the 2×2 pulse EP condition was utilized for the subsequent nonhuman primate studies.

Example 8

Vaccination with Multivalent Vaccine in Non-human Primates

DNA Multivalent Vaccine Elicits a Robust Antibody Response

Cynomolgus macaques were purchased from Three Springs Scientific (Perkasie, Pa.) and housed and cared for by Southern Research Institute (Birmingham, Ala.). A total of 24 macaques (14 females and 10 males) were individually housed in cages and assigned to each group based on similarity of body weights and sex. All macaques were tested negative for SIV, STLV, SRV, and HBV. Upon receipt, all animals were quarantined and acclimated to study rooms. Macaques were fed Teklad 2050C Diet during the quarantine and study periods. Feed was provided at a quantity of approximately one scoop of feed (6 to 10 biscuits) twice a day. The experimental design was in accordance with the guidelines set forth by IACUC of Southern Research Institute, the Guide for the Care and Use of Laboratory Animals, 7th Edition (Institute of Animal Resources, Commission on Life Sciences, National Research Council; National Academy Press; Washington, D.C.; 1996), and the U.S. Department of Agriculture through the Animal Welfare Act (Public Law 99-198).

Four groups of cynomolgous macaques were immunized three times, each immunization one month apart, with a multivalent DNA vaccine comprised of eight VACV Western Reserve strain genes: A4L, A27L, A33R, A56R, B5R, F9L, H3L, and L1R. One group (n=6) received a high dose (HD) of DNA (250 µg/antigen) by the intradermal (ID) route, while another group (n=6) received a low dose (LD) of DNA (125 µg/antigen) by the same route. Additionally, two groups of macaques (n=4) were immunized with either a high dose or low dose vaccine by the intramuscular (IM) route. A group (n=4) of pVAX1-immunized animals were used as a negative control. One month following the third immunization the animals were challenged with a lethal dose of the Zaire 79 strain of monkeypox virus (introducing 2×10$^7$ PFU via intravenous delivery).

Figure 34A:
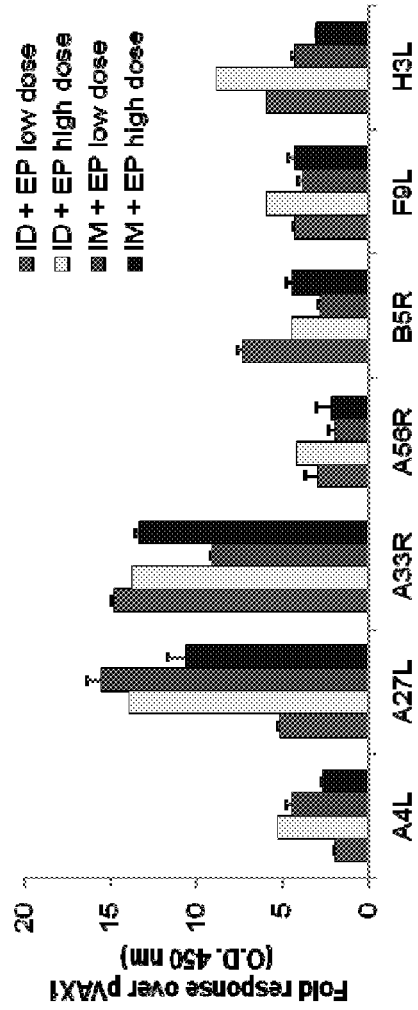
FIG. 34a displays a bar graph antibody responses for each antigen relative to pVAX1-control group.

ELISA assays were used to evaluate the antibody-specific responses for each antigen in the multivalent DNA vaccine preparation (Table 3a). Graphic representation of Table 3 can be seen in the bar graph depicted in FIG. 34a.

TABLE 3a

Antibody response measured for each antigen by ELISA.

| Antigen | pVAX1 | ID + EP low dose (fold increase) | ID + EP high dose (fold increase) | IM + EP low dose (fold increase) | IM + EP high dose (fold increase) |
|---|---|---|---|---|---|
| A4L | 0.14 ± 0.02 | 0.26 ± 0.07 (1.9) | 0.73 ± 0.23* (5.2) | 0.61 ± 0.41 (4.4) | 0.37 ± 0.17 (2.6) |
| A27L | 0.18 ± 0.04 | 0.91 ± 0.16* (5.1) | 2.53 ± 0.67* (13.9) | 2.79 ± 0.82* (15.5) | 1.92 ± 1.06 (10.6) |
| A33R | 0.13 ± 0.01 | 1.91 ± 0.24* (14.7) | 1.77 ± 0.47* (13.7) | 1.18 ± 0.10* (9.1) | 1.72 ± 0.19* (13.3) |
| A56R | 1.11 ± 0.36 | 3.27 ± 0.79 (2.9) | 4.57 ± 0.63* (4.1) | 2.07 ± 0.48* (1.9) | 2.35 ± 0.95 (2.1) |
| B5R | 0.20 ± 0.01 | 1.45 ± 0.27* (7.3) | 0.88 ± 0.28* (4.4) | 0.55 ± 0.13* (2.8) | 0.89 ± 0.40 (4.4) |
| F9L | 0.58 ± 0.13 | 2.43 ± 0.16* (4.2) | 3.41 ± 0.40* (5.9) | 2.21 ± 0.28* (3.8) | 2.4 ± 0.52* (4.2) |
| H3L | 0.13 ± 0.03 | 0.77 ± 0.11* (5.9) | 1.14 ± 0.25* (8.8) | 0.55 ± 0.01* (4.2) | 0.39 ± 0.11 (3.0) |
| L1R | 0.15 ± 0.00 | 0.17 ± 0.02 (1.1) | 0.26 ± 0.08 (1.7) | 0.19 ± 0.02 (1.3) | 0.18 ± 0.02 (1.2) |

Shown are the average O.D. readings (450 nm) with S.E.M. for each antigen as measured by ELISA. Antibody responses were measured on day 70.
*Indicates statistical significance, P < 0.05 (two-tailed T-Test with equal variance) between respective treatment group and pVAX1.
**Indicates fold increase over pVAX1 O.D. value.

Antibody responses are shown two weeks following the last vaccination. All antigens in the multivalent vaccine elicited an antibody response to varying degrees (Table 3a) irrespective of dosage and route of vaccination. A dose effect was observed for the antigens with the ID high dose (HD, 250 µg/plasmid), performing better in most cases than the low dose (LD, 125 µg/plasmid.) vaccine. For IM vaccination, antigen-specific responses were observed at both doses without a dose effect. In terms of responses, the ID route of delivery fared better than the IM delivery for the HD vaccine, with the exception of B5R which was equivalent. For the ID-HD route of delivery, we observed a 14 (A27L and A33R) and 9-fold (H3L) induction of antibody response. When the IM-HD route was used, we observed a 10.6 and 13.3 fold increase in response over controls for A27L and A33R, respectively.

In addition, antigen-specific antibody titers were measured. Most antigens in the multivalent vaccine elicited an antibody response to varying degrees irrespective of dosage and route of vaccination. See results in Table 3b, below.

TABLE 3b

Antigen-specific antibody titers

| | | Group | | | |
|---|---|---|---|---|---|
| Antigen | pVAX1 | IM-LD | ID-LD | IM-HD | ID-HD |
| A4 | <100 | 2751 | 750 | <100 | 2667 |
| A27 | <100 | 7500 | 2667 | 7500 | 6709 |
| A33 | <100 | 10000 | 10000 | 10000 | 7500 |
| A56 | <100 | 7500 | 6250 | 9063 | 11667 |
| B5 | <100 | 276 | 5017 | 1251 | 3334 |
| F9 | <100 | 626 | 3001 | 2501 | 7500 |
| H3 | <100 | 2501 | 3501 | <100 | 4167 |
| L1 | <100 | <100 | <100 | <100 | 1668 |

A dose effect was observed for the antigens with the ID-HD performing better in most cases than the ID-LD vaccine. For IM vaccination, antigen-specific responses were observed at both doses without a dose effect. In terms of responses, the ID route of delivery fared better than the IM delivery for the HD vaccine. All immunization groups failed to make substantial antibody response to L1.

B. Induction of Cell-mediated Immunity in Nonhuman Primates

Figure 34B:
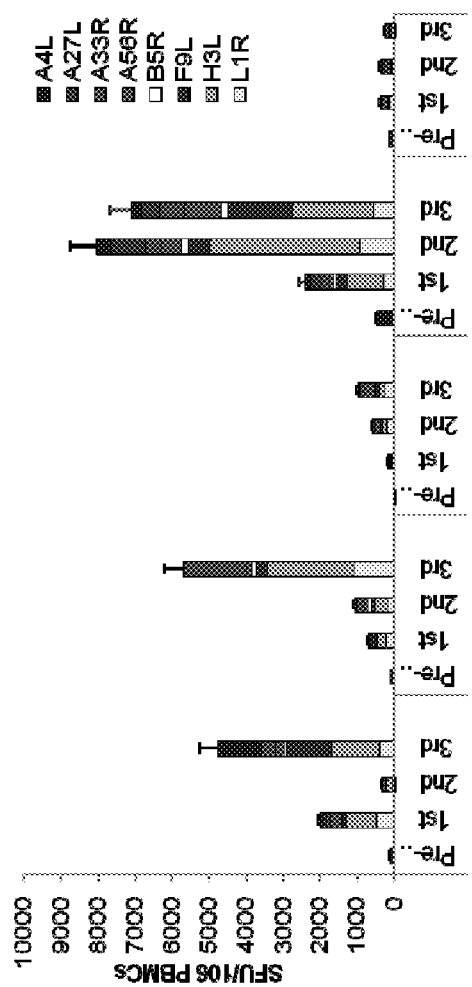
FIG. 34b displays a bar graph showing cellular response after ID and IM delivery for each vaccination (PBMCs were isolated from individual immunized macaques from each vaccination (days 0, 28, and 56) and pooled. PBMCs were stimulated with peptide pools for each antigen followed by IFN-γ ELISPOT assays.)

The cellular immune response induced by the multivalent vaccine was also evaluated (FIG. 34b). Small differences in the level of responses were noticeable between the LD and HD for ID-EP, whereas a much more pronounced dosage effect was observed following IM-EP vaccination. A significant increase in the total cellular immunity followed both ID and IM injections, with robust immune response observed following the second and third vaccinations HD injections (FIG. 34b). An augmented effect was observed for ID-HD delivery with an overall increase of 8-fold (687±31.5 vs. 5675±538.1 per $10^6$ SFU, P<0.03) in cellular response. A similar effect was observed for IM-HD delivery. Between the first and second or third IM-HD vaccination we observed a 3-fold increase in cellular responses (2388±199 vs. 8028±719 or 7098±587 per 106 SFU, P<0.02, respectively).

C. T Cell Function and Proliferation Results

Several T cell functions were assessed by intracellular cytokine staining including: IFNγ, IL-2, and TNFα production as well as CD 107a, as a surrogate marker for degranulation. Based on expense and sample limitations, the functional T cell response to two antigens were analyzed: A27 and B5. The overall magnitude of functional responses to A27 and B5 were higher in the $CD4^+$ T cell compartment than the $CD8^+$ T cell compartment. The ID-HD group had the highest $CD4^+$ T cell response with an average magnitude of 0.3±0.06% with all animals responding to at least one of the two antigens (FIG. 39a). The IM immunized animals had a lower average response although there was no significant difference in responses between the high and low dose group (0.2±0.08% and 0.2±0.1%, respectively). The ID-LD group had the lowest $CD4^+$ response (0.13±0.03%). In contrast to the $CD4^+$ response, the $CD8^+$ responses to A27 and B5 were slightly lower in magnitude (FIG. 39b). The IM-LD group had a response that was slightly higher than the ID-HD group (0.18±0.08% and 0.15±0.04%, respectively). Both the ID-LD and IM-HD had modest $CD8^+$ T cell responses (0.07±0.02% and 0.08±0.05%, respectively).

Using Boolean gating we examined the polyfunctional nature of the cellular response. In general, the responding animals made a monofuctional response, with CD107a being the predominant function, and only one animal in the IM-LD group made a 3 function $CD8^+$ T cell response to B5 (data not shown).

Another parameter of the cellular immune response is the proliferative capacity of the vaccine induced T cell response. PBMCs were isolated following the third immunization and stimulated ex vivo, and then assessed for proliferation by CFSE dilution. $CD4^+$ T cell proliferation was highest in the ID-HD group (10.2±6.2%) (FIG. 40a). The ID-LD and IM-HD groups had a low $CD4^+$ T cell response of (1.7±0.67% and 1.4±1.1%, respectively). The IM-LD did not have a response that was higher than background. Similar results were seen in the $CD8^+$ T cell compartment with the ID-HD group having the highest response (6.7±5.4%) (FIG. 40b). The ID-LD, IM-HD, and IM-LD groups had similar levels of $CD8^+$ T cell proliferation (1.6±0.69%, 1.9±1.1%, and 1.8±1.6%, respectively).

While strong IFNγ responses by ELISpot were observed in the non-human primate study; the IM immunized groups exhibited higher total IFNγ responses than the ID immunized groups. Also, the ID-HD group exhibited better $CD4^+$ and $CD8^+$ T cell proliferation compared to the other immunization groups. Polyfunctional analysis of vaccine-induced immune responses to A27 and B5 demonstrated higher overall $CD4^+$ T cell responses induced by ID-HD vaccination while IM-LD vaccination yielded higher responses in the $CD8^+$ T cell compartment. However, regardless of immunization route or dose, both $CD4^+$ and $CD8^+$ T cells were predominantly monofunctional with a probable association with a killing phenotype. Although no animal made a four-functional response to A27 and B5, based on experiences with IM electroporation with HIV antigens (as reported in the art) the functional profile of the vaccine-induced immune response observed in this study is most likely an antigen-specific phenomenon.

Example 9

Challenge: Vaccinated Nonhuman Primates and Challenge with Monkeypox Zaire 79

A. Multivalent DNA Vaccine Protects Nonhuman Primates from Severe Monkeypox Disease To fully evaluate the efficacy of the response, animals were challenged with NR-523 isolate of Zaire 79 strain of monkeypox virus. The multivalent vaccine provided protection irrespective of route of administration (Table 4).

TABLE 4

Development of pock lesions following intravenous challenge with monkeypox virus.

| Vaccine | Macaque No | Day post-challenge | | | | | | | | |
|---|---|---|---|---|---|---|---|---|---|---|
| | | 0 | 3 | 6 | 9 | 12 | 15 | 18 | 21 | 24 | 27 |
| pVAX1 (n = 4) | 4384 | 0 | 0 | 176 | TNTC | TNTC | TNTC | TNTC | 120 | TNTC (RE)** | 93 |
| | 4392 | 0 | 0 | TNTC | TNTC | TNTC | TNTC | — | — | — | — |
| | 4393 | 0 | 0 | TNTC | TNTC | TNTC | — | — | — | — | — |
| | 4403 | 0 | 0 | TNTC | TNTC | — | — | — | — | — | — |
| ID + EP low dose (n = 6) | 4385 | 0 | 0 | 102 | 435 | 422 | 422 | 378 | 14 | 12 | 0 |
| | 4388 | 0 | 0 | 16 | 65 | 89 | 26 | 11 | 0 | 0 | 0 |
| | 4395 | 0 | 0 | 113 | TNTC | TNTC | TNTC | 272 | 58 | 49 | 0 |
| | 4396 | 0 | 0 | 123 | 304 | 464 | 464 | 301 | 85 | 62 | 0 |
| | 4404 | 0 | 0 | 107 | 263 | 207 | 31 | 12 | 0 | 0 | 0 |
| | 4406 | 0 | 0 | 75 | 195 | 213 | 53 | 16 | 0 | 0 | 0 |
| ID + EP high dose (n = 6) | 4386 | 0 | 0 | 84 | 201 | 231 | 95 | 27 | 0 | 0 | 0 |
| | 4389 | 0 | 0 | 45 | 182 | 244 | 0 (RE)* (RE)* | 53 | 0 | 0 | 0 |
| | 4390 | 0 | 0 | 3 | 12 | 11 | 0 | 0 | 0 | 0 | 0 |
| | 4397 | 0 | 0 | 59 | 149 | 153 | 144 | 71 | 4 | 1 | 0 |

TABLE 4-continued

Development of pock lesions following intravenous challenge with monkeypox virus.

| Vaccine | Macaque No | Day post-challenge | | | | | | | | |
|---|---|---|---|---|---|---|---|---|---|---|
| | | 0 | 3 | 6 | 9 | 12 | 15 | 18 | 21 | 24 | 27 |
| | 4398 | 0 | 0 | 17 | 30 | 30 | 3 | 0 | 0 | 0 | 0 |
| | 4407 | 0 | 0 | 109 | 223 | 196 | 0 | 0 | 0 | 0 | 0 |
| IM + EP low dose (n = 4) | 4387 | 0 | 0 | TNTC | 150 | 156 | 170 | 22 | 0 | 0 | 0 |
| | 4394 | 0 | 0 | TNTC | TNTC | TNTC | TNTC | 22 | 8 | 8 | 0 |
| | 4400 | 0 | 0 | 122 | 248 | 244 | 227 | 69 | 0 | 0 | 0 |
| | 4402 | 0 | 0 | 8 | TNTC | 137 | 35 | 0 | 0 | 0 | 0 |
| IM + EP high dose (n = 4) | 4391 | 0 | 0 | 28 | 79 | 61 | 16 | 0 | 0 | 0 | 0 |
| | 4399 | 0 | 0 | 56 | 206 | 234 | 234 | 32 | 0 | 0 | 0 |
| | 4401 | 0 | 0 | 21 | 132 | 130 | 149 | 70 | 5 | 4 | 2 |
| | 4405 | 0 | 0 | 81 | 172 | 175 | 113 | 0 | 0 | 0 | 0 |

TNTC = too numerous to count,
RE = Recording Error.
*After reviewing pictures of 4389 at day 15 some lesions were noticeable and therefore should not be stated as 0 lesions. This is obviously a recording error (RE). However, none of the pictures from day 18 show evidence of lesions although not all the regions were represented.
**After reviewing pictures of 4384 at day 24, there was no evidence of TNTC in the back which was 2 lesions only at day 21. Since lesions were clearly being resolved by this time point it is unlikely that total lesion counts were TNTC, therefore it appears that the TNTC for Day 24 is a recording error.

Figure 35A:
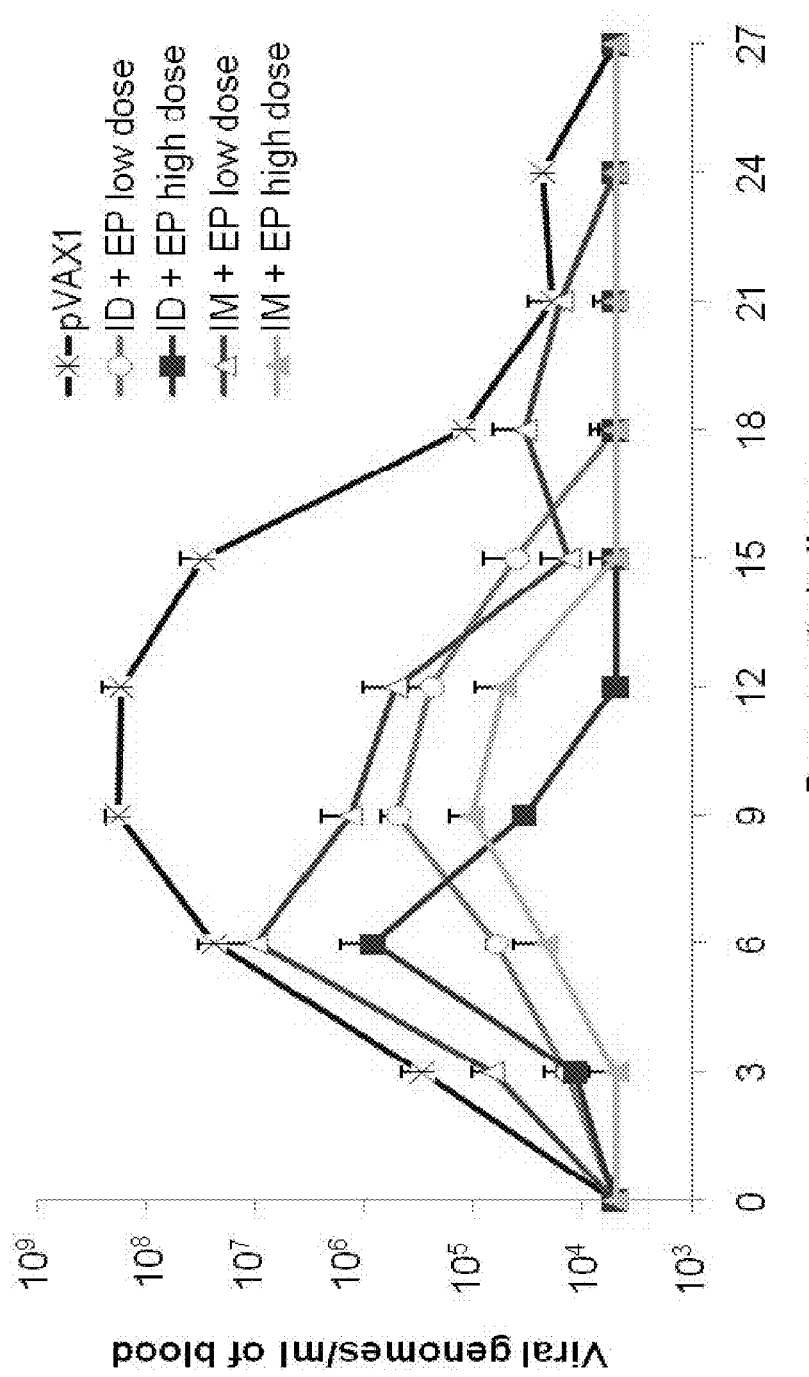
FIG. 35a displays a graph showing levels of viremia in vaccinated macaques following challenge. The number of monkeypox virus genomes per ml of blood was determined by quantitative TaqMan 3'-minor groove binder PCR. The lower limit of detection was 5000 genomes/ml of blood. Average values with ±SEM. A4L responses were not reported due to high background responses in pre-immune samples.

The data can be seen graphically in FIG. 35b2.

The vaccine substantially reduced the number of lesions and provided 100% protection from mortality at both low and high doses, compared to the innumerable number of lesions and 75% mortality recorded in the pVAX1-treated control group. At peak lesion count, 3 of the 4 animals in the pVAX1-treated animals had innumerable lesions; the disease was fatal for the $4^{th}$ animal. Only one macaque from the control group survived the challenge but with lesions still present at the end of the observation period (day 27 post-challenge). In vaccinated animals, the lesions started to resolve by day 15, with the effect more pronounced for the animals receiving ID-HD injection: at day 21, only one of the six animals had lesions (with only 4 lesions observed). On the last day of observation (day 27), none of the animals showed signs of monkeypox lesions. Treatment with ID-LD resulted in three of the six monkeys being pox free by day 21, with all of the animals having resolved their lesions completely by day 27. When nonhuman primates were treated by IM-EP, signs of healing were apparent slightly earlier. By day 21, three of the four macaques were lesion free. At the end of the challenge study one monkey had 2 remaining lesions. Treatment by IM-LD vaccine was also effective with one of the four monkeys having no lesions by day 18. By day 21, three of the four monkeys were pox free while one monkey had 8 lesions. By the end of the observation time all four monkeys in the IM-LD group were lesion free.

B. Reduction in the Level of Viremia Elicited by Multivalent Vaccine

All macaques demonstrated an established monkeypox virus infection with peak viremia levels developing 6 to 9 days post-challenge (FIG. 35a). pVAX1-control animals developed typical symptoms of monkeypox disease with three of the four animals being euthanized due to severity of the disease. Level of viremia peaked in pVAX1-vaccinated animals between 7.5 and 8.5 logs at 9 and 12 days post-challenge, respectively. The macaque that survived the challenge (#4384) appeared to have some level of control of viremia. On day 21, the level of viremia was less than 1 log above the HD-vaccinated animals. In contrast, animals that were vaccinated had a significant reduction in the level of viremia by a magnitude of at least 3 logs on day 9 ($P<0.05$ one-way ANOVA) with undetectable levels (<5000 copies per mL) observed at the end of the study. By day 15, four of the six animals in the ID-HD group and 100% of the animals in the IM-HD group had undetectable levels of viremia compared to 50% for both LD vaccinations. By day 18, only one of the macaques in both vaccination groups had detectable levels of viremia. Thus, these findings demonstrate the protective efficacy of the DNA vaccine in controlling monkeypox virus viremia and prevention of severe disease.

C. Induction of Anti-VACV Antibodies Elicited by Multivalent Vaccine

Figure 36:
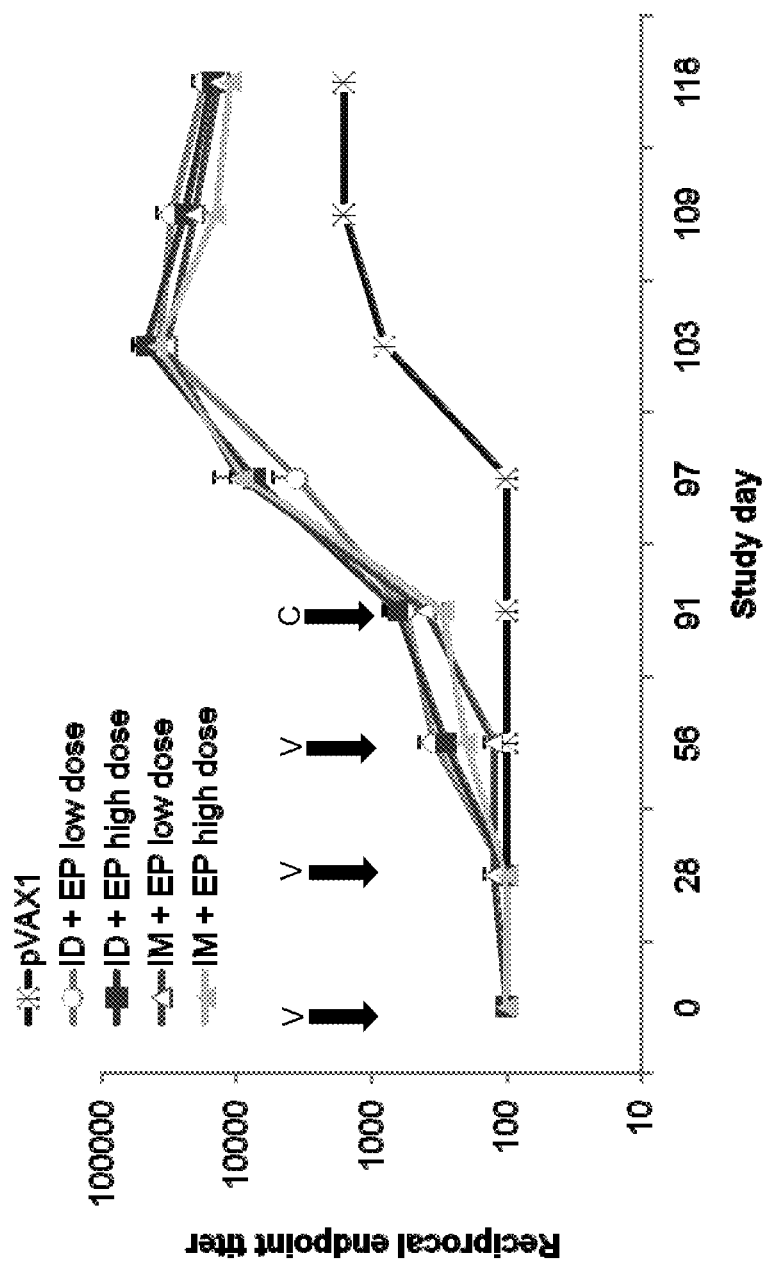

The detection of antibodies induced upon DNA vaccine and monkeypox virus challenge was measured by ELISA using purified, inactivated whole VACV as a coating antigen (FIG. 36). Low level titers of virus-specific VACV-specific antibodies were detected on day 28 in animals that received the DNA vaccine, with all animals having a 1:100 endpoint titer for both vaccination groups and dosages. Antibody titers started to increase thereafter with average endpoint titers of 1:633 and 1:300 on day 91 for ID-HD and IM-HD delivery routes, respectively, with insignificant differences existing between dosages. Dramatic increases in anti-VACV antibody titers were observed post-challenge in vaccinated macaques. A nearly 100-fold increase over pVAX1-vaccinated animals was observed in vaccinated macaques 6 days post-challenge (study day 97) with endpoint titers of nearly 1:10,000 in HD-vaccinated macaques. Lower or similar endpoint titers were observed for animals vaccinated with the LD with average endpoint titers of 1:3600±1867 and 1:8800±2400 for ID and IM injection, respectively. In contrast, pVAX1-treated animals did not show a significant response until 12 days following challenge (study day 103), with an average maximum endpoint titer of 1:800. The macaque that survived the challenge had a maximum endpoint antibody titer of only 1:1600 on day 18 post-challenge (study day 109).

D. Induction of Neutralizing Antibody Titers Elicited by Multivalent Vaccine

Having identified binding antibodies to whole VACV, their ability to neutralize monkeypox virus in an in vitro functional PRNT assay was investigated to determine the role of vaccine-induced antibodies in the protection against monkeypox virus challenge in vivo. Monkeypox virus neutralizing antibody titers were measured in the different groups (see Table 5).

TABLE 5

Pre- and post-challenge neutralizing antibody titers against monkeypox virus.

| Vaccine | Macaque No. | Study day* | | | | | | | | | | |
|---|---|---|---|---|---|---|---|---|---|---|---|---|
| | | 0 | 14 | 28 | 42 | 56 | 70 | 91 | 97 | 103 | 109 | 118 |
| pVAX1 | 4384 | 0 | 0 | 0 | 0 | 0 | 0 | 0 | 1813 | 4480 | 10240 | 10240 |
| (n = 4) | 4392 | 0 | 0 | 0 | 0 | 0 | 0 | 0 | 560 | 5120 | | |
| | 4393 | 0 | 0 | 0 | 0 | 0 | 0 | 0 | 202 | 2133 | | |
| | 4403 | 0 | 0 | 0 | 0 | 0 | 0 | 0 | 371 | | | |
| ID + EP | 4385 | 0 | 0 | 0 | 200 | 0 | 0 | 0 | 6602 | 9387 | 7040 | 6400 |
| low dose | 4388 | 0 | 0 | 0 | 93 | 74 | 263 | 256 | 7529 | 10240 | 9788 | 6400 |
| (n = 6) | 4395 | 0 | 0 | 0 | 130 | 0 | 25 | 0 | 2560 | 10240 | 10240 | 10240 |
| | 4396 | 0 | 0 | 0 | 0 | 15 | 105 | 0 | 2560 | 10240 | 10240 | 10240 |
| | 4404 | 0 | 0 | 0 | 110 | 37 | 150 | 74 | 5440 | 7936 | 8145 | 8533 |
| | 4406 | 0 | 0 | 0 | 0 | 0 | 0 | 0 | 4230 | 10240 | 8433 | 10240 |
| ID + EP | 4386 | 0 | 0 | 0 | 40 | 27 | 147 | 30 | 6901 | 10240 | 10240 | 10240 |
| high dose | 4389 | 0 | 0 | 0 | 120 | 13 | 34 | 29 | 5565 | 9472 | 10240 | 7680 |
| (n = 6) | 4390 | 0 | 0 | 0 | 427 | 74 | 434 | 337 | 5547 | 7680 | 5973 | 6400 |
| | 4397 | 0 | 0 | 0 | 197 | 160 | 580 | 151 | 5353 | 10240 | 10240 | 10240 |
| | 4398 | 0 | 0 | 0 | 587 | 592 | 2320 | 1024 | 7569 | 10240 | 10240 | 10240 |
| | 4407 | 0 | 0 | 0 | 0 | 0 | 100 | 31 | 10240 | 6400 | 10240 | 10240 |
| IM + EP | 4387 | 0 | 0 | 0 | 70 | 16 | 91 | 26 | 8800 | 10240 | 10240 | 5722 |
| low dose | 4394 | 0 | 0 | 0 | 0 | 0 | 18 | 16 | 10240 | 7680 | 10240 | 10240 |
| (n = 4) | 4400 | 0 | 0 | 0 | 10 | 36 | 126 | 0 | 4628 | 10240 | 10240 | 10240 |
| | 4402 | 0 | 0 | 0 | 0 | 15 | 160 | 40 | 1057 | 10240 | 10240 | 10240 |
| IM + EP | 4391 | 0 | 0 | 0 | 400 | 188 | 453 | 120 | 6827 | 10240 | 10240 | 10240 |
| high dose | 4399 | 0 | 0 | 0 | 0 | 0 | 23 | 0 | 10240 | 8704 | 10240 | 10240 |
| (n = 4) | 4401 | 0 | 0 | 0 | 0 | 0 | 213 | 0 | 5231 | 5760 | 8237 | 10240 |
| | 4405 | 0 | 160 | 0 | 105 | 74 | 544 | 36 | 6720 | 10240 | 10240 | 9143 |

*Titers are expressed as $PRNT_{50}$ values. Animals were vaccinated on days 0, 28, and 56, and challenged on day 91 (challenge day 0). Days 97, 103, 109, and 118 correspond to challenge days 6, 12, 18, and 27, respectively.

Figure 37:
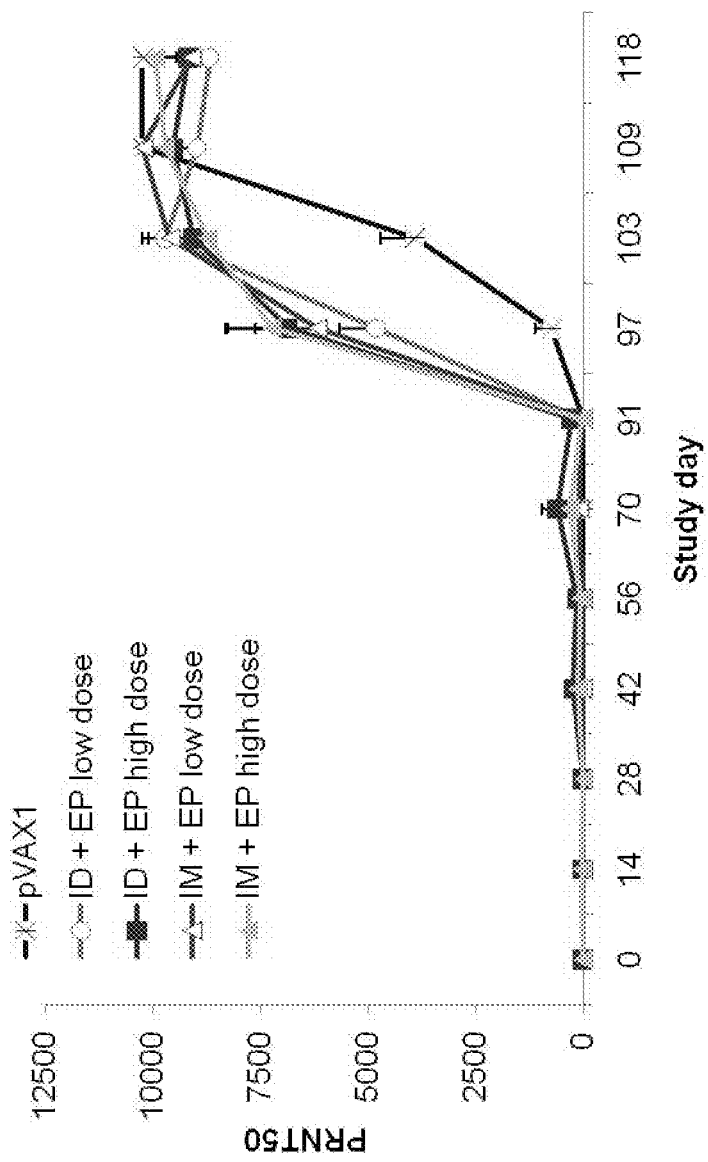

Serum collected from pVAX1-treated control animals prior to challenge was unable to neutralize virus. However, 6 days post-challenge (study day 97) all the macaques started to show a detectable titer. The control macaque that survived the challenge had the greatest neutralizing antibody titer. In contrast, animals vaccinated with the multivalent vaccine started to show a moderate neutralizing antibody response two weeks following the second vaccination (day 42), irrespective of the route of vaccination or dosage. Importantly, the neutralizing antibody response was greatly and rapidly augmented following challenge. The graph of the results can be seen in FIG. 37. As expected, the HD vaccine elicited a greater antibody response than the LD vaccine for all time points (Table 5).

Figure 38:
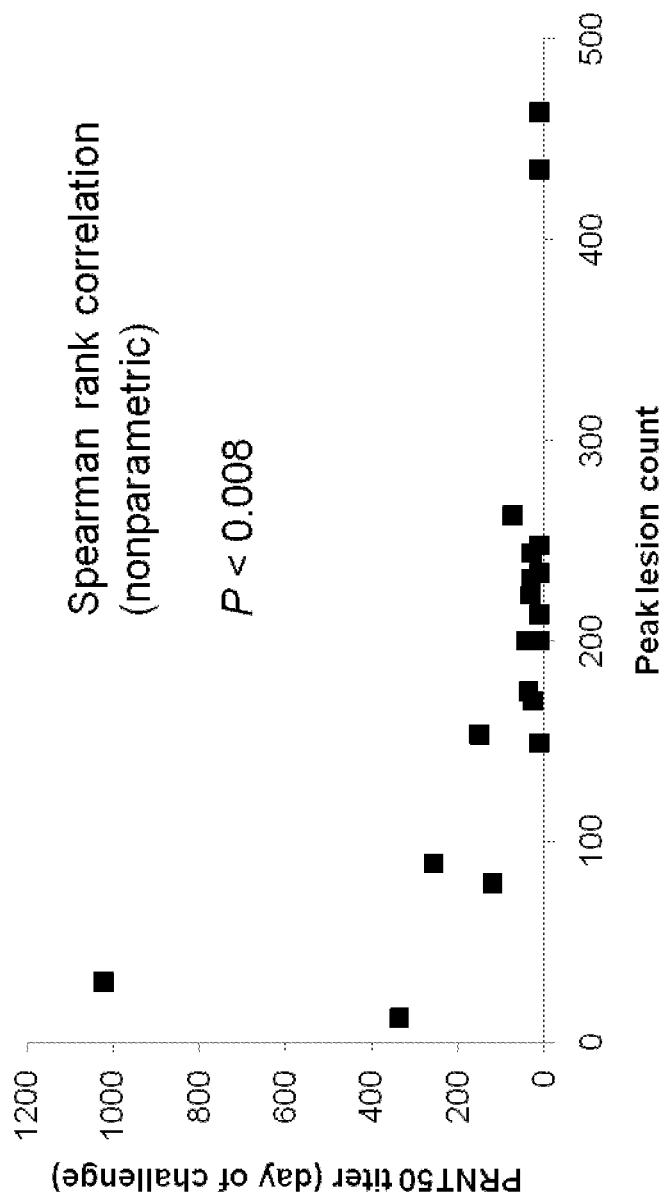

Furthermore, neutralizing antibody titers correlated with lesion count scores (Spearman Rank Correlation, nonparametric $P<0.008$—See FIG. 38).

Example 10

Clinical Observations Following Monkeypox Challenge

The pVAX1-treated animals experienced significant weight loss, elevated body temperature, depression, and lethargy during the acute phase of the infection. The most significant weight loss was observed on day 12 post-challenge when pox lesions and viremia peaked (Table 6).

TABLE 6

Body weight changes following intravenous challenge with monkeypox virus.

| Vaccine | Macaque No. | Day post-challenge* | | | | | | | | | |
|---|---|---|---|---|---|---|---|---|---|---|---|
| | | 0 | 3 | 6 | 9 | 12 | 15 | 18 | 21 | 24 | 27 |
| pVAX1 | 4384 | 3.38 | −1.18 | −2.37 | −5.9 | −5.62 | −0.89 | −2.66 | 2.66 | 2.07 | 0.89 |
| (n = 4) | 4392 | 4.16 | −4.56 | 1.44 | −9.38 | −11.06 | −10.34 | | | | |
| | 4393 | 3.84 | −1.04 | −3.38 | −10.16 | −8.85 | | | | | |
| | 4403 | 3.2 | 0.62 | −0.93 | −7.5 | −9.38 | | | | | |
| ID + EP | 4385 | 3.47 | −2.31 | −2.31 | −4.32 | −8.07 | −2.02 | −0.86 | 2.02 | 2.02 | 0.58 |
| low | 4388 | 3.01 | −0.66 | −2.33 | −2.99 | −4.98 | −4.32 | −3.99 | −1.99 | −1.00 | −0.33 |
| dose | 4395 | 4 | −0.50 | 0.00 | 0.00 | 1.00 | 4.50 | 5.75 | 6.50 | 8.00 | 8.75 |
| (n = 6) | 4396 | 4.36 | −1.83 | −0.46 | 0.46 | −1.38 | 0.92 | 0.92 | 7.57 | 8.03 | 8.72 |
| | 4404 | 3.11 | −1.29 | −0.96 | −5.14 | −2.89 | −1.61 | −0.64 | 1.29 | 2.25 | 2.89 |
| | 4406 | 2.98 | 0.00 | −0.67 | −3.02 | −1.34 | 1.68 | 1.68 | 4.70 | 2.35 | 2.01 |
| ID + EP | 4386 | 3 | −0.67 | 0.33 | −2.33 | −5.67 | 1.33 | 2.33 | 5.33 | 5.67 | 5.33 |
| high | 4389 | 3.22 | −2.17 | −1.86 | −6.21 | −10.56 | −4.66 | −5.90 | −3.11 | −1.55 | −0.93 |
| dose | 4390 | 3.05 | −6.23 | −0.66 | 0.98 | −0.66 | 1.97 | 1.31 | 0.98 | 0.33 | 0.00 |
| (n = 6) | 4397 | 4.04 | 0.74 | 1.49 | 0.50 | 0.74 | 1.49 | 0.25 | 2.23 | 0.50 | 0.99 |
| | 4398 | 3.93 | 9.92 | 5.34 | 6.36 | 6.62 | 8.40 | 15.01 | 10.69 | 11.70 | 12.98 |
| | 4407 | 2.73 | 0.00 | 1.47 | 0.73 | 1.47 | 2.56 | 2.56 | −0.37 | 1.83 | −3.66 |
| IM + EP | 4387 | 2.94 | −4.76 | −3.06 | −2.38 | −3.74 | 1.36 | 1.70 | 5.78 | 12.24 | 1.70 |
| low | 4394 | 3.61 | −1.39 | −1.11 | −1.94 | −4.99 | 1.94 | 2.22 | 5.54 | 3.88 | 2.77 |
| dose | 4400 | 4.36 | −0.46 | 0.00 | −0.92 | −2.29 | 1.83 | 1.83 | 0.46 | 1.83 | 0.46 |
| (n = 4) | 4402 | 3.17 | −2.52 | −5.05 | −9.15 | −12.93 | −9.15 | −3.15 | −7.57 | −8.52 | −11.99 |

TABLE 6-continued

Body weight changes following intravenous challenge with monkeypox virus.

| Vaccine | Macaque No. | 0 | 3 | 6 | 9 | 12 | 15 | 18 | 21 | 24 | 27 |
|---|---|---|---|---|---|---|---|---|---|---|---|
| IM + EP | 4391 | 3.88 | 1.55 | 1.55 | 0.52 | 1.03 | 2.32 | −10.05 | 3.61 | 4.64 | 3.87 |
| high | 4399 | 4.28 | −1.17 | −0.70 | −2.34 | −5.37 | −1.17 | −0.23 | 0.23 | 1.40 | 0.70 |
| dose | 4401 | 3.37 | −0.59 | −0.30 | −0.59 | −3.56 | 0.30 | −0.30 | 0.89 | −1.78 | −2.97 |
| (n = 4) | 4405 | 2.48 | 10.89 | 13.31 | 14.52 | 14.52 | 20.16 | 22.58 | 26.61 | 23.39 | 23.39 |

*Numbers in columns from challenge Day 6 to 27 are represented as % body weight change relative to Day 0. Body weight is given in Day 0 column.

On day 12 of the challenge, the average weight loss was 8.73% (weight loss range from 5.6 to 11.1% compared to pre-challenge body weight). The one macaque surviving (#4384) in the group eventually regained weight, but not until day 21 post-challenge. In contrast, vaccinated animals did not experience significant weight loss post-challenge. A loss of body weight was more prominent in the animals treated with both the LD vaccines than in the HD-vaccinated animals. For animals treated with the ID-HD vaccine, a weight variation was observed on day 12 post-challenge with an average loss of 1.34% over pre-challenge body weight. This same day, animals vaccinated via the IM route experienced a weight gain of 1.7% over pre-challenge weight. The animals vaccinated with the LD vaccine experienced a greater weight loss that that observed for the HD-vaccinated animals. For ID and IM vaccination, animals experienced an average SEM loss of 2.9%±1.3 and 6.0%±2.38, respectively.

For the pVAX1-treated animals, an increase in body temperature was observed up to day 12 post-challenge (Data Not Shown). The maximum increase in body temperature was observed on day 3 post-challenge, with a mean temperature of 103.1° F. (range: 101.5 to 104.4° F.). The macaque surviving the challenge had normal body temperature by day 27. Irrespective of the route of vaccination and dosage, vaccinated macaque temperatures fluctuated throughout the challenge period, as expected. However, the average temperature in vaccinated animals was maintained within normal body temperature (99-102° F.) throughout the challenge (data not shown).

Clinical parameters: Complete blood counts (CBC) monitoring throughout the study showed insignificant changes in hematological parameters during monkeypox challenge. Control animals that were euthanized due to monkeypox disease had elevated white blood cells (WBC) of 58.2% (#4403, 11,500 vs. 18,200 per μL), 65.6% (#4392, 6,100 vs. 10,100 per μL), and 121% (#4393, 8,600 vs. 19,000 per μL) on day 12 when viremia levels peaked, compared to pre-challenge levels. Vaccinated animals also had elevated WBC numbers to the same extent on day 12 with an average percent increase of 69.4±15.8, 68.8±15.6, 80.9±17.2, 70.0±28.0 for ID-LD, ID-HD, IM-LD, IM-HD, respectively, over pre-challenge levels. By the end of the study, most vaccinated animals from each group had their WBC numbers return to pre-challenge levels, whereas the surviving macaque from the control group continued to have elevated WBC number of 22,300 per μL.

The invention claimed is:

1. A method of inducing a protective immune response in a mammal to pox virus, including a neutralizing antibody response, comprising:

injecting into tissue of said mammal by intradermal injection a DNA vaccine comprising eight distinct DNA plasmids, wherein one DNA plasmid comprises a nucleotide sequence that encodes A4L, one DNA plasmid comprises a nucleotide sequence that encodes A27L, one DNA plasmid comprises a nucleotide sequence that encodes B5R, one DNA plasmid comprises a nucleotide sequence that encodes A33R, one DNA plasmid comprises a nucleotide sequence that encodes A56R, one DNA plasmid comprises a nucleotide sequence that encodes F9L, one DNA plasmid comprises a nucleotide sequence that encodes H3L, and one DNA plasmid comprises a nucleotide sequence that encodes L1R; and electroporating said tissue with an electroporating amount of electrical energy.

2. The method of claim 1, wherein the electroporating step comprises delivering a constant current to said tissue.

3. The method of claim 2, wherein the electroporating step comprises delivering 0.2 A of current.

4. The method of claim 1, further comprising repeating said injecting step and electroporating step.

5. The method of claim 1, wherein the eight distinct DNA plasmids comprise: pGX4001, pGX4002, pGX4003, pGX4004, pGX4005, pGX4006, pGX4007, and pGX4008.

6. The method of claim 1, wherein said method induces a protective immune response in a mammal to smallpox virus.

7. The method of claim 1, wherein said nucleotide sequence that encodes A4L is SEQ ID NO: 1, said nucleotide sequence that encodes A27L is SEQ ID NO: 3, said nucleotide sequence that encodes B5R is SEQ ID NO: 5, said nucleotide sequence that encodes A33R is SEQ ID NO: 7, said nucleotide sequence that encodes A56R is SEQ ID NO: 9, said nucleotide sequence that encodes F9L is SEQ ID NO: 11, said nucleotide sequence that encodes H3L is SEQ ID NO: 13 (H3L), and said nucleotide sequence that encodes L1R is or SEQ ID NO: 15.

8. The method of claim 1, wherein said A4L has the amino acid sequence of SEQ ID NO: 2, said A27L has the amino acid sequence of SEQ ID NO: 4, said B5R has the amino acid sequence of SEQ ID NO: 6, said A33R has the amino acid sequence of SEQ ID NO: 8, said A56R has the amino acid sequence of SEQ ID NO: 10, said F9L has the amino acid sequence of SEQ ID NO: 12, said H3L has the amino acid sequence of SEQ ID NO: 14 and said L1R has the amino acid sequence of SEQ ID NO: 16.

9. The method of claim 1, wherein each of said DNA plasmids is present at a dose greater than 50 μg.

10. The method of claim 1, wherein each of said DNA plasmids is present at a dose of 125 μg.

11. The method of claim 1, further comprising administration of a nucleic acid sequence that encodes IL-8, IL-12, IL-15, IL-18, IL-28, MCP-1, MIP-1α, MIP-1p, RANTES, RANK, RANK LIGAND, Ox40, Ox40 LIGAND, CTACK, TECK, or MEC, or a combination thereof.

12. The method of claim 1, further comprising administration of a nucleic acid sequence that encodes IL-12, IL-15, IL-28, or RANTES.

13. The method of claim 5, wherein each of said DNA plasmids is present at a dose of 125 μg.

14. A method of inducing a protective immune response in a mammal to pox virus, including a neutralizing antibody response, comprising:
   injecting into tissue of said mammal by intradermal injection of a DNA vaccine comprising one or more plasmids that collectively comprise a nucleotide sequence that encodes VACV antigen A4L, a nucleotide sequence that encodes VACV antigen A27L, a nucleotide sequence that encodes VACV antigen B5R, a nucleotide sequence that encodes VACV antigen A33R, a nucleotide sequence that encodes VACV antigen A56R, a nucleotide sequence that encodes VACV antigen F9L, a nucleotide sequence that encodes VACV antigen H3L and a nucleotide sequence that encodes VACV antigen L1R, and
   electroporating said tissue with an electroporating amount of electrical energy.

15. The method of claim 14, wherein the electroporating step comprises delivering a constant current to said tissue.

16. The method of claim 15, wherein the electroporating step comprises delivering 0.2 A of current.

17. The method of claim 14, further comprising repeating said injecting step and electroporating step.

18. The method of claim 14, wherein said nucleotide sequence that encodes A4L is SEQ ID NO: 1, said nucleotide sequence that encodes A27L is SEQ ID NO: 3, said nucleotide sequence that encodes B5R is SEQ ID NO: 5, said nucleotide sequence that encodes A33R is SEQ ID NO: 7, said nucleotide sequence that encodes A56R is SEQ ID NO: 9, said nucleotide sequence that encodes F9L is SEQ ID NO: 11, said nucleotide sequence that encodes H3L is SEQ ID NO: 13 and said nucleotide sequence that encodes L1R is or SEQ ID NO: 15.

19. The method of claim 18, wherein each of said DNA plasmids is present at a dose of 125 μg.

20. The method of claim 14, wherein said A4L has the amino acid sequence of SEQ ID NO: 2, said A27L has the amino acid sequence of SEQ ID NO: 4, said B5R has the amino acid sequence of SEQ ID NO: 6, said A33R has the amino acid sequence of SEQ ID NO: 8, said A56R has the amino acid sequence of SEQ ID NO: 10, said F9L has the amino acid sequence of SEQ ID NO: 12, said H3L has the amino acid sequence of SEQ ID NO: 14 and said L1R has the amino acid sequence of SEQ ID NO: 16.

21. The method of claim 14, wherein said method induces a protective immune response in a mammal to smallpox virus.

* * * * *

SEQUENCE LISTING

```
<160> NUMBER OF SEQ ID NOS: 20

<210> SEQ ID NO 1
<211> LENGTH: 924
<212> TYPE: DNA
<213> ORGANISM: Artificial Sequence
<220> FEATURE:
<223> OTHER INFORMATION: Synthetic smallpox vaccine sequence 1

<400> SEQUENCE: 1
atggactgga cctggatcct gttcctggtg gccgctgcca caagggtgca cagcgatttc      60
ttcaacaagt tcagccaggg cctggccgag agcagcaccc ccaagagcag catctactac     120
agcgaggaaa aggaccccga caccaagaag gacgaggcca tcgagatcgg cctgaagagc     180
caggaaagct actaccagcg gcagctgcgg gagcagctgg cccgggacaa catgaccgtg     240
gccagccggc agcccatcca gccctgcag cccaccatcc acatcacccc ccagcccgtg     300
cctaccgcca cccctgcccc catcctgctg cccagcagca ccgtgcccac ccccaagccc     360
cggcagcaga ccaacaccag cagcgacatg agcaacctgt tcgactggct gtccgaggac     420
accgacgccc ctgccagcag cctgctgcct gccctgaccc ccagcaacgc cgtgcaggac     480
atcatcagca agttcaacaa ggaccagaaa accaccaccc ccccagcac ccagccctcc     540 cagaccctgc ccaccaccac ctgcacccag cagagcgacg gcaacatcag ctgcaccacc     600
```

```
                                                       -continued cccaccgtga ccccccctca gccccccatc gtggccaccg tgtgcacccc cacccctacc      660
ggcggcaccg tgtgtaccac cgcccagcag aaccccaacc ccggagccgc cagccagcag      720
aatctggacg acatggccct gaaggacctg atgagcaacg tggagcggga catgcatcag      780
ctgcaggccg agaccaacga cctggtgacc aacgtgtacg acgcccggga gtacaccagg      840
cgggccatcg accagatcct gcagctggtc aagggcttcg agcggttcca gaagtacccc      900
tacgacgtcc ccgactacgc ctga                                             924
```

<210> SEQ ID NO 2
<211> LENGTH: 307
<212> TYPE: PRT
<213> ORGANISM: Artificial Sequence
<220> FEATURE:
<223> OTHER INFORMATION: Synthetic smallpox vaccine sequence 1

<400> SEQUENCE: 2

```
Met Asp Trp Thr Trp Ile Leu Phe Leu Val Ala Ala Thr Arg Val
1               5                   10                  15

His Ser Asp Phe Phe Asn Lys Phe Ser Gln Gly Leu Ala Glu Ser Ser
                20                  25                  30

Thr Pro Lys Ser Ser Ile Tyr Tyr Ser Glu Glu Lys Asp Pro Asp Thr
            35                  40                  45

Lys Lys Asp Glu Ala Ile Glu Ile Gly Leu Lys Ser Gln Glu Ser Tyr
        50                  55                  60

Tyr Gln Arg Gln Leu Arg Glu Gln Leu Ala Arg Asp Asn Met Thr Val
65                  70                  75                  80

Ala Ser Arg Gln Pro Ile Gln Pro Leu Gln Pro Thr Ile His Ile Thr
                85                  90                  95

Pro Gln Pro Val Pro Thr Ala Thr Pro Ala Pro Ile Leu Leu Pro Ser
            100                 105                 110

Ser Thr Val Pro Thr Pro Lys Pro Arg Gln Gln Thr Asn Thr Ser Ser
        115                 120                 125

Asp Met Ser Asn Leu Phe Asp Trp Leu Ser Glu Asp Thr Asp Ala Pro
    130                 135                 140

Ala Ser Ser Leu Leu Pro Ala Leu Thr Pro Ser Asn Ala Val Gln Asp
145                 150                 155                 160

Ile Ile Ser Lys Phe Asn Lys Asp Gln Lys Thr Thr Thr Pro Pro Ser
                165                 170                 175

Thr Gln Pro Ser Gln Thr Leu Pro Thr Thr Thr Cys Thr Gln Gln Ser
            180                 185                 190

Asp Gly Asn Ile Ser Cys Thr Thr Pro Thr Val Thr Pro Pro Gln Pro
        195                 200                 205

Pro Ile Val Ala Thr Val Cys Thr Pro Thr Pro Thr Gly Gly Thr Val
    210                 215                 220

Cys Thr Thr Ala Gln Gln Asn Pro Asn Pro Gly Ala Ala Ser Gln Gln
225                 230                 235                 240

Asn Leu Asp Asp Met Ala Leu Lys Asp Leu Met Ser Asn Val Glu Arg
                245                 250                 255

Asp Met His Gln Leu Gln Ala Glu Thr Asn Asp Leu Val Thr Asn Val
            260                 265                 270

Tyr Asp Ala Arg Glu Tyr Thr Arg Arg Ala Ile Asp Gln Ile Leu Gln
        275                 280                 285

Leu Val Lys Gly Phe Glu Arg Phe Gln Lys Tyr Pro Tyr Asp Val Pro
    290                 295                 300

Asp Tyr Ala
```

<210> SEQ ID NO 3
<211> LENGTH: 411
<212> TYPE: DNA
<213> ORGANISM: Artificial Sequence
<220> FEATURE:
<223> OTHER INFORMATION: Synthetic smallpox vaccine sequence 2

<400> SEQUENCE: 3

```
atggactgga cctggatcct gttcctggtg ccgctgcca caagggtgca cagcgacggc    60
accctgttcc ccggcgacga cgacctggcc atccccgcca ccgagttctt cagcaccaag   120
gccgccaaga agcccgaggc caagcgggag gccatcgtga aggccgacga ggacgacaac   180
gaggaaaccc tgaagcagcg gctgaccaac ctggaaaaga aaatcaccaa cgtgaccacc   240
aagttcgagc agatcgagaa gtgctgcaag cggaacgacg aggtgctgtt ccggctggaa   300
aaccacgccg agaccctgag ggccgccatg atcagcctgg ccaagaaaat cgacgtgcag   360
accggcaggc ggccctacga gtacccctac gacgtgcccg actacgcctg a            411
```

<210> SEQ ID NO 4
<211> LENGTH: 136
<212> TYPE: PRT
<213> ORGANISM: Artificial Sequence
<220> FEATURE:
<223> OTHER INFORMATION: Synthetic smallpox vaccine sequence 2

<400> SEQUENCE: 4

Met Asp Trp Thr Trp Ile Leu Phe Leu Val Ala Ala Thr Arg Val
1               5                   10                  15

His Ser Asp Gly Thr Leu Phe Pro Gly Asp Asp Asp Leu Ala Ile Pro
            20                  25                  30

Ala Thr Glu Phe Phe Ser Thr Lys Ala Ala Lys Lys Pro Glu Ala Lys
        35                  40                  45

Arg Glu Ala Ile Val Lys Ala Asp Glu Asp Asp Asn Glu Glu Thr Leu
    50                  55                  60

Lys Gln Arg Leu Thr Asn Leu Glu Lys Lys Ile Thr Asn Val Thr Thr
65                  70                  75                  80

Lys Phe Glu Gln Ile Glu Lys Cys Cys Lys Arg Asn Asp Glu Val Leu
                85                  90                  95

Phe Arg Leu Glu Asn His Ala Glu Thr Leu Arg Ala Ala Met Ile Ser
            100                 105                 110

Leu Ala Lys Lys Ile Asp Val Gln Thr Gly Arg Arg Pro Tyr Glu Tyr
        115                 120                 125

Pro Tyr Asp Val Pro Asp Tyr Ala
    130                 135

<210> SEQ ID NO 5
<211> LENGTH: 1032
<212> TYPE: DNA
<213> ORGANISM: Artificial Sequence
<220> FEATURE:
<223> OTHER INFORMATION: Synthetic smallpox vaccine sequence 3

<400> SEQUENCE: 5

```
atggactgga cctggatcct gttcctggtg ccgctgcca cccgggtgca cagcaagacc    60
atcagcgtgg tgaccctgct gtgcgtgctg ccgccgtgg tgtacagcac ctgcaccgtg   120
cccaccatga caacgccaa gctgaccagc accgagacca gcttcaacga caagcagaag   180
gtgaccttca cctgcgacca gggctaccac agcagcgacc ccaacgccgt gtgcgagacc   240
```

```
gacaagtgga agtacgagaa cccctgcaag aaaatgtgca ccgtgagcga ctacatcagc    300
gagctgtaca acaagcccct gtacgaggtg aacagcacca tgaccctgag ctgcaacggc    360
gagaccaagt acttccgctg cgaggaaaag aacggcaaca ccagctggaa cgacaccgtg    420
acctgcccca atgccgagtg ccagcccctg cagctggaac acggcagctg ccagcccgtg    480
aaagagaagt acagcttcgg cgagtacatg accatcaact gcgacgtggg ctacgaggtg    540
atcggcgcca gctacatcag ctgcaccgcc aacagctgga atgtgatccc ctcctgccag    600
cagaaatgcg acatgcccag cctgagcaac ggcctgatca gcggcagcac cttcagcatc    660
ggcggcgtga tccacctgtc ctgcaagagc ggcttcaccc tgaccggcag ccccagctcc    720
acctgcatcg acggcaagtg gaaccccgtg ctgcccatct gcgtgcggac caacgaggaa    780
ttcgaccccg tggacgacgg ccccgacgac gagaccgacc tgagcaagct gtccaaggac    840
gtggtgcagt acgagcagga aatcgagagc ctggaagcca cctaccacat catcatcgtg    900
gccctgacca tcatgggcgt gatctttctg atcagcgtga tcgtgctggt gtgcagctgc    960
gacaagaaca cgaccagta caagttccac aagctgctgc cctaccccta cgacgtgccc   1020
gactacgcct ga                                                       1032
```

<210> SEQ ID NO 6
<211> LENGTH: 343
<212> TYPE: PRT
<213> ORGANISM: Artificial Sequence
<220> FEATURE:
<223> OTHER INFORMATION: Synthetic smallpox vaccine sequence 3

<400> SEQUENCE: 6

```
Met Asp Trp Thr Trp Ile Leu Phe Leu Val Ala Ala Thr Arg Val
1               5                   10                  15

His Ser Lys Thr Ile Ser Val Val Thr Leu Leu Cys Val Leu Pro Ala
                20                  25                  30

Val Val Tyr Ser Thr Cys Thr Val Pro Thr Met Asn Asn Ala Lys Leu
            35                  40                  45

Thr Ser Thr Glu Thr Ser Phe Asn Asp Lys Gln Lys Val Thr Phe Thr
        50                  55                  60

Cys Asp Gln Gly Tyr His Ser Ser Asp Pro Asn Ala Val Cys Glu Thr
65                  70                  75                  80

Asp Lys Trp Lys Tyr Glu Asn Pro Cys Lys Lys Met Cys Thr Val Ser
                85                  90                  95

Asp Tyr Ile Ser Glu Leu Tyr Asn Lys Pro Leu Tyr Glu Val Asn Ser
            100                 105                 110

Thr Met Thr Leu Ser Cys Asn Gly Glu Thr Lys Tyr Phe Arg Cys Glu
        115                 120                 125

Glu Lys Asn Gly Asn Thr Ser Trp Asn Asp Thr Val Thr Cys Pro Asn
    130                 135                 140

Ala Glu Cys Gln Pro Leu Gln Leu Glu His Gly Ser Cys Gln Pro Val
145                 150                 155                 160

Lys Glu Lys Tyr Ser Phe Gly Glu Tyr Met Thr Ile Asn Cys Asp Val
                165                 170                 175

Gly Tyr Glu Val Ile Gly Ala Ser Tyr Ile Ser Cys Thr Ala Asn Ser
            180                 185                 190

Trp Asn Val Ile Pro Ser Cys Gln Gln Lys Cys Asp Met Pro Ser Leu
        195                 200                 205

Ser Asn Gly Leu Ile Ser Gly Ser Thr Phe Ser Ile Gly Gly Val Ile
    210                 215                 220
```

His Leu Ser Cys Lys Ser Gly Phe Thr Leu Thr Gly Ser Pro Ser Ser
225                 230                 235                 240

Thr Cys Ile Asp Gly Lys Trp Asn Pro Val Leu Pro Ile Cys Val Arg
            245                 250                 255

Thr Asn Glu Glu Phe Asp Pro Val Asp Asp Gly Pro Asp Asp Glu Thr
        260                 265                 270

Asp Leu Ser Lys Leu Ser Lys Asp Val Val Gln Tyr Glu Gln Glu Ile
        275                 280                 285

Glu Ser Leu Glu Ala Thr Tyr His Ile Ile Ile Val Ala Leu Thr Ile
    290                 295                 300

Met Gly Val Ile Phe Leu Ile Ser Val Ile Val Leu Val Cys Ser Cys
305                 310                 315                 320

Asp Lys Asn Asn Asp Gln Tyr Lys Phe His Lys Leu Leu Pro Tyr Pro
            325                 330                 335

Tyr Asp Val Pro Asp Tyr Ala
            340

<210> SEQ ID NO 7
<211> LENGTH: 636
<212> TYPE: DNA
<213> ORGANISM: Artificial Sequence
<220> FEATURE:
<223> OTHER INFORMATION: Synthetic smallpox vaccine sequence 4

<400> SEQUENCE: 7
atggactgga cctggatcct gttcctggtc gccgctgcca cccgggtgca cagcatgacc        60
cccgagaacg acgaggaaca gaccagcgtg ttcagcgcca ccgtgtacgg cgacaagatc       120
cagggcaaga acaagcggaa gcgggtgatc ggcctgtgca tccggatctc tatggtgatc       180
agcctcctgt ccatgatcac catgagcgcc tttctgatcg tgcggctgaa ccagtgcatg       240
agcgccaacg aggccgccat caccgatgcc gccgtggccg tggctgccgc ctccagcacc       300
caccggaagg tggccagcag caccacccag tacgaccaca agagagctg caacggcctg        360 tactaccagg gcagctgcta catcctgcac agcgactacc agctgttctc cgacgccaag       420
gccaactgca ccgccgagag cagcaccctg cccaacaaga gcgacgtgct gattacctgg       480
ctcatcgact acgtggagga cacctggggc agcgacggca ccccatcac caagaccacc       540 tccgactacc aggacagcga cgtgagccag gaagtgcgga agtacttctg cgtgaaaacc       600
atgaactacc cctacgacgt gcccgactac gcctga                                636

<210> SEQ ID NO 8
<211> LENGTH: 211
<212> TYPE: PRT
<213> ORGANISM: Artificial Sequence
<220> FEATURE:
<223> OTHER INFORMATION: Synthetic smallpox vaccine sequence 4

<400> SEQUENCE: 8

Met Asp Trp Thr Trp Ile Leu Phe Leu Val Ala Ala Ala Thr Arg Val
1               5                   10                  15

His Ser Met Thr Pro Glu Asn Asp Glu Glu Gln Thr Ser Val Phe Ser
            20                  25                  30

Ala Thr Val Tyr Gly Asp Lys Ile Gln Gly Lys Asn Lys Arg Lys Arg
        35                  40                  45

Val Ile Gly Leu Cys Ile Arg Ile Ser Met Val Ile Ser Leu Leu Ser
    50                  55                  60

Met Ile Thr Met Ser Ala Phe Leu Ile Val Arg Leu Asn Gln Cys Met

```
                65                  70                  75                  80
Ser Ala Asn Glu Ala Ala Ile Thr Asp Ala Val Ala Val Ala Ala
                    85                  90                  95

Ala Ser Ser Thr His Arg Lys Val Ala Ser Thr Thr Gln Tyr Asp
                100                 105                 110

His Lys Glu Ser Cys Asn Gly Leu Tyr Tyr Gln Gly Ser Cys Tyr Ile
                115                 120                 125

Leu His Ser Asp Tyr Gln Leu Phe Ser Asp Ala Lys Ala Asn Cys Thr
        130                 135                 140

Ala Glu Ser Ser Thr Leu Pro Asn Lys Ser Asp Val Leu Ile Thr Trp
145                 150                 155                 160

Leu Ile Asp Tyr Val Glu Asp Thr Trp Gly Ser Asp Gly Asn Pro Ile
                165                 170                 175

Thr Lys Thr Thr Ser Asp Tyr Gln Asp Ser Asp Val Ser Gln Glu Val
                180                 185                 190

Arg Lys Tyr Phe Cys Val Lys Thr Met Asn Tyr Pro Tyr Asp Val Pro
            195                 200                 205

Asp Tyr Ala
    210

<210> SEQ ID NO 9
<211> LENGTH: 1023
<212> TYPE: DNA
<213> ORGANISM: Artificial Sequence
<220> FEATURE:
<223> OTHER INFORMATION: Synthetic smallpox vaccine sequence 5

<400> SEQUENCE: 9
atggactgga cctggatcct gttcctggtg gctgccgcca ctagggtgca cagcacccgg     60
ctgcccatcc tgctgctgct gatcagcctg gtgtacgcca cccccttccc tcagactagc    120
aagaagatcg cgacgacgc cacctgagc tgcaaccgga caacaccaa cgactacgtg       180
gtgatgagcg cctggtacaa agagcccaac tctatcattc tgctggccgc caagagcgac    240
gtgctgtact cgacaactac accaaggac aagatcagct acgacagccc ctacgacgac     300
ctggtgacca ccatcaccat caagagcctg accgccaggg acgccggcac ctacgtgtgc    360
gccttttca tgaccagcac caccaacgac accgacaagg tggactacga ggaatacagc     420
accgagctga tcgtgaacac cgacagcgag agcaccatcg acatcatcct gagcggcagc    480
acccacagcc ccgagaccag cagcaagaag cccgactaca tcgacaacag caactgcagc    540
agcgtgttcg agatcgccac ccccgagccc atcaccgata cgtggagga ccataccgat     600
accgtgacct acaccagcga cagcatcaat actgtgagtg cctctagcgg cgagtccacc    660
accgacgaga ctcctgagcc tattacagac aaagaggatc acaccgtcac agataccgtg    720
tcttacacaa ccgtgagcac ctccagcggc atcgtgacca ccaagagcac caccgatgac    780
gccgacctgt acgacaccta caacgacaac gataccgtcc ccctaccac cgtgggcggc     840
tccaccacct ccatcagcaa ctacaagacc aaggacttcg tggagatctt cggcatcacc    900
gccctgatca tcctgtccgc cgtggccatc ttctgtatca cctactacat ctacaataag    960
cggagccgga agtacaagac cgagaacaag gtgtaccccct acgatgtgcc cgactacgcc  1020
tga                                                                 1023

<210> SEQ ID NO 10
<211> LENGTH: 340
<212> TYPE: PRT
<213> ORGANISM: Artificial Sequence
```

```
<220> FEATURE:
<223> OTHER INFORMATION: Synthetic smallpox vaccine sequence 5

<400> SEQUENCE: 10

Met Asp Trp Thr Trp Ile Leu Phe Leu Val Ala Ala Thr Arg Val
1               5                   10                  15

His Ser Thr Arg Leu Pro Ile Leu Leu Leu Ile Ser Leu Val Tyr
            20                  25                  30

Ala Thr Pro Phe Pro Gln Thr Ser Lys Lys Ile Gly Asp Ala Thr
        35                  40                  45

Leu Ser Cys Asn Arg Asn Asn Thr Asn Asp Tyr Val Val Met Ser Ala
    50                  55                  60

Trp Tyr Lys Glu Pro Asn Ser Ile Ile Leu Ala Ala Lys Ser Asp
65              70                  75                  80

Val Leu Tyr Phe Asp Asn Tyr Thr Lys Asp Lys Ile Ser Tyr Asp Ser
                85                  90                  95

Pro Tyr Asp Asp Leu Val Thr Thr Ile Thr Ile Lys Ser Leu Thr Ala
            100                 105                 110

Arg Asp Ala Gly Thr Tyr Val Cys Ala Phe Phe Met Thr Ser Thr Thr
            115                 120                 125

Asn Asp Thr Asp Lys Val Asp Tyr Glu Glu Tyr Ser Thr Glu Leu Ile
            130                 135                 140

Val Asn Thr Asp Ser Glu Ser Thr Ile Asp Ile Ile Leu Ser Gly Ser
145                 150                 155                 160

Thr His Ser Pro Glu Thr Ser Ser Lys Lys Pro Asp Tyr Ile Asp Asn
                165                 170                 175

Ser Asn Cys Ser Ser Val Phe Glu Ile Ala Thr Pro Glu Pro Ile Thr
            180                 185                 190

Asp Asn Val Glu Asp His Thr Asp Thr Val Thr Tyr Thr Ser Asp Ser
            195                 200                 205

Ile Asn Thr Val Ser Ala Ser Ser Gly Glu Ser Thr Thr Asp Glu Thr
            210                 215                 220

Pro Glu Pro Ile Thr Asp Lys Glu Asp His Thr Val Thr Asp Thr Val
225                 230                 235                 240

Ser Tyr Thr Thr Val Ser Thr Ser Ser Gly Ile Val Thr Thr Lys Ser
                245                 250                 255

Thr Thr Asp Asp Ala Asp Leu Tyr Asp Thr Tyr Asn Asp Asn Asp Thr
            260                 265                 270

Val Pro Pro Thr Thr Val Gly Gly Ser Thr Thr Ser Ile Ser Asn Tyr
            275                 280                 285

Lys Thr Lys Asp Phe Val Glu Ile Phe Gly Ile Thr Ala Leu Ile Ile
            290                 295                 300

Leu Ser Ala Val Ala Ile Phe Cys Ile Thr Tyr Tyr Ile Tyr Asn Lys
305                 310                 315                 320

Arg Ser Arg Lys Tyr Lys Thr Glu Asn Lys Val Tyr Pro Tyr Asp Val
                325                 330                 335

Pro Asp Tyr Ala
            340

<210> SEQ ID NO 11
<211> LENGTH: 717
<212> TYPE: DNA
<213> ORGANISM: Artificial Sequence
<220> FEATURE:
<223> OTHER INFORMATION: Synthetic smallpox vaccine sequence 6

<400> SEQUENCE: 11
```

```
atggactgga cctggatcct gttcctggtg gctgccgcca ctagagtgca cagcgccgag    60
accaaagagt tcaagaccct gtacaacctg ttcatcgaca gctacctcca gaagctggcc   120
cagcacagca tccccaccaa cgtgacctgc gccatccaca tcggcgaggt gatcggccag   180
ttcaagaact gcgccctgcg gatcaccaac aagtgcatga gcaacagcag actgagcttc   240
accctgatgg tggagagctt catcgaggtg atcagcctgc tgcccgagaa ggacaggcgg   300
gccatcgccg aggaaatcgg catcgacctg gacgacgtgc ccagcgccgt gagcaagctg   360
gaaaagaact gcaacgccta cgccgaggtg aacaacatca tcgacatcca gaagctcgac   420
atcggcgaat gcagcgcccc tcccggccag cacatgctgc tccagatcgt gaacaccggc   480
tccgccgagg ccaactgcgg cctccagacc atcgtgaaga gcctgaacaa gatctacgtg   540
ccccccatca tcgagaaccg gctgccctac tacgacccct ggtttctggt cggcgtggcc   600
atcatcctgg tgatcttcac cgtggccatc tgctccatcc ggcggaacct ggccctgaag   660
tacagatacg gcaccttcct gtacgtgtac ccctacgacg tgcctgacta cgcctga      717
```

<210> SEQ ID NO 12
<211> LENGTH: 238
<212> TYPE: PRT
<213> ORGANISM: Artificial Sequence
<220> FEATURE:
<223> OTHER INFORMATION: Synthetic smallpox vaccine sequence 6

<400> SEQUENCE: 12

Met Asp Trp Thr Trp Ile Leu Phe Leu Val Ala Ala Thr Arg Val
1               5                   10                  15

His Ser Ala Glu Thr Lys Glu Phe Lys Thr Leu Tyr Asn Leu Phe Ile
            20                  25                  30

Asp Ser Tyr Leu Gln Lys Leu Ala Gln His Ser Ile Pro Thr Asn Val
        35                  40                  45

Thr Cys Ala Ile His Ile Gly Glu Val Ile Gly Gln Phe Lys Asn Cys
    50                  55                  60

Ala Leu Arg Ile Thr Asn Lys Cys Met Ser Asn Ser Arg Leu Ser Phe
65                  70                  75                  80

Thr Leu Met Val Glu Ser Phe Ile Glu Val Ile Ser Leu Leu Pro Glu
                85                  90                  95

Lys Asp Arg Arg Ala Ile Ala Glu Glu Ile Gly Ile Asp Leu Asp Asp
            100                 105                 110

Val Pro Ser Ala Val Ser Lys Leu Glu Lys Asn Cys Asn Ala Tyr Ala
        115                 120                 125

Glu Val Asn Asn Ile Ile Asp Ile Gln Lys Leu Asp Ile Gly Glu Cys
    130                 135                 140

Ser Ala Pro Pro Gly Gln His Met Leu Leu Gln Ile Val Asn Thr Gly
145                 150                 155                 160

Ser Ala Glu Ala Asn Cys Gly Leu Gln Thr Ile Val Lys Ser Leu Asn
                165                 170                 175

Lys Ile Tyr Val Pro Pro Ile Ile Glu Asn Arg Leu Pro Tyr Tyr Asp
            180                 185                 190

Pro Trp Phe Leu Val Gly Val Ala Ile Ile Leu Val Ile Phe Thr Val
        195                 200                 205

Ala Ile Cys Ser Ile Arg Arg Asn Leu Ala Leu Lys Tyr Arg Tyr Gly
    210                 215                 220

Thr Phe Leu Tyr Val Tyr Pro Tyr Asp Val Pro Asp Tyr Ala
225                 230                 235

```
<210> SEQ ID NO 13
<211> LENGTH: 1053
<212> TYPE: DNA
<213> ORGANISM: Artificial Sequence
<220> FEATURE:
<223> OTHER INFORMATION: Synthetic smallpox vaccine sequence 7

<400> SEQUENCE: 13
atggactgga cctggattct gttcctggtg gctgccgcca ctagagtgca cagcgccgct      60
gccaagaccc ccgtgatcgt ggtgcccgtg atcgaccggc tgcccagcga gaccttcccc     120
aacgtgcacg agcacatcaa cgaccagaaa ttcgacgacg tgaaggacaa cgaggtgatg     180
cccgagaagc ggaacgtggt ggtggtgaag gacgaccccg accactacaa ggactacgcc     240
ttcatccagt ggaccggcgg caacatccgg aacgacgaca gtacaccca cttttttcagc    300 ggcttttgca caccatgtg caccgaggaa ccaagcgga catcgcccg gcacctggcc       360 ctgtgggaca gcaacttctt caccgagctg gaaaacaaga agtggagta cgtggtgatc     420 gtggagaacg acaacgtgat cgaggatatc accttcctgc ggcccgtgct gaaggccatg     480
cacgacaaga gatcgacat cctgcagatg cgggagatca tcaccggcaa caaggtgaaa    540
accgagctgg tgatggacaa gaaccacgcc atcttcacct acaccggcgg ctacgacgtg     600
agcctgagcg cctacatcat ccgggtgacc accgccctga catcgtgga cgagatcatc      660 aagagcggcg gactgagcag cggcttctac ttcgagatcg cccggatcga aacgagatg      720 aagatcaacc ggcagatcct ggacaacgcc gccaagtacg tggagcacga ccccagactg     780
gtggccgagc accggttcga aacatgaag cccaacttt ggagccggat cggcaccgcc       840
gccacaaagc gctaccccgg cgtgatgtac gccttcacca cccccctgat cagcttttc     900 ggcctgttcg acatcaatgt gatcggcctg atcgtgatcc tgttcatcat gttcatgctg     960
atcttcaacg tgaagagcaa gctgctgtgg ttcctgaccg gcaccttcgt gaccgccttc    1020
atctacccct acgacgtgcc cgactacgcc tga                                  1053

<210> SEQ ID NO 14
<211> LENGTH: 350
<212> TYPE: PRT
<213> ORGANISM: Artificial Sequence
<220> FEATURE:
<223> OTHER INFORMATION: Synthetic smallpox vaccine sequence 7

<400> SEQUENCE: 14

Met Asp Trp Thr Trp Ile Leu Phe Leu Val Ala Ala Thr Arg Val
1               5                   10                  15

His Ser Ala Ala Ala Lys Thr Pro Val Ile Val Pro Val Ile Asp
                20                  25                  30

Arg Leu Pro Ser Glu Thr Phe Pro Asn Val His Glu His Ile Asn Asp
        35                  40                  45

Gln Lys Phe Asp Asp Val Lys Asp Asn Glu Val Met Pro Glu Lys Arg
    50                  55                  60

Asn Val Val Val Val Lys Asp Asp Pro Asp His Tyr Lys Asp Tyr Ala
65                  70                  75                  80

Phe Ile Gln Trp Thr Gly Gly Asn Ile Arg Asn Asp Asp Lys Tyr Thr
                85                  90                  95

His Phe Phe Ser Gly Phe Cys Asn Thr Met Cys Thr Glu Glu Thr Lys
            100                 105                 110

Arg Asn Ile Ala Arg His Leu Ala Leu Trp Asp Ser Asn Phe Phe Thr
        115                 120                 125
```

```
Glu Leu Glu Asn Lys Lys Val Glu Tyr Val Val Ile Val Glu Asn Asp
        130                 135                 140

Asn Val Ile Glu Asp Ile Thr Phe Leu Arg Pro Val Leu Lys Ala Met
145                 150                 155                 160

His Asp Lys Lys Ile Asp Ile Leu Gln Met Arg Glu Ile Ile Thr Gly
                165                 170                 175

Asn Lys Val Lys Thr Glu Leu Val Met Asp Lys Asn His Ala Ile Phe
            180                 185                 190

Thr Tyr Thr Gly Gly Tyr Asp Val Ser Leu Ser Ala Tyr Ile Ile Arg
        195                 200                 205

Val Thr Thr Ala Leu Asn Ile Val Asp Glu Ile Ile Lys Ser Gly Gly
    210                 215                 220

Leu Ser Ser Gly Phe Tyr Phe Glu Ile Ala Arg Ile Glu Asn Glu Met
225                 230                 235                 240

Lys Ile Asn Arg Gln Ile Leu Asp Asn Ala Ala Lys Tyr Val Glu His
                245                 250                 255

Asp Pro Arg Leu Val Ala Glu His Arg Phe Glu Asn Met Lys Pro Asn
            260                 265                 270

Phe Trp Ser Arg Ile Gly Thr Ala Ala Thr Lys Arg Tyr Pro Gly Val
        275                 280                 285

Met Tyr Ala Phe Thr Thr Pro Leu Ile Ser Phe Phe Gly Leu Phe Asp
    290                 295                 300

Ile Asn Val Ile Gly Leu Ile Val Ile Leu Phe Ile Met Phe Met Leu
305                 310                 315                 320

Ile Phe Asn Val Lys Ser Lys Leu Leu Trp Phe Leu Thr Gly Thr Phe
                325                 330                 335

Val Thr Ala Phe Ile Tyr Pro Tyr Asp Val Pro Asp Tyr Ala
            340                 345                 350

<210> SEQ ID NO 15
<211> LENGTH: 831
<212> TYPE: DNA
<213> ORGANISM: Artificial Sequence
<220> FEATURE:
<223> OTHER INFORMATION: Synthetic smallpox vaccine sequence 8

<400> SEQUENCE: 15
atggactgga cctggattct gttcctggtg gctgccgcca ctagagtcca ctctggcgca    60
gccgccagca tccagaccac cgtgaacacc ctgagcgagc ggatcagcag caagctggaa   120
caggaagcca cgcctctgc ccagacaaag tgcgacatcg atcggcaa cttctacatc      180 cggcagaacc acggctgcaa cctgaccgtg aagaacatgt gcagcgccga cgccgacgca   240
cagctggatg ccgtgctgtc tgccgccacc gagacctaca cgggcctgac ccccgagcag   300
aaagcctacg tgcccgccat gttcacagcc gccctgaaca tccagacaag cgtgaatacc   360
gtggtgcggg acttcgagaa ctacgtgaag cagacctgca acagcagcgc cgtggtggac   420
aacaagctga agatccagaa cgtgatcatc gacgagtgct atggcgcccc tggcagcccc   480
accaacctgg aattcatcaa caccggcagc agcaagggca actgcgccat caaggccctg   540
atgcagctga ccaccaaggc caccacccag atcgccccca gcaggtggc cggcaccggc   600 gtgcagttct acatgatcgt gatcggcgtg atcatcctgg ccgccctgtt catgtactac   660
gccaagcgga tgctgttcac cagcaccaac gacaagatca agctgatcct ggccaacaaa   720
gaaaacgtgc actggaccac ctacatggac cctttttcc ggaccagccc catggtgatc   780
gccaccaccg acatgcagaa ctaccctac gacgtgcccg actacgcctg a              831
```

-continued

```
<210> SEQ ID NO 16
<211> LENGTH: 276
<212> TYPE: PRT
<213> ORGANISM: Artificial Sequence
<220> FEATURE:
<223> OTHER INFORMATION: Synthetic smallpox vaccine sequence 8

<400> SEQUENCE: 16

Met Asp Trp Thr Trp Ile Leu Phe Leu Val Ala Ala Ala Thr Arg Val
1               5                   10                  15

His Ser Gly Ala Ala Ala Ser Ile Gln Thr Thr Val Asn Thr Leu Ser
            20                  25                  30

Glu Arg Ile Ser Ser Lys Leu Glu Gln Glu Ala Asn Ala Ser Ala Gln
        35                  40                  45

Thr Lys Cys Asp Ile Glu Ile Gly Asn Phe Tyr Ile Arg Gln Asn His
    50                  55                  60

Gly Cys Asn Leu Thr Val Lys Asn Met Cys Ser Ala Asp Ala Asp Ala
65                  70                  75                  80

Gln Leu Asp Ala Val Leu Ser Ala Ala Thr Glu Thr Tyr Ser Gly Leu
                85                  90                  95

Thr Pro Glu Gln Lys Ala Tyr Val Pro Ala Met Phe Thr Ala Ala Leu
            100                 105                 110

Asn Ile Gln Thr Ser Val Asn Thr Val Val Arg Asp Phe Glu Asn Tyr
        115                 120                 125

Val Lys Gln Thr Cys Asn Ser Ser Ala Val Val Asp Asn Lys Leu Lys
    130                 135                 140

Ile Gln Asn Val Ile Ile Asp Glu Cys Tyr Gly Ala Pro Gly Ser Pro
145                 150                 155                 160

Thr Asn Leu Glu Phe Ile Asn Thr Gly Ser Ser Lys Gly Asn Cys Ala
                165                 170                 175

Ile Lys Ala Leu Met Gln Leu Thr Thr Lys Ala Thr Thr Gln Ile Ala
            180                 185                 190

Pro Lys Gln Val Ala Gly Thr Gly Val Gln Phe Tyr Met Ile Val Ile
        195                 200                 205

Gly Val Ile Ile Leu Ala Ala Leu Phe Met Tyr Tyr Ala Lys Arg Met
    210                 215                 220

Leu Phe Thr Ser Thr Asn Asp Lys Ile Lys Leu Ile Leu Ala Asn Lys
225                 230                 235                 240

Glu Asn Val His Trp Thr Thr Tyr Met Asp Thr Phe Phe Arg Thr Ser
                245                 250                 255

Pro Met Val Ile Ala Thr Thr Asp Met Gln Asn Tyr Pro Tyr Asp Val
            260                 265                 270

Pro Asp Tyr Ala
        275

<210> SEQ ID NO 17
<211> LENGTH: 22
<212> TYPE: DNA
<213> ORGANISM: Artificial Sequence
<220> FEATURE:
<223> OTHER INFORMATION: Primer 1

<400> SEQUENCE: 17
atgtactatc tcaacgtagt ag                                                22

<210> SEQ ID NO 18
<211> LENGTH: 26
<212> TYPE: DNA
```

```
<213> ORGANISM: Artificial Sequence
<220> FEATURE:
<223> OTHER INFORMATION: Primer 2

<400> SEQUENCE: 18
ctgcagaaca taaaactatt aatatg                                          26

<210> SEQ ID NO 19
<211> LENGTH: 18
<212> TYPE: DNA
<213> ORGANISM: Artificial Sequence
<220> FEATURE:
<223> OTHER INFORMATION: Taqman Probe Component 1
<220> FEATURE:
<221> NAME/KEY: misc_feature
<222> LOCATION: (18)..(18)
<223> OTHER INFORMATION: where n is "g" modified by SEQ ID NO:20

<400> SEQUENCE: 19
agtgcttggt ataaggan                                                   18

<210> SEQ ID NO 20
<211> LENGTH: 8
<212> TYPE: PRT
<213> ORGANISM: Artificial Sequence
<220> FEATURE:
<223> OTHER INFORMATION: Taqman Probe Component 2
<220> FEATURE:
<221> NAME/KEY: MISC_FEATURE
<222> LOCATION: (1)..(1)
<223> OTHER INFORMATION: where "Xaa" is "M" modified by SEQ ID NO:19
<220> FEATURE:
<221> NAME/KEY: MISC_FEATURE
<222> LOCATION: (1)..(3)
<223> OTHER INFORMATION: where "Xaa" is "M" modified by SEQ ID NO:19

<400> SEQUENCE: 20

Xaa Ala Ala Gly Asx Asn Phe Gln
1               5
```